(12) United States Patent
Mellis et al.

(10) Patent No.: US 7,361,350 B2
(45) Date of Patent: *Apr. 22, 2008

(54) USE OF AN IL-1 ANTAGONIST FOR TREATING ARTHRITIS

(75) Inventors: Scott Mellis, New Rochelle, NY (US); Neil Stahl, Carmel, NY (US); Allen Radin, New York, NY (US); Steven Weinstein, Hartsdale, NY (US); Denise Calaprice, Nyack, NY (US); Margaret Karow, Putnam Valley, NY (US); Joanne Papadopoulos, LaGrangeville, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 371 days.

This patent is subject to a terminal disclaimer.

(21) Appl. No.: 11/056,730

(22) Filed: Feb. 11, 2005

(65) Prior Publication Data

US 2005/0197293 A1    Sep. 8, 2005

Related U.S. Application Data

(63) Continuation-in-part of application No. 10/282,162, filed on Oct. 28, 2002, now Pat. No. 6,927,044.

(51) Int. Cl.
*A61K 39/00* (2006.01)
*C07K 14/715* (2006.01)

(52) U.S. Cl. .............. 424/185.1; 424/192.1; 514/12; 530/350

(58) Field of Classification Search ............ None
See application file for complete search history.

(56) References Cited

U.S. PATENT DOCUMENTS 5,470,952 A    11/1995  Stahl et al.
2003/0072756 A1*  4/2003  Bendele et al. .......... 424/145.1

FOREIGN PATENT DOCUMENTS

| EP | 0835939 A2 | 6/1991 |
|---|---|---|
| EP | 0533006 A1 | 9/1992 |
| WO | WO93/19163 | 9/1993 |
| WO | WO93/19777 | 10/1993 |
| WO | WO94/22914 | 10/1994 |
| WO | WO95/06737 | 3/1995 |
| WO | WO96/11213 | 4/1996 |
| WO | WO96/23881 | 8/1996 |
| WO | WO96/35783 | 11/1996 |
| WO | WO97/15669 | 5/1997 |
| WO | WO97/31946 | 9/1997 |
| WO | WO99/37772 | 7/1999 |

OTHER PUBLICATIONS

Greenfeeder, S.A., et al., (1995) J. Biol. Chem. 270(23):13757-13765.
Seipelt, I., et al., (1997) Biochem. Biophys. Res. Comm. 293:534-542.
Stahl, N., et al., (1999) FASEB J. Abstract, 1457.
Campion, G.V., et al., (1996) Arthritis & Rheumatism 39(7):1092-1101.
Bresnihan, B., et al., (1998) Arthritis & Rheumatism 41(12):2196-2204.

* cited by examiner

*Primary Examiner*—Eileen B. O'Hara
(74) *Attorney, Agent, or Firm*—Valeta Gregg, Esq.

(57) ABSTRACT

Methods of treating, inhibiting, or ameliorating arthritis, including rheumatoid arthritis, osteoarthritis, psoriatic arthritis, ankylosing spondylitis, or juvenile rheumatoid arthritis, in a human subject in need thereof, comprising administering to a subject in need a therapeutic amount of an interleukin 1 (IL-1) antagonist, wherein arthritis inhibited, or ameliorated. The IL-1 antagonist is an IL-1-specific fusion protein comprising an IL-1 binding portion of the extracellular domain of human Il-1RAcP, an IL-1 binding portion of the extracellular domain of human IL-1RI, and a multimerizing component antagonist, preferably comprising a sequence selected from the group consisting of SEQ ID NO:4, 6, 8, 10, 12, 14, 16, 18, 20, 22, 24, 26, or a substantially identical sequence.

9 Claims, 4 Drawing Sheets

USE OF AN IL-1 ANTAGONIST FOR TREATING ARTHRITIS

CROSS-REFERENCE TO RELATED APPLICATIONS

This application is a continuation in part of U.S. Ser. No. 10/282,162 filed 28 Oct. 2002, now U.S. Pat. No. 6,927,044, which is hereby incorporated by reference into this application in its entirety.

FIELD OF THE INVENTION

The invention relates to methods of treating arthritis, including rheumatoid arthritis and osteoarthritis, with a an interleukin-1 (IL-1) antagonist.

SUMMARY OF THE INVENTION

In a first aspect, the invention features a method of treating, inhibiting, or ameliorating arthritis, comprising administering to a subject in need an interleukin 1 (IL-1) antagonist. An IL-1 antagonist is a compound capable of blocking or inhibiting the biological action of IL-1, including fusion proteins capable of trapping and blocking IL-1. In a preferred embodiment, the IL-1-specific fusion protein comprising two IL-1 receptor components and a multimerizing component, for example, an IL-1-specific fusion protein described in U.S. Pat. No. 6,472,179 and U.S. patent publication No. 2003/0143697, published 31 Jul. 2003, herein specifically incorporated by reference in their entirety. An IL-1-specific fusion protein comprises an IL-1 binding portion of the extracellular domain of human Il-1RAcP, an IL-1 binding portion of the extracellular domain of human IL-1RI, and a multimerizing component. In a specific embodiment, the IL-1-specific fusion protein is the fusion protein shown in SEQ ID NO:4, 6, 8, 10, 12,14, 16, 18, 20, 22, 24, 26. In one preferred embodiment, the IL-1-specific fusion protein is SEQ ID NO:10. The invention encompasses the use of an IL-1-specific fusion protein substantially identical to the protein of SEQ ID NO:4, 6, 8, 10, 12,14, 16, 18, 20, 22, 24, or 26, that is, a protein having at least 95% identity, at least 97% identity, at least 98% identity to the protein of SEQ ID NO:4, 6, 8, 10, 12,14, 16, 18, 20, 22, 24, or 26 and capable of binding and inhibiting IL-1. Further, in specific embodiments, the IL-1 antagonist is a modified IL-1-specific fusion protein comprising one or more receptor components and one or more immunoglobulin-derived components specific for IL-1 and/or an IL-1 receptor. In another embodiment, the IL-1 antagonist is a modified IL-1-specific fusion protein comprising one or more immunoglobulin-derived components specific for IL-1 and/or an IL-1 receptor.

The subject being treated is most preferably a human diagnosed as suffering from arthritis, including, but not limited to, rheumatoid arthritis, osteoarthritis, psoriatic arthritis, ankylosing spondylitis, and juvenile rheumatoid arthritis, and other inflammatory arthritides, as well as other arthritidies in which inflammatory mediators plays a role. More specifically, the subject is a human adult or child diagnosed with arthritis. Methods for diagnosing the presence of arthritis are known in the art.

In a second aspect, the invention features a method of treating, inhibiting, or ameliorating osteoarthritis, comprising administering to a subject in need an interleukin 1 (IL-1) antagonist. The IL-1 antagonist useful in the methods of the invention is described above. The subject being treated is most preferably a human diagnosed as suffering from osteoarthritis.

In a third aspect, the invention features a therapeutic method of treating rheumatoid arthritis, comprising administering a pharmaceutical composition comprising an IL-1-specific fusion protein and a pharmaceutically acceptable carrier.

In a fifth aspect, the invention features a therapeutic method of treating psoriatic arthritis, comprising administering a pharmaceutical composition comprising an IL-1-specific fusion protein and a pharmaceutically acceptable carrier.

In a sixth aspect, the invention features a therapeutic method of treating ankylosing spondylitis, comprising administering a pharmaceutical composition comprising an IL-1-specific fusion protein and a pharmaceutically acceptable carrier.

In a seventh aspect, the invention features a therapeutic method of treating juvenile rheumatoid arthritis, comprising administering a pharmaceutical composition comprising an IL-1-specific fusion protein and a pharmaceutically acceptable carrier.

The method of the invention includes administration of the IL-1 antagonist by any means known to the art, for example, subcutaneous, intramuscular, intranasal, intraarticular, intravenous, topical, transdermal administration or oral routes of administration. Preferably, administration is by subcutaneous, intraarticular, or intravenous injection or infusion.

In specific embodiments of the therapeutic method of the invention, the subject is treated with a combination of an IL-1-specific fusion protein and a second therapeutic agent. The second therapeutic agent may be a second IL-1 antagonist such as a chimeric, humanized or human antibody to IL-1α or β (such as CDP484, Celltech) or to the IL-1 receptor (for example, AMG-108, Amgen; R-1599, Roche), IL-1Ra (anakinra, Amgen; IL-1ra gene therapy, Orthogen), and ICE inhibitor, such as Vx-765 (Vertex), p38 MAP inhibitors, IKK ½ inhibitors (such as, UK436303, Pfizer; SPC-839, Serono/Signal), collagenase inhibitors (Periostat™, Collagenex), etc. The second therapeutic agent may also be selected from an anti-IL-18 compound, such as IL-18BP or a derivative, an IL-18-specific fusion protein (trap), anti-IL-18, anti-IL-18R1, or anti-IL-18Rβ. Other co-therapies include low dose colchicine for FMF, aspirin or other NSAIDs, steroids such as prednisone, prednisolone, Depo-Medrol™ and Kenalog™; and other disease modifying anti-rheumatic drugs (DMARDs) such as methotrexate; low dose cyclosporine A, TNF inhibitors such as Enbrel®, or Humira®, other inflammatory inhibitors such as inhibitors of caspase-1, p38, IKK½, CTLA-4Ig, anti-IL-6 or anti-IL6Ra; and hyaluronic derivates such as Hyalgan™, Synvisc™, Orthovisc™, and Supartz™.

Other objects and advantages will become apparent from a review of the ensuing detailed description.

DETAILED DESCRIPTION OF THE INVENTION

Figure 1:
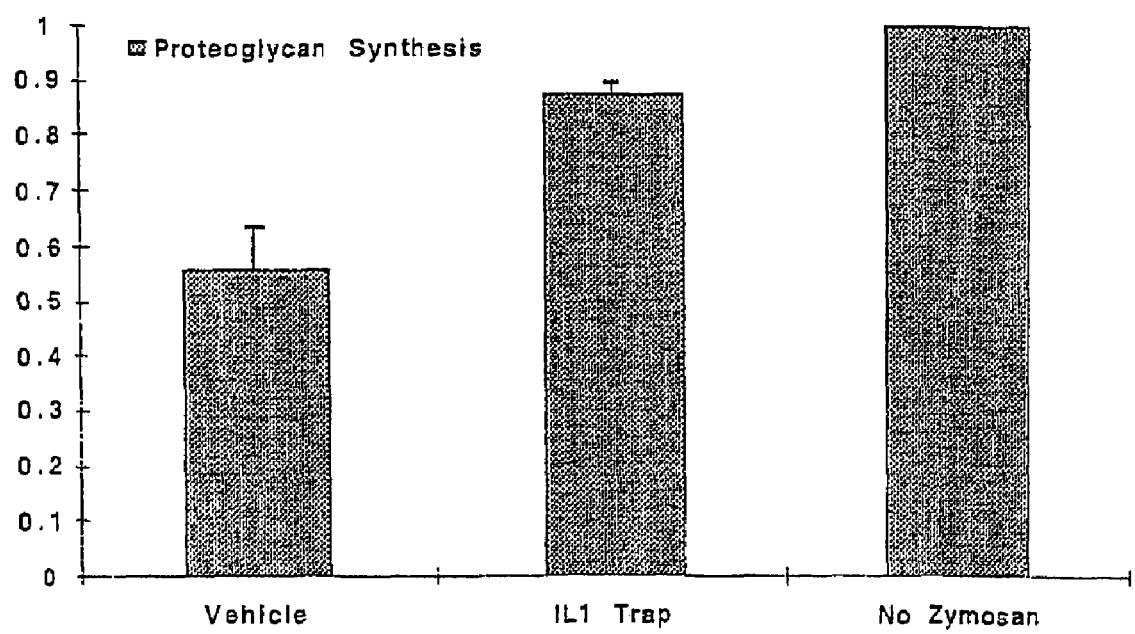
FIG. 1: Human IL-1-specific fusion protein blocks the effects of IL-1 in inflamed joints.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference in their entirety.

Rheumatoid Arthritis and Osteoarthritis

Rheumatoid arthritis (RA) is a chronic systemic disease characterized by progressive joint deformity and joint destruction in which cytokines play a central pathogenic role. The clinical course of RA is variable and often shows a remitting pattern. Three forms of RA can be distinguished: mild, self-limiting disease; mildly progressive disease; and aggressive disease which is difficult to control with medication, and is characterized by functional decline and radiologic deterioration of the joints, e.g., joint space narrowing and erosions. In accordance with the systemic nature of the disease, there are extra-articular manifestations which include vasculitis, alveolitis, and ocular disease. Prevalence of the disease as reported in the literature is approximately 1% of the U.S. population, with women accounting for two-thirds of all cases. The disease affects mainly adults but there is a juvenile form of rheumatoid arthritis (Chikanza et al (1998) J Pharm Pharmacol 50:357-69).

Onset of RA is often insidious with fatigue, anorexia, generalized weakness, and vague musculoskeletal symptoms. Specific symptoms appear later. Several joints, usually in a symmetrical fashion, are affected. Most often these are joints of the hands, wrists, knees, and feet. Joints are painful and swollen, and motion is limited. Morning stiffness of more than one hour is a very typical finding. With persistent inflammation, a variety of deformities develop which include most typically radial deviation of the wrist and hyperextension or flexion of the proximal interphalangeal joints; other deformities occur as well. Atrophy of skeletal muscle sets in. In approximately 20 to 30% of all patients, there is development of rheumatoid nodules on periarticular structures or sites of trauma, but they are usually of limited clinical significance. The nodules may be found in other structures such as the pleura or the meninges. Rheumatoid vasculitis can affect nearly all organ systems (lung, GI-tract, liver, spleen, pancreas, lymph nodes, testis, and the eye). Osteoporosis is common and may be aggravated by corticosteroids used in therapy (Lipsky (1998) Harrison's Textbook of Medicine 14$^{th}$ Ed. pp.1880-8).

Laboratory findings may include elevation of erythrocyte sedimentation rate (ESR) and C-reactive protein (CRP) along with rheumatoid factor. Rheumatoid factor is an autoantibody against the Fc portion of IgG found in more than two-thirds of all patients. High titers of rheumatoid factor are a good indicator of disease activity. Mild anemia (normochromic, normocytic) and eosinophilia may be present as well. With progression of the disease, X-ray abnormalities such as general deformity, juxta-articular osteopenia, loss of articular cartilage, and bone erosion become more evident.

There is no curative treatment for RA. All drug regimens primarily attempt to relieve the symptoms and the inflammation. Aspirin and other nonsteroidal anti-inflammatory drugs (NSAIDs) with a rapid onset of action are the first line of treatment. Selective COX-2 inhibitors such as Celebrex® and Vioxx® have been found to be better tolerated than regular NSAIDS which act both on COX-1 and COX-2. Oral glucocorticoids are added to the drug regimen if necessary. The third line of treatment includes disease modifying antirheumatic drugs (DMARDs); they have a slow onset of action, in some cases several months. DMARDs include azathioprine, sulphasalazine, gold, D-penicillamine, hydroxychloroquine, methotrexate, and cyclosporine. The most recent addition of etanercept/Enbrel® (chimeric TNF-receptor fusion protein) to the therapeutic armamentarium appears to be a successful step to improve patient treatment in a rational way. A second drug, infliximab/Remicade® (monoclonal anti-TNF antibody) has been approved for treatment of RA in combination with methotrexate. A third, IL-1ra (Antril®), a recombinant version of the naturally occurring IL-1 receptor antagonist, has been reported to have clinical benefit, as well (Bresnihan et al. (1998) Arthritis & Rheumatism 41:2196-2204; Campion et al. (1996) Arthritis & Rheumatism 39:1092-1101; Cohen et al. (1999) Arthritis & Rheumatism Abstracts 42(Supp):S273).

Osteoarthritis is the most common form of arthritis in Western populations (Jordan et al. (2003) Ann Rheum Dis. 62(12):1145-55). Knee OA, characterized clinically by pain and functional disability, is the leading cause of chronic disability among the elderly in the US. Risk factors for OA include age, gender, race, trauma, repetitive stress/joint overload, muscle weakness, and genetic factors.

Pathologically, the most striking changes in OA are focal loss of articular cartilage and marginal and central new bone formation. However, OA is not simply a disease of articular cartilage and the subchondral bone. Rather, it is a disease of the synovial joint, with alterations also found in the synovium, capsule, ligaments, periarticular muscle, and sensory nerves.

Although OA was once considered a non-inflammatory arthropathy, patients often present with signs and symptoms consistent with local inflammation and synovitis, and recent evidence from preclinical and clinical studies supports the role of inflammation and inflammatory mediators in its pathophysiology (Pelletier et al. (2001) Arthritis Rheum 44(6):1237-47). Both chondrocytes and synovium in OA can produce proinflammatory cytokines, including IL-1β, which can alter cartilage homeostasis in favor of cartilage degradation. For example, IL-1β appears to be a major factor stimulating matrix metalloproteinase synthesis and other cartilage catabolic responses in OA. Thus, inflammation and inflammatory mediators may play a role in the joint destruction associated with OA as well as in pain.

Current treatment of osteoarthritis includes non-medicinal therapy, medicinal therapy, and surgical treatments. Non-medicinal treatments include exercise, thermal treatment, and assistive devices or bracing. For knee OA, range-of-motion and strengthening exercises are geared toward reduction of impairment, improvement of function, and joint protection. Medications include analgesics (e.g., acetaminophen), non-steroidal anti-inflammatory drugs (NSAIDS) that are either non-selective cyclooxygenase (COX) inhibitors or selective inhibitors of the COX-2 enzyme, injected intra-articular corticosteroids or viscosupplementation, and proven or putative disease-modifying osteoarthritis drugs (DMOADs). Surgical procedures include joint debridement and lavage, and lastly total knee arthroplasty.

The most commonly used medicinal treatments for knee OA typically provide less than 50% relief of pain. For example, use of acetaminophen, selective NSAIDs or non-selective NSAIDs typically results in mean improvements in knee OA pain of no more than 30 points from a baseline of ~70 points using 100 point (100-mm) visual analog scales (Kivitz et al (2002) J Fam Pract 51(6):530-537). While this is a clinically important improvement, this indicates that there is substantial room for improvement in the pain management of knee OA. Further, no therapy has been demonstrated to retard the progression of structural degradation.

The pain and structural alterations of osteoarthritis are associated with inflammation and with alterations in inflammatory mediators, including IL-1. Hence, there is potential utility for agents that diminish the action of IL-1 in the treatment of both OA pain and OA disease (structural) modification. Indeed, a small, uncontrolled clinical study of intra-articularly administered IL-1 receptor antagonist, IL-1ra (anakinra), in knee osteoarthritis demonstrated a prolonged reduction in knee pain, supporting the potential of IL-1 inhibition as a therapeutic approach in treating OA (Goupille et al. (2003) Arthritis Rheum 48(suppl):S696). Although IL-1-specific fusion protein has not previously been studied in osteoarthritis, it has been shown to have anti-inflammatory activity associated with clinical effect in both animal models and humans in clinical trials.

Definitions

By the term "blocker", "inhibitor", or "antagonist" is meant a substance that retards or prevents a chemical or physiological reaction or response. Common blockers or inhibitors include but are not limited to antisense molecules, antibodies, antagonists and their derivatives. More specifically, an example of an IL-1 blocker or inhibitor is an IL-1 antagonist including, but not limited to, IL-1-specific fusion protein, which binds and inhibits IL-1.

By the term "therapeutically effective dose" is meant a dose that produces the desired effect for which it is administered. The exact dose will depend on the purpose of the treatment, and will be ascertainable by one skilled in the art using known techniques (see, for example, Lloyd (1999) The Art, Science and Technology of Pharmaceutical Compounding).

By the term "substantially identical" is meant a protein sequence having at least 95% identity to an amino acid sequence selected from the group consisting of the amino acid sequences SEQ ID NOs: 2, 4, 6, 8, 10, 12, 14, 16, 18, 20, 22, 24, and 26, and capable of binding IL-1 and inhibiting the biological activity of IL-1.

The term "identity" or "homology" is construed to mean the percentage of amino acid residues in the candidate sequence that are identical with the residue of a corresponding sequence to which it is compared, after aligning the sequences and introducing gaps, if necessary to achieve the maximum percent identity for the entire sequence, and not considering any conservative substitutions as part of the sequence identity. Neither N- or C-terminal extensions nor insertions will be construed as reducing identity or homology. Methods and computer programs for the alignment are well known in the art. Sequence identity may be measured using sequence analysis software (e.g., Sequence Analysis Software Package, Genetics Computer Group, University of Wisconsin Biotechnology Center, 1710 University Ave., Madison, Wis. 53705). This software matches similar sequences by assigning degrees of homology to various substitutions, deletions, and other modifications.

IL-1-Specific Fusion Protein Antagonists

IL-1-specific fusion proteins (sometimes referred to as "IL-1 traps") are multimers of fusion proteins containing IL-1 receptor components and a multimerizing component capable of interacting with the multimerizing component present in another fusion protein to form a higher order structure, such as a dimer. Cytokine traps include two distinct receptor components that bind a single cytokine, resulting in the generation of antagonists with dramatically increased affinity over that offered by single component reagents. In fact, the cytokine traps that are described herein are among the most potent cytokine blockers ever described. Briefly, the cytokine traps called IL-1 traps are comprised of the extracellular domain of human IL-1R Type I (IL-1RI) or Type II (IL-1RII) followed by the extracellular domain of human IL-1 Accessory protein (Il-1RAcP), followed by a multimerizing component. In one embodiment, the multimerizing component is an immunoglobulin-derived domain, such as, for example, the Fc region of human IgG, including part of the hinge region, the CH2 and CH3 domains. An immunoglobulin-derived domain may be selected from any of the major classes of immunoglobulins, including IgA, IgD, IgE, IgG and IgM, and any subclass or isotype, e.g. IgG1, IgG2, IgG3 and IgG4; IgA-1 and IgA-2. For a more detailed description of the IL-1 traps, see WO 00/18932, which publication is herein specifically incorporated by reference in its entirety. Preferred IL-1-specific fusion proteins have the amino acid sequence shown in SEQ ID NOs: 2, 4, 6, 8, 10, 12, 14, 16, 18, 20, 22, 24, and 26, or a substantially identical protein at least 95% identity to a sequence of SEQ ID NO:4, 6, 8, 10, 12, 14, 16, 18, 20, 22, 24, or 26, and capable of binding and inhibiting IL-1.

In specific embodiments, the IL-1 antagonist comprises an antibody fragment capable of binding IL-1α, IL-1β, IL-1R1 and/or Il-1RAcP, or a fragment thereof. The preferred embodiment would be an antagonist of IL-1β. One embodiment of an IL-1 antagonist comprising one or more antibody fragments, for example, single chain Fv (scFv), is described in U.S. Pat. No. 6,472,179, which publication is herein specifically incorporated by reference in its entirety. In all of the IL-1 antagonist embodiments comprising one or more antibody-derived components specific for IL-1 or an IL-1 receptor, the components may be arranged in a variety of configurations, e.g., a IL-1 receptor component(s)-scFv(s)-multimerizing component; IL-1 receptor component(s)-multimerizing component-scFv(s); scFv(s)-IL-1 receptor component(s)-multimerizing component, ScFv-ScFv-Fc, etc., so long as the molecule or multimer is capable of inhibiting the biological activity of IL-1.

Combination Therapies

In numerous embodiments, the IL-1 antagonists of the present invention may be administered in combination with one or more additional compounds or therapies. Combination therapy may be simultaneous or sequential. The IL-1-specific fusion proteins of the invention may be combined with, for example, a chimeric, humanized or human antibody to IL-1α or β (such as CDP-484, Celltech) or to the IL-1 receptor (for example, AMG-108, Amgen; R-1599, Roche), IL-1Ra (anakinra, Amgen; IL-1ra gene therapy, Orthogen), and ICE inhibitor, such as Vx-765 (Vertex), p38 MAP inhibitors, IKK ½ inhibitors (such as, UK-436303, Pfizer; SPC-839, Serono/Signal), collagenase inhibitors (Periostat™, Collagenex), etc. The second therapeutic agent may also be selected from an anti-IL-18 compound, such as IL-18BP or a derivative, an IL-18 trap, anti-IL-18, anti-IL-18R1, or anti-IL-18RAcP. Other co-therapies include low dose colchicine for FMF, aspirin or other NSAIDs, steroids such as prednisone, prednisolone, and other disease modifying anti-rheumatic drugs (DMARDs) such as methotrexate; low dose cyclosporine A, TNF inhibitors such as Enbrel®, or Humira®), other inflammatory inhibitors such as inhibitors of caspase-1, p38, IKK½, CTLA-4Ig, anti-IL-6 or anti-IL6Ra; and hyaluronic derivates such as Hyalgan™ or Synvisc™.

Pharmaceutical Compositions

The present invention also provides pharmaceutical compositions. Such compositions comprise a therapeutically effective amount of an active agent, and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin.

In a preferred embodiment, the composition is formulated in accordance with routine procedures as a pharmaceutical composition adapted for intravenous administration to human beings. Where necessary, the composition may also include a solubilizing agent and a local anesthetic such as lidocaine to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The active agents of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Other features of the invention will become apparent in the course of the following descriptions of exemplary embodiments which are given for illustration of the invention and are not intended to be limiting thereof.

EXAMPLES

The following example is put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Human IL-1-Specific Fusion Protein Blocks the Effects of IL-1 in Inflamed Joints Zymosan is a yeast cell wall extract that when injected into the knee causes acute inflammation and upregulation of IL-1β in the joint (Joosten et al. (1994) supra). Chondrocytes will respond to the inflammation and local IL-1β by down regulating proteoglycan synthesis, a feature of human arthritis that contributes to the gradual destruction of cartilage in the joint (van den Berg W B et al. (1982) Rheum Intl 1:165-169). Antagonists to IL-1β can be used to evaluate their ability to block the effects of zymosan-induced elevations in IL-1β.

Anesthetized male C57BL/6 mice (Taconic) were given an intra-articular (i.a.) injection of Zymosan A (Sigma; 300 µg in 10 µl) into the right knee joint through the patellar ligament. Sterile PBS was injected i.a. (10 µl) into the left knee joint through the patellar ligament. Twenty-four hours prior to i.a. injections, animals were treated with either vehicle or hIL-1 trap 569 (SEQ ID NO:1-2) (19 mg/kg, s.c.). The patellae were removed 24 h after injection of zymosan in order to measure proteoglycan synthesis as described by van den Berg and colleagues (1982). Briefly, each patella and associated ligament were incubated for 3 h at 37° C., 5% $CO_2$ in media (RPMI with HEPES, $HCO_3$, glutamine & penicillin/streptomycin) containing 10 µCi/ml $^{35}$S-sulfate (NEN DuPont). Following incubation, tissue was washed and fixed overnight in 10% formalin (VWR). The tissue was then placed in Decalcifing Solution (J. T. Baker) for 4 h prior to dissection of the patella from surrounding tissue. Each patella was then incubated overnight in Solvable (Packard) at 50° C. Ultima Gold liquid scintillation fluid (Packard) was added and the samples were counted in a liquid scintillation counter. Values were reported as the ratio of cpm of zymosan patella/cpm of vehicle patella for each animal.

Intra-articular injection of zymosan reduces proteoglycan synthesis by approximately 50% relative to vehicle injection (FIG. 1). Administration of hIL-1-trap prior to zymosan injection blocked the local action of IL-1β and proteoglycan synthesis returned to approximately 90% of control. These data demonstrate that hIL-1 trap 569 can penetrate the joints after subcutaneous injection to effectively neutralize the biological effect of IL-1 within these joints.

Example 2

Murine IL-1-Trap Reduces the Severity of Arthritis Symptoms in a Zymosan-Accelerated Collagen-Induced Arthritis (CIA) Model IL-1 has been implicated in the development of inflammation and cartilage destruction in rheumatoid arthritis (Dinarello (1996) Blood 87(6):2095-2147; Wooley et al. (1993) Arthritis & Rheumatism 36(9): 1305-1314). Collagen-induced arthritis (CIA) is a widely studied animal model of inflammatory polyarthritis with similarities to rheumatoid arthritis; common histopathological features include joint inflammation and erosion, synovial hyperplasia and inflammatory cell infiltration (Joe et al. (1999) Mol Med Today 5:367-369). Since previous studies have shown that various anti-IL-1 treatments have a positive effect on reducing arthritis symptoms in CIA animals (van den Berg et al. (1994) Clin Exp Immunol 95:237-243; Joosten et al. (1999) J Immunol 163:5049-5055.; van de Loo et al. (1992) J Rheumatol 19:348-356.), Applicants examined the effect of a murine version of the IL-1-specific fusion protein (mIL-1 trap) on the progression of arthritis symptoms in this animal model. The mIL-1 trap consists of the extracellular domain of murine II-1RAcP, followed by the extracellular domain of murine IL-1RI, followed by the hinge, CH2 and CH3 domain of murine IgG2a. The human version of the IL-1 trap is poorly cross-reactive with rodent IL-1.

Male DBA-1 mice (Jackson Laboratories) were immunized intradermally at the base of the tail with 100 μg/50 μl bovine Type II collagen (CII; Chondrex) emulsified with complete and incomplete Freund's adjuvant (2:1:1 ratio; Chondrex) and boosted intradermally with CII (100 μg/50 μl) emulsified with incomplete Freund's adjuvant on day 21. Since CIA in DBA-1 mice occurs gradually over a long time period with a low incidence (Joosten et al. (1994) supra). Applicants synchronized the onset of arthritis symptoms by injecting the animals intraperitoneally on day 30 with 3 mg zymosan (Sigma). Two hours prior to zymosan injection, the mice were randomly distributed into treatment groups and were injected with either vehicle or mIL-1 trap (31 or 10 mg/kg, 3×/week, 8 injections, s.c.). Arthritis symptoms (ASI scores, as described by Wooley et al. (1993) Arthritis & Rheumatism 36(9): 1305-1314) in the paws were evaluated 3×/week by individuals who were blinded to the treatment groups. Animals were sacrificed 24 h after the 8th injection at which time paw width along with ASI scores were measured.

Figure 2:
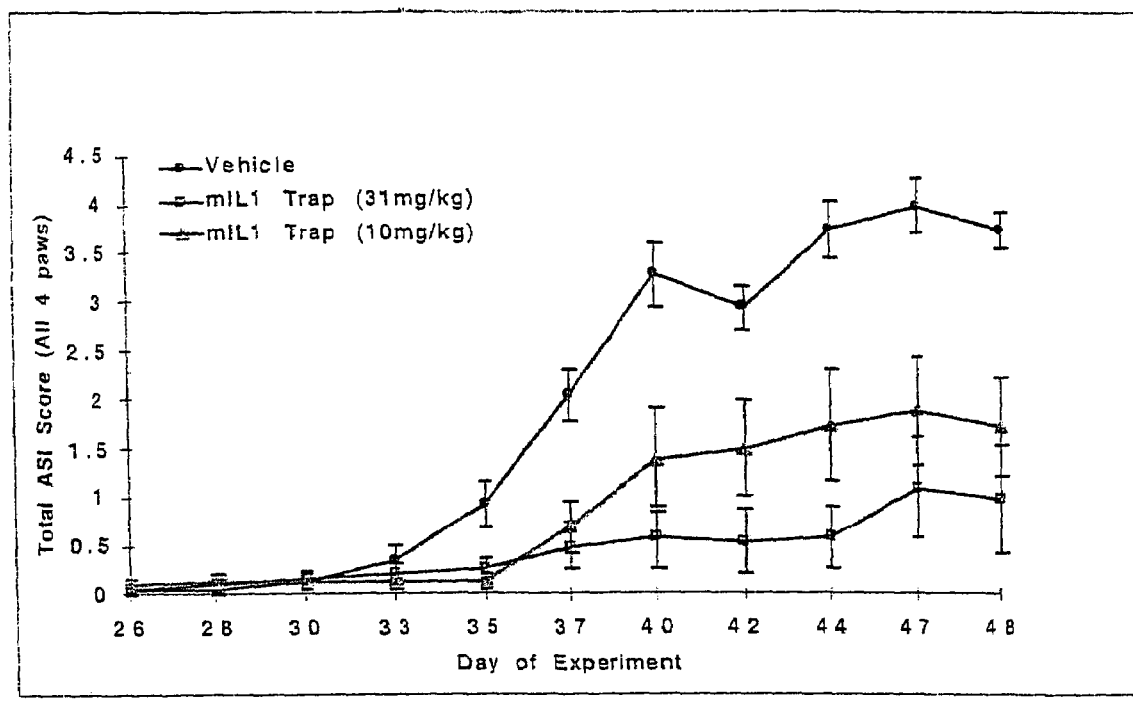
FIGS. 2-3: Murine IL-1-specific fusion protein reduces the severity of arthritis symptoms in a Zymosan-Accelerated Collagen-Induced Arthritis (CIA) model.
Figure 3:
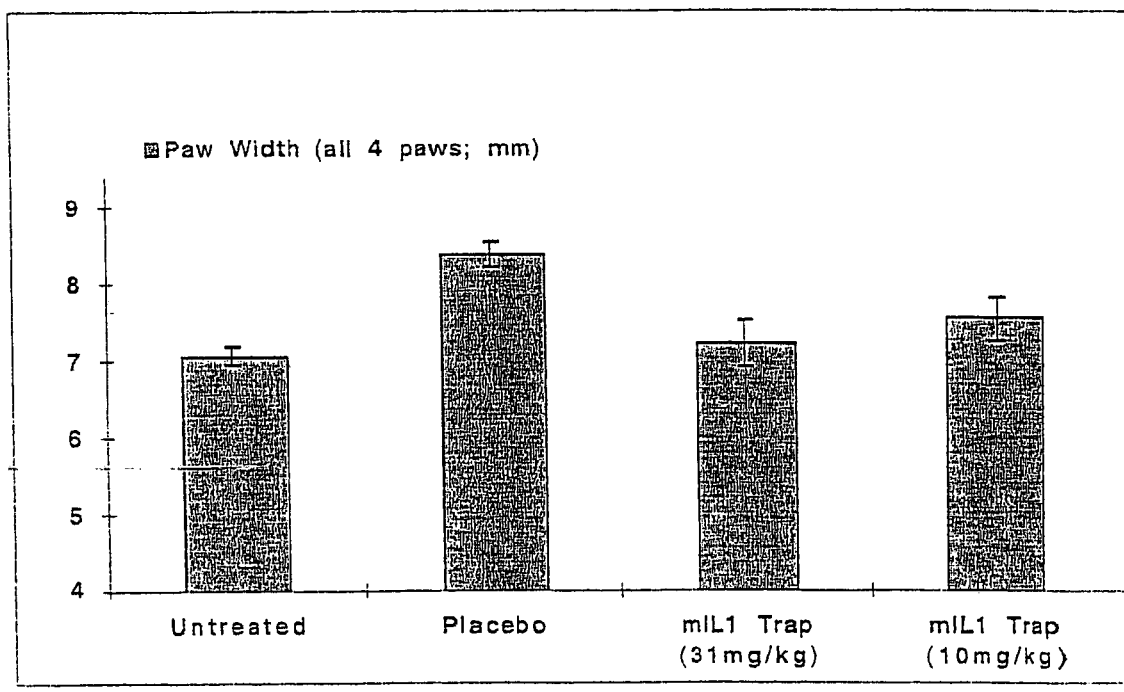
Figure 4:
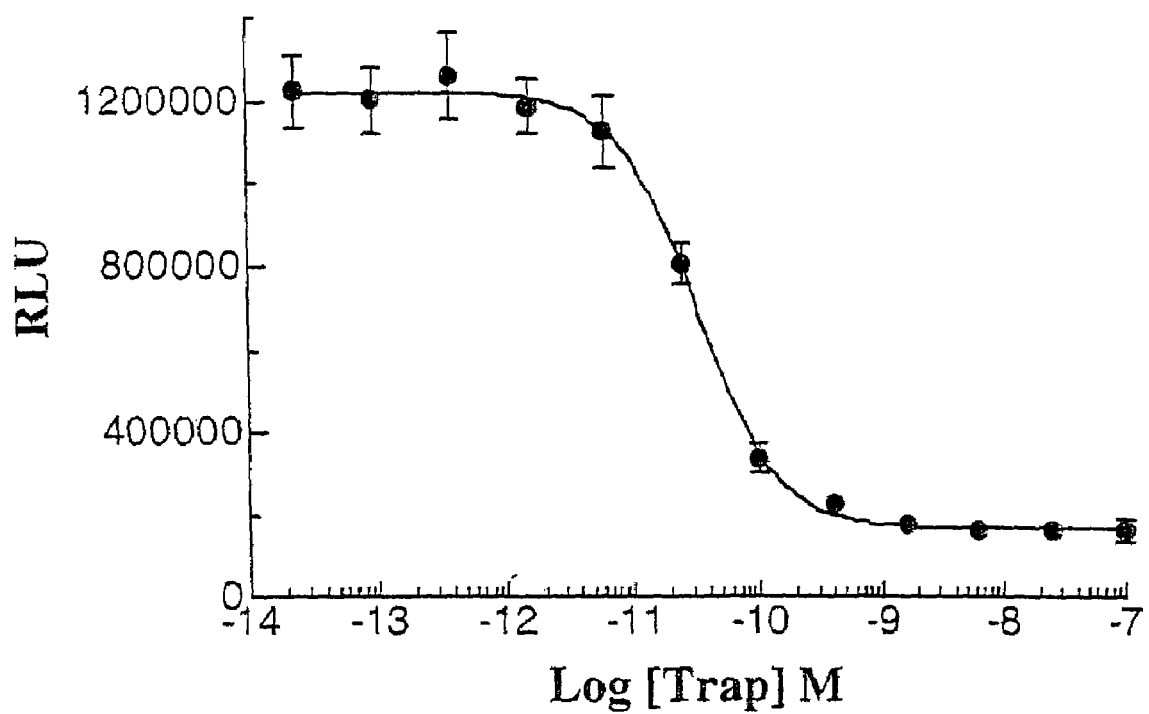
FIG. 4: Various concentrations of IL-1-specific fusion protein 1649 were incubated in the presence of 5 pM human IL-1b overnight at room temperature.

Within 5 days after i.p injection of zymosan, vehicle treated animals had an significant increase in ASI score relative to those receiving mIL-1 trap (FIG. 2) with symptoms reaching a maximum 10 to 14 days after zymosan injection. Murine IL-1 trap acted in a dose-dependent fashion such that animals receiving 10 mg/kg trap had more arthritis symptoms (greater ASI score) than those receiving 31 mg/kg. However, both mIL-1 trap-treated groups had a significantly lower degree of arthritis symptoms than vehicle. This difference in ASI score is also reflected in the paw width at the time of sacrifice (FIG. 3). Animals receiving mIL-1 trap had paw widths that were similar to those of naive, non-collagen immunized animals. These data indicate that mIL-1 trap can effectively neutralize IL-1 and block the development of arthritic joints.

Example 3

IL-1-Specific Fusion Protein Treatment of Rheumatoid Arthritis

A Phase 1, placebo controlled, randomized, double-blind, combined single and multiple dose, dose-escalation study was conducted in subjects with rheumatoid arthritis (RA). IL-1-specific fusion protein was dosed subcutaneously. In the single-dose part, subjects in a given dose cohort received either a sing subcutaneous dose of IL-1-specific fusion protein (SEQ ID NO:10) (50, 100, 200, 400 or 800 mg/kg) or placebo. In the multi-dose phase, patients in a given cohort received six weekly doses of IL-1-specific fusion protein (50, 100, 200, 400 or 800 mg/kg) or placebo. The terminal half-life of IL-1-specific fusion protein ranged from 5.3 to 8.9 days and clearance ranged from 0.49 to 1.00 mL/hr/kg. The AUC and Cmax were dose dependent and approximately linear. No subject developed antibodies against the IL-1-specific fusion protein.

Exploratory efficacy assessments were also obtained in the multiple dose phase of the study. Swollen and tender joint counts and serum CRP levels were improved with 800 mg/kg of the IL-1-specific fusion protein dose compared to placebo.

A Phase 2 dose range-finding study evaluated 12 weekly fixed doses of the IL-1-specific fusion protein (25, 50 or 100 mg administered subcutaneously) and placebo in RA subjects. The safety analysis indicated the drug to be well tolerated with no evidence of dose-limiting toxicities.

Unaudited efficacy results indicate that a greater proportion of subjects treated with 100 mg of the IL-1-specific fusion protein achieved American College of Rheumatology (ACR) 20, 50 and 70 scores compared with placebo, although these results were not statistically significant. Subjects on the 100 mg dose of the IL-1-specific fusion protein demonstrated significant improvement (p<0.05) relative to placebo for (1) time to onset of ACR20 and ACR50 responses, ACR-N, AUC of ACR-N, DAS28, AUC of DAS28, and ESR levels.

Example 4

Efficacy of Systemic Treatment with IL-1-Specific Fusion Protein of Osteoarthritis of the Knee A study is conducted to assess the efficacy of systemic treatment (including intravenous and subcutaneous administration) with doses of up to 2000 mg IV of the IL-1-specific fusion protein (SEQ ID NO:10) versus placebo for reduction of knee pain, functional disability, and joint stiffness in subjects with osteoarthritis of the knee.

Endpoints. The primary efficacy endpoint is the change in Patient's Assessment of Arthritis Pain—visual analogue scale (VAS) score (PAAP-VAS; 100-mm scale) from Baseline to Week 4. Additional efficacy endpoints are evaluated at each time point (compared to Baseline) including: categorical reduction in Patient's Assessment of Arthritis Pain –VAS score by at least 20% (responder); change of the WOMAC™ Osteoarthritis Index pain, disability, and joint stiffness dimensions; change in each of the items in the WOMAC™ Osteoarthritis Index; change in Patient's Global Assessment of Arthritis Condition; change in Physician's Global Assessment of Arthritis Condition; amount of rescue medication (acetaminophen) used; and changes in potential biomarkers of OA disease activity.

Study Design. This is a randomized, double-blind, parallel group, 12-week trial of the IL-1-specific fusion protein vs. placebo in subjects with osteoarthritis of the knee. After screening, eligible patients are washed-out of any NSAIDs taken, and are required to flare to be eligible for randomization. If NSAIDs are not being taken at Screening, patients demonstrate a clinical response to a NSAID within the previous 6 months and have discontinued treatment for reasons other than lack of efficacy. Approximately 160 subjects at approximately 12 sites are randomly allocated in a 1:1 ratio to receive single IV doses of up to 2000 mg IL-1-specific fusion protein or placebo. Subjects are then followed and assessed for efficacy, safety, and tolerability at Weeks 2, 4, 8, and 12. The primary endpoint of pain as measured by PMP-VAS will be at Week 4.

Osteoarthritis Disease Biomarkers. Serum and urine are obtained periodically during the study for possible examination of biomarkers of osteoarthritis disease activity. The urine sample must be from the first (preferable) or second morning void. Instructions and materials for collection will be provided with the laboratory kits provided by the central laboratory. Biomarkers to be examined will potentially include (but not necessarily be limited to) CTX-II (C-terminal crosslinking telopeptide of collagen type II, typically measured in urine) and COMP (cartilage oligomeric matrix protein, typically measured in serum).

Patient's Assessment of Arthritis Pain—Visual Analog Scale. The Patient's Assessment of Arthritis Pain—Visual Analog Scale (PAAP-VAS) (below) is a self-administered instrument to be used at each study visit to quantify pain in each knee. The question is to be answered using a 100 mm visual analog scale, considering the patient's status during the 24-hour period leading up to and including the time of evaluation.

Physician's and Patient's Global Assessments of Arthritis Condition. Global assessments of arthritis condition (Example 7 below) are made by each of the physician and subject using 100 mm VAS scales, considering the subject's condition during the 24 hours leading up to and including the time of assessment. The physician's global assessment is made by the physician performing the focused exam of the knees, after completing this examination. Each of the physician's and patient's assessments is made without knowledge of the other's assessment score.

WOMAC™–VA Osteoarthritis Index. The WOMAC™–VA Index (Appendix K) is a self-administered questionnaire that asks 24 questions about the pain (5 questions), stiffness (2 questions), and functional limitations (17 questions) associated with arthritis. Each question is answered by making a mark along a 10.0 cm (100 mm) visual analog scale anchored by the terms "none" (left end) and "extreme" (right end). Questions are to be answered considering the patient's status during the 24-hour period leading up to and including the time of evaluation.

Example 5

American College of Rheumatology Classification Criteria for Osteoarthritis: Criteria for Classification of Osteoarthritis (OA) of the Knee Using Clinical and Radiographic Evidence Knee pain+at least 1 of 3+osteophytes: (1) Age>50 years; (2) stiffness<30 minutes; (3) crepitus (Altman et al. (1986) Arthritis Rheum 29:1039-1049).

Example 6

Kellgren-Lawrence Grading Criteria for Radiographic Severity of Knee Osteoarthritis Grade 0 is defined as no OA severity with radiographic findings of no feature of OA. Grade I is defined as doubtful OA severity with minute osteophyte, with radiographic findings of doubtful significance. Grade II is defined as minimal OA severity with radiographic findings of moderate diminution of joint space. Grade II is defined as moderate OA severity with radiographic findings of moderate diminution of joint space. Grade IV is defined as severe OA with radiographic findings of joint space greatly impaired with sclerosis of subchondral bone (Kellgren et al. (1957) Ann Rhem Dis. 1957: 16: 494-501: and Department of Rheumatology and Medical Illustration, University of Manchester. The Epidemiology of Chronic Rheumatism. Atlas of Standard Radiographs of Arthritis. Philadelphia, Pa.: FA Davis Company: 1973: 1-15.

Example 7

Pain Assessments

Patient's Assessment of Arthritis Pain (VAS). Patient makes a vertical mark through each of two lines which best describes the amount of pain due to arthritis in the right or left knee experienced in the last 24 hours. Range from no pain to most severe pain.

Physician's Global Assessment of Arthritis Condition. Physician is instructed to make a global assessment of the patient's disease status ranging from very good to very poor.

Patient's Global Assessment of Arthritis Condition. Patient is instructed to mark through a line ranging from very well to very poorly in response to the questions: "Considering all the ways your arthritis affects you, how are you doing today (and in the last 24 hours)?"

Example 8

Intraarticular Administration of an IL-1-Specific Fusion Protein to Subjects Suffering from Osteoarthritis An initial 12-week, randomized, double blind, placebo-controlled, repeated dose, dose-escalation, safety and efficacy study is conducted with up to 60 subjects diagnosed as suffering from osteoarthritis of the knee. The subjects are randomly assigned to one of four cohorts and are treated with a single initial dose of 22 mg, 66 mg, 220 mg, 320 mg of IL-1-specific fusion protein or placebo, followed by a second dose at week 8. Observations are obtained periodically during the course of the 12-week study as described above.

A second 24-week, double blind, placebo-controlled, proof-of-concept, safety and efficacy study is conducted with about 160 patients diagnosed with osteoarthritis of the knee. Patients are randomly assigned to treatment with placebo or with the maximum tolerated dose (determined as described above) of the IL-1-specific fusion protein (SEQ ID NO:10). The primary efficacy endpoint is the change in PAAP-VAS at week 12. After week 12, but prior to week 20, contingent upon recurrence of symptoms (i.e., index knee pain), patients receive a second dose of study drug. Analyses of efficacy are based on efficacy outcome parameters as described above, and include analysis of dosing interval ("time to failure") for the IL-1-specific fusion protein relative to placebo.

A 12-week, double blind, placebo-controlled, single dose, dose-ranging, safety and efficacy study is conducted with about 320 patients diagnosed with osteoarthritis of the knee. Patients are randomly assigned to one of four treatment groups: placebo or one of 3 doses of the IL-1-specific fusion protein. The primary efficacy endpoint is the change in PMP-VAS at week 12. Analyses of efficacy are based on efficacy outcome parameters as indicated above.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

We claim:

1. A method of treating, inhibiting, and/or ameliorating arthritis in a subject suffering therefrom, comprising administering to a subject in need a therapeutic amount of an interleukin 1 (IL-1) antagonist, wherein arthritis is treated, inhibited and/or ameliorated, wherein the IL-1 antagonist comprises the amino acid sequence of SEQ ID NO:10.

2. The method of claim 1, wherein the administration is subcutaneous, intravenous, or intraarticular.

3. The method of claim 2, wherein administration is single or multiple intravenous infusion.

4. The method of claim 1, wherein a therapeutically effective amount is between 1 to 30 mg/kg.

5. The method of claim 2, wherein a administration comprises one or more intravenous dose(s) of a therapeutically effective amount of the IL-1-specific fusion protein of up to about 100 to about 2000 mg.

6. The method of claim 1, wherein the arthritis is rheumatoid arthritis, osteoarthritis, psoriatic arthritis, ankylosing spondylitis, or juvenile rheumatoid arthritis.

7. A method of treating, inhibiting, or ameliorating rheumatoid arthritis (RA) in a subject suffering therefrom, comprising administering to a subject in need a therapeutic amount of an interleukin 1 (IL-1)-specific fusion protein comprising an IL-1 binding portion of the extracellular domain of human Il-1RAcP, an IL-1 binding portion of the extracellular domain of human IL-1RI, and a multimerizing component antagonist, wherein RA is treated, inhibited, or ameliorated, wherein the IL-1-specific fusion protein comprises the amino acid sequence of SEQ ID NO:10.

8. A method of treating, inhibiting, or ameliorating osteoarthritis (OA) in a subject suffering therefrom, comprising administering to a subject in need a therapeutic amount of an interleukin 1 (IL-1)-specific fusion protein comprising an IL-1 binding portion of the extracellular domain of human Il-1RAcP, an IL-1 binding portion of the extracellular domain of human IL-1RI, and a multimerizing component antagonist, wherein OA is treated, inhibited, or ameliorated, wherein the IL-1-specific fusion protein comprises the amino acid sequence of SEQ ID NO:10.

9. The method of claim 8, wherein administration is subcutaneous, intramuscular, intraarticular, or intravenous.

* * * * *

SEQUENCE LISTING

<160> NUMBER OF SEQ ID NOS: 26

<210> SEQ ID NO 1
<211> LENGTH: 2733
<212> TYPE: DNA
<213> ORGANISM: Artificial Sequence
<220> FEATURE:
<223> OTHER INFORMATION: Synthetic

<400> SEQUENCE: 1

```
atg gtg ctt ctg tgg tgt gta gtg agt ctc tac ttt tat gga atc ctg      48 caa agt gat gcc tca gaa cgc tgc gat gac tgg gga cta gac acc atg      96 agg caa atc caa gtg ttt gaa gat gag cca gct cgc atc aag tgc cca     144 ctc ttt gaa cac ttc ttg aaa ttc aac tac agc aca gcc cat tca gct     192 ggc ctt act ctg atc tgg tat tgg act agg cag gac cgg gac ctt gag     240 gag cca att aac ttc gcc ctc ccc gag aac cgc att agt aag gag aaa     288 gat gtg ctg tgg ttc cgg ccc act ctc ctc aat gac act ggc aac tat     336 acc tgc atg tta agg aac act aca tat tgc agc aaa gtt gca ttt ccc     384 ttg gaa gtt gtt caa aaa gac agc tgt ttc aat tcc ccc atg aaa ctc     432 cca gtg cat aaa ctg tat ata gaa tat ggc att cag agg atc act tgt     480 cca aat gta gat gga tat ttt cct tcc agt gtc aaa ccg act atc act     528 tgg tat atg ggc tgt tat aaa ata cag aat ttt aat aat gta ata ccc     576 gaa ggt atg aac ttg agt ttc ctc att gcc tta att tca aat aat gga     624 aat tac aca tgt gtt gtt aca tat cca gaa aat gga cgt acg ttt cat     672 ctc acc agg act ctg act gta aag gta gta ggc tct cca aaa aat gca     720 gtg ccc cct gtg atc cat tca cct aat gat cat gtg gtc tat gag aaa     768 gaa cca gga gag gag cta ctc att ccc tgt acg gtc tat ttt agt ttt     816 ctg atg gat tct cgc aat gag gtt tgg tgg acc att gat gga aaa aaa     864 cct gat gac atc act att gat gtc acc att aac gaa agt ata agt cat     912 agt aga aca gaa gat gaa aca aga act cag att ttg agc atc aag aaa     960 gtt acc tct gag gat ctc aag cgc agc tat gtc tgt cat gct aga agt    1008 gcc aaa ggc gaa gtt gcc aaa gca gcc aag gtg aag cag aaa gtg cca    1056 gct cca aga tac aca gtg tcc ggt ggc gcg cct atg ctg agc gag gct    1104 gat aaa tgc aag gaa cgt gaa gaa aaa ata att tta gtg tca tct gca    1152 aat gaa att gat gtt cgt ccc tgt cct ctt aac cca aat gaa cac aaa    1200 ggc act ata act tgg tat aag gat gac agc aag aca cct gta tct aca    1248 gaa caa gcc tcc agg att cat caa cac aaa gag aaa ctt tgg ttt gtt    1296
```

-continued

| | |
|---|---|
| cct gct aag gtg gag gat tca gga cat tac tat tgc gtg gta aga aat | 1344 |
| tca tct tac tgc ctc aga att aaa ata agt gca aaa ttt gtg gag aat | 1392 |
| gag cct aac tta tgt tat aat gca caa gcc ata ttt aag cag aaa cta | 1440 |
| ccc gtt gca gga gac gga gga ctt gtg tgc cct tat atg gag ttt ttt | 1488 |
| aaa aat gaa aat aat gag tta cct aaa tta cag tgg tat aag gat tgc | 1536 |
| aaa cct cta ctt ctt gac aat ata cac ttt agt gga gtc aaa gat agg | 1584 |
| ctc atc gtg atg aat gtg gct gaa aag cat aga ggg aac tat act tgt | 1632 |
| cat gca tcc tac aca tac ttg ggc aag caa tat cct att acc cgg gta | 1680 |
| ata gaa ttt att act cta gag gaa aac aaa ccc aca agg cct gtg att | 1728 |
| gtg agc cca gct aat gag aca atg gaa gta gac ttg gga tcc cag ata | 1776 |
| caa ttg atc tgt aat gtc acc ggc cag ttg agt gac att gct tac tgg | 1824 |
| aag tgg aat ggg tca gta att gat gaa gat gac cca gtg cta ggg gaa | 1872 |
| gac tat tac agt gtg gaa aat cct gca aac aaa aga agg agt acc ctc | 1920 |
| atc aca gtg ctt aat ata tcg gaa att gag agt aga ttt tat aaa cat | 1968 |
| cca ttt acc tgt ttt gcc aag aat aca cat ggt ata gat gca gca tat | 2016 |
| atc cag tta ata tat cca gtc act aat tcc gga gac aaa act cac aca | 2064 |
| tgc cca ccg tgc cca gca cct gaa ctc ctg ggg gga ccg tca gtc ttc | 2112 |
| ctc ttc ccc cca aaa ccc aag gac acc ctc atg atc tcc cgg acc cct | 2160 |
| gag gtc aca tgc gtg gtg gtg gac gtg agc cac gaa gac cct gag gtc | 2208 |
| aag ttc aac tgg tac gtg gac ggc gtg gag gtg cat aat gcc aag aca | 2256 |
| aag ccg cgg gag gag cag tac aac agc acg tac cgt gtg gtc agc gtc | 2304 |
| ctc acc gtc ctg cac cag gac tgg ctg aat ggc aag gag tac aag tgc | 2352 |
| aag gtc tcc aac aaa gcc ctc cca gcc ccc atc gag aaa acc atc tcc | 2400 |
| aaa gcc aaa ggg cag ccc cga gaa cca cag gtg tac acc ctg ccc cca | 2448 |
| tcc cgg gag gag atg acc aag aac cag gtc agc ctg acc tgc ctg gtc | 2496 |
| aaa ggc ttc tat ccc agc gac atc gcc gtg gag tgg gag agc aat ggg | 2544 |
| cag ccg gag aac aac tac aag acc acg cct ccc gtg ctg gac tcc gac | 2592 |
| ggc tcc ttc ttc ctc tat agc aag ctc acc gtg gac aag agc agg tgg | 2640 |
| cag cag ggg aac gtc ttc tca tgc tcc gtg atg cat gag gct ctg cac | 2688 |
| aac cac tac acg cag aag agc ctc tcc ctg tct ccg ggt aaa | 2730 |
| tga | 2733 |

<210> SEQ ID NO 2
<211> LENGTH: 910
<212> TYPE: PRT
<213> ORGANISM: Artificial Sequence
<220> FEATURE:
<223> OTHER INFORMATION: Synthetic

<400> SEQUENCE: 2

Met Val Leu Leu Trp Cys Val Val Ser Leu Tyr Phe Tyr Gly Ile Leu
 1               5                  10                  15

Gln Ser Asp Ala Ser Glu Arg Cys Asp Asp Trp Gly Leu Asp Thr Met
            20                  25                  30

-continued

```
Arg Gln Ile Gln Val Phe Glu Asp Glu Pro Ala Arg Ile Lys Cys Pro
            35                  40                  45

Leu Phe Glu His Phe Leu Lys Phe Asn Tyr Ser Thr Ala His Ser Ala
 50                  55                  60

Gly Leu Thr Leu Ile Trp Tyr Trp Thr Arg Gln Asp Arg Asp Leu Glu
 65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
                100                 105                 110

Thr Cys Met Leu Arg Asn Thr Thr Tyr Cys Ser Lys Val Ala Phe Pro
                115                 120                 125

Leu Glu Val Val Gln Lys Asp Ser Cys Phe Asn Ser Pro Met Lys Leu
        130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
                180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
        210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
                260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
        290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
                340                 345                 350

Ala Pro Arg Tyr Thr Val Ser Gly Gly Ala Pro Met Leu Ser Glu Ala
        355                 360                 365

Asp Lys Cys Lys Glu Arg Glu Glu Lys Ile Ile Leu Val Ser Ser Ala
        370                 375                 380

Asn Glu Ile Asp Val Arg Pro Cys Pro Leu Asn Pro Asn Glu His Lys
385                 390                 395                 400

Gly Thr Ile Thr Trp Tyr Lys Asp Asp Ser Lys Thr Pro Val Ser Thr
                405                 410                 415

Glu Gln Ala Ser Arg Ile His Gln His Lys Glu Lys Leu Trp Phe Val
                420                 425                 430

Pro Ala Lys Val Glu Asp Ser Gly His Tyr Tyr Cys Val Val Arg Asn
        435                 440                 445

Ser Ser Tyr Cys Leu Arg Ile Lys Ile Ser Ala Lys Phe Val Glu Asn
```

```
            450                 455                 460
Glu Pro Asn Leu Cys Tyr Asn Ala Gln Ala Ile Phe Lys Gln Lys Leu
465                 470                 475                 480

Pro Val Ala Gly Asp Gly Gly Leu Val Cys Pro Tyr Met Glu Phe Phe
                485                 490                 495

Lys Asn Glu Asn Asn Glu Leu Pro Lys Leu Gln Trp Tyr Lys Asp Cys
                500                 505                 510

Lys Pro Leu Leu Leu Asp Asn Ile His Phe Ser Gly Val Lys Asp Arg
            515                 520                 525

Leu Ile Val Met Asn Val Ala Glu Lys His Arg Gly Asn Tyr Thr Cys
            530                 535                 540

His Ala Ser Tyr Thr Tyr Leu Gly Lys Gln Tyr Pro Ile Thr Arg Val
545                 550                 555                 560

Ile Glu Phe Ile Thr Leu Glu Glu Asn Lys Pro Thr Arg Pro Val Ile
                565                 570                 575

Val Ser Pro Ala Asn Glu Thr Met Glu Val Asp Leu Gly Ser Gln Ile
                580                 585                 590

Gln Leu Ile Cys Asn Val Thr Gly Gln Leu Ser Asp Ile Ala Tyr Trp
            595                 600                 605

Lys Trp Asn Gly Ser Val Ile Asp Glu Asp Pro Val Leu Gly Glu
            610                 615                 620

Asp Tyr Tyr Ser Val Glu Asn Pro Ala Asn Lys Arg Arg Ser Thr Leu
625                 630                 635                 640

Ile Thr Val Leu Asn Ile Ser Glu Ile Glu Ser Arg Phe Tyr Lys His
                645                 650                 655

Pro Phe Thr Cys Phe Ala Lys Asn Thr His Gly Ile Asp Ala Ala Tyr
                660                 665                 670

Ile Gln Leu Ile Tyr Pro Val Thr Asn Ser Gly Asp Lys Thr His Thr
            675                 680                 685

Cys Pro Pro Cys Pro Ala Pro Glu Leu Leu Gly Gly Pro Ser Val Phe
            690                 695                 700

Leu Phe Pro Pro Lys Pro Lys Asp Thr Leu Met Ile Ser Arg Thr Pro
705                 710                 715                 720

Glu Val Thr Cys Val Val Val Asp Val Ser His Glu Asp Pro Glu Val
                725                 730                 735

Lys Phe Asn Trp Tyr Val Asp Gly Val Glu Val His Asn Ala Lys Thr
                740                 745                 750

Lys Pro Arg Glu Glu Gln Tyr Asn Ser Thr Tyr Arg Val Val Ser Val
            755                 760                 765

Leu Thr Val Leu His Gln Asp Trp Leu Asn Gly Lys Glu Tyr Lys Cys
770                 775                 780

Lys Val Ser Asn Lys Ala Leu Pro Ala Pro Ile Glu Lys Thr Ile Ser
785                 790                 795                 800

Lys Ala Lys Gly Gln Pro Arg Glu Pro Gln Val Tyr Thr Leu Pro Pro
                805                 810                 815

Ser Arg Glu Glu Met Thr Lys Asn Gln Val Ser Leu Thr Cys Leu Val
                820                 825                 830

Lys Gly Phe Tyr Pro Ser Asp Ile Ala Val Glu Trp Glu Ser Asn Gly
            835                 840                 845

Gln Pro Glu Asn Asn Tyr Lys Thr Thr Pro Pro Val Leu Asp Ser Asp
            850                 855                 860

Gly Ser Phe Phe Leu Tyr Ser Lys Leu Thr Val Asp Lys Ser Arg Trp
865                 870                 875                 880
```

Gln Gln Gly Asn Val Phe Ser Cys Ser Val Met His Glu Ala Leu His
                885                 890                 895

Asn His Tyr Thr Gln Lys Ser Leu Ser Leu Ser Pro Gly Lys
            900                 905                 910

<210> SEQ ID NO 3
<211> LENGTH: 2703
<212> TYPE: DNA
<213> ORGANISM: Artificial Sequence
<220> FEATURE:
<223> OTHER INFORMATION: Synthetic

<400> SEQUENCE: 3

| | | | | | |
|---|---|---|---|---|---|
| atggtgttac | tcagacttat | ttgtttcata | gctctactga | tttcttctct | ggaggctgat | 60 |
| aaatgcaagg | aacgtgaaga | aaaataatt | ttagtgtcat | ctgcaaatga | aattgatgtt | 120 |
| cgtccctgtc | ctcttaaccc | aaatgaacac | aaaggcacta | aacttggta | taaggatgac | 180 |
| agcaagacac | ctgtatctac | agaacaagcc | tccaggattc | atcaacacaa | agagaaactt | 240 |
| tggtttgttc | ctgctaaggt | ggaggattca | ggacattact | attgcgtggt | aagaaattca | 300 |
| tcttactgcc | tcagaattaa | aataagtgca | aaatttgtgg | agaatgagcc | taacttatgt | 360 |
| tataatgcac | aagccatatt | taagcagaaa | ctacccgttg | caggagacgg | aggacttgtg | 420 |
| tgccccttata | tggagttttt | taaaaatgaa | aataatgagt | acctaaatt | acagtggtat | 480 |
| aaggattgca | aacctctact | tcttgacaat | atacactta | gtggagtcaa | agataggctc | 540 |
| atcgtgatga | atgtggctga | aaagcataga | gggaactata | cttgtcatgc | atcctacaca | 600 |
| tacttgggca | agcaatatcc | tattacccgg | gtaatagaat | ttattactct | agaggaaaac | 660 |
| aaacccacaa | ggcctgtgat | tgtgagccca | gctaatgaga | caatgaagt | agacttggga | 720 |
| tcccagatac | aattgatctg | taatgtcacc | ggccagttga | gtgacattgc | ttactggaag | 780 |
| tggaatgggt | cagtaattga | tgaagatgac | ccagtgctag | gggaagacta | ttacagtgtg | 840 |
| gaaaatcctg | caaacaaaag | aaggagtacc | ctcatcacag | tgcttaatat | atcggaaatt | 900 |
| gagagtagat | tttataaaca | tccatttacc | tgttttgcca | agaatacaca | tggtatagat | 960 |
| gcagcatata | tccagttaat | atatccagtc | actaattcag | aacgctgcga | tgactgggga | 1020 |
| ctagacacca | tgaggcaaat | tccaagtgttt | gaagatgagc | cagctcgcat | caagtgccca | 1080 |
| ctctttgaac | acttcttgaa | attcaactac | agcacagccc | attcagctgg | ccttactctg | 1140 |
| atctggtatt | ggactaggca | ggaccgggac | cttgaggagc | caattaactt | ccgcctcccc | 1200 |
| gagaaccgca | ttagtaagga | aaagatgtg | ctgtggttcc | ggcccactct | cctcaatgac | 1260 |
| actggcaact | ataccctgcat | gttaaggaac | actacatatt | gcagcaaagt | tgcatttccc | 1320 |
| ttggaagttg | ttcaaaaaga | cagctgtttc | aattcccca | tgaaactccc | agtgcataaa | 1380 |
| ctgtatatag | aatatggcat | tcagaggatc | acttgtccaa | atgtagatgg | atattttcct | 1440 |
| tccagtgtca | aaccgactat | cacttggtat | atgggctgtt | ataaaataca | gaattttaat | 1500 |
| aatgtaatac | ccgaaggtat | gaacttgagt | ttcctcattg | ccttaattc | aaataatgga | 1560 |
| aattacacat | gtgttgttac | atatccagaa | aatggacgta | cgtttcatct | caccaggact | 1620 |
| ctgactgtaa | aggtagtagg | ctctccaaaa | aatgcagtgc | ccctgtgat | ccattcacct | 1680 |
| aatgatcatg | tggtctatga | aaagaaacca | ggagaggagc | tactcattcc | ctgtacggtc | 1740 |
| tattttagtt | ttctgatgga | ttctcgcaat | gaggtttggt | ggaccattga | tggaaaaaaa | 1800 |
| cctgatgaca | tcactattga | tgtcaccatt | aacgaaagta | taagtcatag | tagaacgaaa | 1860 |

-continued

```
gatgaaacaa gaactcagat tttgagcatc aagaaagtta cctctgagga tctcaagcgc    1920
agctatgtct gtcatgctag aagtgccaaa ggcgaagttg ccaaagcagc caaggtgaag    1980
cagaaagtgc cagctccaag atacacagtg gaatccggag acaaaactca cacatgccca    2040
ccgtgcccag cacctgaact cctgggggga ccgtcagtct tcctcttccc cccaaaaccc    2100
aaggacaccc tcatgatctc ccggacccct gaggtcacat gcgtggtggt ggacgtgagc    2160
cacgaagacc ctgaggtcaa gttcaactgg tacgtggacg gcgtggaggt gcataatgcc    2220
aagacaaagc cgcgggagga gcagtacaac agcacgtacc gtgtggtcag cgtcctcacc    2280
gtcctgcacc aggactggct gaatggcaag gagtacaagt gcaaggtctc caacaaagcc    2340
ctcccagccc ccatcgagaa aaccatctcc aaagccaaag gcagccccg agaaccacag     2400 gtgtacaccc tgcccccatc ccgggaggag atgaccaaga accaggtcag cctgacctgc    2460
ctggtcaaag gcttctatcc cagcgacatc gccgtggagt gggagagcaa tgggcagccg    2520
gagaacaact acaagaccac gcctcccgtg ctggactccg acggctcctt cttcctctat    2580
agcaagctca ccgtggacaa gagcaggtgg cagcagggga acgtcttctc atgctccgtg    2640
atgcatgagg ctctgcacaa ccactacacg cagaagagcc tctccctgtc tccgggtaaa    2700
tga                                                                 2703

<210> SEQ ID NO 4
<211> LENGTH: 900
<212> TYPE: PRT
<213> ORGANISM: Artificial Sequence
<220> FEATURE:
<223> OTHER INFORMATION: Synthetic

<400> SEQUENCE: 4

Met Val Leu Leu Arg Leu Ile Cys Phe Ile Ala Leu Leu Ile Ser Ser
 1               5                  10                  15

Leu Glu Ala Asp Lys Cys Lys Glu Arg Glu Glu Lys Ile Ile Leu Val
                20                  25                  30

Ser Ser Ala Asn Glu Ile Asp Val Arg Pro Cys Pro Leu Asn Pro Asn
            35                  40                  45

Glu His Lys Gly Thr Ile Thr Trp Tyr Lys Asp Asp Ser Lys Thr Pro
        50                  55                  60

Val Ser Thr Glu Gln Ala Ser Arg Ile His Gln His Lys Glu Lys Leu
    65                  70                  75                  80

Trp Phe Val Pro Ala Lys Val Glu Asp Ser Gly His Tyr Tyr Cys Val
                85                  90                  95

Val Arg Asn Ser Ser Tyr Cys Leu Arg Ile Lys Ile Ser Ala Lys Phe
               100                 105                 110

Val Glu Asn Glu Pro Asn Leu Cys Tyr Asn Ala Gln Ala Ile Phe Lys
           115                 120                 125

Gln Lys Leu Pro Val Ala Gly Asp Gly Gly Leu Val Cys Pro Tyr Met
       130                 135                 140

Glu Phe Phe Lys Asn Glu Asn Asn Glu Leu Pro Lys Leu Gln Trp Tyr
145                 150                 155                 160

Lys Asp Cys Lys Pro Leu Leu Leu Asp Asn Ile His Phe Ser Gly Val
                165                 170                 175

Lys Asp Arg Leu Ile Val Met Asn Val Ala Glu Lys His Arg Gly Asn
            180                 185                 190

Tyr Thr Cys His Ala Ser Tyr Thr Tyr Leu Gly Lys Gln Tyr Pro Ile
        195                 200                 205
```

-continued

```
Thr Arg Val Ile Glu Phe Ile Thr Leu Glu Glu Asn Lys Pro Thr Arg
    210                 215                 220
Pro Val Ile Val Ser Pro Ala Asn Glu Thr Met Glu Val Asp Leu Gly
225                 230                 235                 240
Ser Gln Ile Gln Leu Ile Cys Asn Val Thr Gly Gln Leu Ser Asp Ile
                    245                 250                 255
Ala Tyr Trp Lys Trp Asn Gly Ser Val Ile Asp Glu Asp Asp Pro Val
            260                 265                 270
Leu Gly Glu Asp Tyr Tyr Ser Val Glu Asn Pro Ala Asn Lys Arg Arg
        275                 280                 285
Ser Thr Leu Ile Thr Val Leu Asn Ile Ser Glu Ile Glu Ser Arg Phe
    290                 295                 300
Tyr Lys His Pro Phe Thr Cys Phe Ala Lys Asn Thr His Gly Ile Asp
305                 310                 315                 320
Ala Ala Tyr Ile Gln Leu Ile Tyr Pro Val Thr Asn Ser Glu Arg Cys
                    325                 330                 335
Asp Asp Trp Gly Leu Asp Thr Met Arg Gln Ile Gln Val Phe Glu Asp
            340                 345                 350
Glu Pro Ala Arg Ile Lys Cys Pro Leu Phe His Phe Leu Lys Phe
        355                 360                 365
Asn Tyr Ser Thr Ala His Ser Ala Gly Leu Thr Leu Ile Trp Tyr Trp
370                 375                 380
Thr Arg Gln Asp Arg Asp Leu Glu Glu Pro Ile Asn Phe Arg Leu Pro
385                 390                 395                 400
Glu Asn Arg Ile Ser Lys Glu Lys Asp Val Leu Trp Phe Arg Pro Thr
                    405                 410                 415
Leu Leu Asn Asp Thr Gly Asn Tyr Thr Cys Met Leu Arg Asn Thr Thr
            420                 425                 430
Tyr Cys Ser Lys Val Ala Phe Pro Leu Glu Val Val Gln Lys Asp Ser
        435                 440                 445
Cys Phe Asn Ser Pro Met Lys Leu Pro Val His Lys Leu Tyr Ile Glu
    450                 455                 460
Tyr Gly Ile Gln Arg Ile Thr Cys Pro Asn Val Asp Gly Tyr Phe Pro
465                 470                 475                 480
Ser Ser Val Lys Pro Thr Ile Thr Trp Tyr Met Gly Cys Tyr Lys Ile
                    485                 490                 495
Gln Asn Phe Asn Asn Val Ile Pro Glu Gly Met Asn Leu Ser Phe Leu
            500                 505                 510
Ile Ala Leu Ile Ser Asn Asn Gly Asn Tyr Thr Cys Val Val Thr Tyr
        515                 520                 525
Pro Glu Asn Gly Arg Thr Phe His Leu Thr Arg Thr Leu Thr Val Lys
    530                 535                 540
Val Val Gly Ser Pro Lys Asn Ala Val Pro Pro Val Ile His Ser Pro
545                 550                 555                 560
Asn Asp His Val Val Tyr Glu Lys Glu Pro Gly Glu Glu Leu Leu Ile
                    565                 570                 575
Pro Cys Thr Val Tyr Phe Ser Phe Leu Met Asp Ser Arg Asn Glu Val
            580                 585                 590
Trp Trp Thr Ile Asp Gly Lys Lys Pro Asp Asp Ile Thr Ile Asp Val
        595                 600                 605
Thr Ile Asn Glu Ser Ile Ser His Ser Arg Thr Glu Asp Glu Thr Arg
    610                 615                 620
Thr Gln Ile Leu Ser Ile Lys Lys Val Thr Ser Glu Asp Leu Lys Arg
```

```
                625                 630                 635                 640
Ser Tyr Val Cys His Ala Arg Ser Ala Lys Gly Glu Val Ala Lys Ala
                    645                 650                 655
Ala Lys Val Lys Gln Lys Val Pro Ala Pro Arg Tyr Thr Val Glu Ser
                    660                 665                 670
Gly Asp Lys Thr His Thr Cys Pro Pro Cys Pro Ala Pro Glu Leu Leu
                    675                 680                 685
Gly Gly Pro Ser Val Phe Leu Phe Pro Pro Lys Pro Lys Asp Thr Leu
                    690                 695                 700
Met Ile Ser Arg Thr Pro Glu Val Thr Cys Val Val Val Asp Val Ser
705                 710                 715                 720
His Glu Asp Pro Glu Val Lys Phe Asn Trp Tyr Val Asp Gly Val Glu
                    725                 730                 735
Val His Asn Ala Lys Thr Lys Pro Arg Glu Glu Gln Tyr Asn Ser Thr
                    740                 745                 750
Tyr Arg Val Val Ser Val Leu Thr Val Leu His Gln Asp Trp Leu Asn
                    755                 760                 765
Gly Lys Glu Tyr Lys Cys Lys Val Ser Asn Lys Ala Leu Pro Ala Pro
        770                 775                 780
Ile Glu Lys Thr Ile Ser Lys Ala Lys Gly Gln Pro Arg Glu Pro Gln
785                 790                 795                 800
Val Tyr Thr Leu Pro Pro Ser Arg Glu Glu Met Thr Lys Asn Gln Val
                    805                 810                 815
Ser Leu Thr Cys Leu Val Lys Gly Phe Tyr Pro Ser Asp Ile Ala Val
                    820                 825                 830
Glu Trp Glu Ser Asn Gly Gln Pro Glu Asn Asn Tyr Lys Thr Thr Pro
            835                 840                 845
Pro Val Leu Asp Ser Asp Gly Ser Phe Phe Leu Tyr Ser Lys Leu Thr
        850                 855                 860
Val Asp Lys Ser Arg Trp Gln Gln Gly Asn Val Phe Ser Cys Ser Val
865                 870                 875                 880
Met His Glu Ala Leu His Asn His Tyr Thr Gln Lys Ser Leu Ser Leu
                    885                 890                 895
Ser Pro Gly Lys
            900

<210> SEQ ID NO 5
<211> LENGTH: 2709
<212> TYPE: DNA
<213> ORGANISM: Artificial Sequence
<220> FEATURE:
<223> OTHER INFORMATION: Synthetic

<400> SEQUENCE: 5
atggtgttac tcagacttat ttgtttcata gctctactga tttcttctct ggaggctgat      60
aaatgcaagg aacgtgaaga aaaataatt  ttagtgtcat ctgcaaatga aattgatgtt     120
cgtccctgtc ctcttaaccc aaatgaacac aaaggcacta aacttggta taaggatgac      180 agcaagacac ctgtatctac agaacaagcc tccaggattc atcaacacaa agagaaactt     240
tggtttgttc ctgctaaggt ggaggattca ggacattact attgcgtggt aagaaattca     300
tcttactgcc tcagaattaa aataagtgca aatttgtgg agaatgagcc taacttatgt     360
tataatgcac aagccatatt taagcagaaa ctacccgttg caggagacgg aggcttgtg     420 tgcccttata tggagttttt taaaaatgaa ataatgagt tacctaaatt acagtggtat     480
```

| | |
|---|---|
| aaggattgca aacctctact tcttgacaat atacacttta gtggagtcaa agataggctc | 540 |
| atcgtgatga atgtggctga aaagcataga gggaactata cttgtcatgc atcctacaca | 600 |
| tacttgggca agcaatatcc tattacccgg gtaatagaat ttattactct agaggaaaac | 660 |
| aaacccacaa ggcctgtgat tgtgagccca gctaatgaga caatggaagt agacttggga | 720 |
| tcccagatac aattgatctg taatgtcacc ggccagttga gtgacattgc ttactggaag | 780 |
| tggaatgggt cagtaattga tgaagatgac ccagtgctag gggaagacta ttacagtgtg | 840 |
| gaaaatcctg caaacaaaag aaggagtacc ctcatcacag tgcttaatat atcggaaatt | 900 |
| gagagtagat tttataaaca tccatttacc tgttttgcca agaatacaca tggtatagat | 960 |
| gcagcatata tccagttaat atatccagtc actaattcag aacgctgcga tgactgggga | 1020 |
| ctagacacca tgaggcaaat ccaagtgttt gaagatgagc cagctcgcat caagtgccca | 1080 |
| ctctttgaac acttcttgaa attcaactac agcacagccc attcagctgg ccttactctg | 1140 |
| atctggtatt ggactaggca ggaccgggac cttgaggagc caattaactt ccgcctcccc | 1200 |
| gagaaccgca ttagtaagga aaagatgtg ctgtggttcc ggcccactct cctcaatgac | 1260 |
| actggcaact atacctgcat gttaaggaac actacatatt gcagcaaagt tgcatttccc | 1320 |
| ttggaagttg ttcaaaaaga cagctgtttc aattccccca tgaaactccc agtgcataaa | 1380 |
| ctgtatatag aatatggcat tcagaggatc acttgtccaa atgtagatgg atattttcct | 1440 |
| tccagtgtca aaccgactat cacttggtat atgggctgtt ataaaataca gaattttaat | 1500 |
| aatgtaatac ccgaaggtat gaacttgagt ttcctcattg ccttaatttc aaataatgga | 1560 |
| aattacacat gtgttgttac atatccagaa aatggacgta cgtttcatct caccaggact | 1620 |
| ctgactgtaa aggtagtagg ctctccaaaa aatgcagtgc cccctgtgat ccattcacct | 1680 |
| aatgatcatg tggtctatga gaaagaacca ggagaggagc tactcattcc ctgtacggtc | 1740 |
| tattttagtt ttctgatgga ttctcgcaat gaggtttggt ggaccattga tggaaaaaaa | 1800 |
| cctgatgaca tcactattga tgtcaccatt aacgaaagta taagtcatag tagaacagaa | 1860 |
| gatgaaacaa gaactcagat tttgagcatc aagaaagtta cctctgagga tctcaagcgc | 1920 |
| agctatgtct gtcatgctag aagtgccaaa ggcgaagttg ccaaagcagc caaggtgaag | 1980 |
| cagaaagtgc cagctccaag atacacagtg aatccggag agtccaaata cggtccgcca | 2040 |
| tgcccatcat gcccagcacc tgagttcctg gggggaccat cagtcttcct gttccccca | 2100 |
| aaacccaagg acactctcat gatctcccgg acccctgagg tcacgtgcgt ggtggtggac | 2160 |
| gtgagccagg aagaccccga ggtccagttc aactggtacg tggatggcgt ggaggtgcat | 2220 |
| aatgccaaga caaagccgcg ggaggagcag ttcaacagca cgtaccgtgt ggtcagcgtc | 2280 |
| ctcaccgtcc tgcaccagga ctggctgaac ggcaaggagt acaagtgcaa ggtctccaac | 2340 |
| aaaggcctcc cgtcctccat cgagaaaacc atctccaaag ccaaagggca gccccgagag | 2400 |
| ccacaggtgt acaccctgcc cccatcccag gaggagatga ccaagaacca ggtcagcctg | 2460 |
| acctgcctgg tcaaaggctt ctaccccagc gacatcgccg tggagtggga gagcaatggg | 2520 |
| cagccggaga caactacaa gaccacgcct cccgtgctgg actccgacgg ctccttcttc | 2580 |
| ctctacagca ggctaaccgt ggacaagagc aggtggcagg aggggaatgt cttctcatgc | 2640 |
| tccgtgatgc atgaggctct gcacaaccac tacacacaga gagcctctc cctgtctctg | 2700 |
| ggtaaatga | 2709 |

<210> SEQ ID NO 6
<211> LENGTH: 902

<212> TYPE: PRT
<213> ORGANISM: Artificial Sequence
<220> FEATURE:
<223> OTHER INFORMATION: Synthetic

<400> SEQUENCE: 6

```
Met Val Leu Leu Arg Leu Ile Cys Phe Ile Ala Leu Leu Ile Ser Ser
 1               5                  10                  15

Leu Glu Ala Asp Lys Cys Lys Glu Arg Glu Lys Ile Ile Leu Val
             20                  25                  30

Ser Ser Ala Asn Glu Ile Asp Val Arg Pro Cys Pro Leu Asn Pro Asn
             35                  40                  45

Glu His Lys Gly Thr Ile Thr Trp Tyr Lys Asp Asp Ser Lys Thr Pro
         50                  55                  60

Val Ser Thr Glu Gln Ala Ser Arg Ile His Gln His Lys Glu Lys Leu
 65                  70                  75                  80

Trp Phe Val Pro Ala Lys Val Glu Asp Ser Gly His Tyr Tyr Cys Val
                 85                  90                  95

Val Arg Asn Ser Ser Tyr Cys Leu Arg Ile Lys Ile Ser Ala Lys Phe
            100                 105                 110

Val Glu Asn Glu Pro Asn Leu Cys Tyr Asn Ala Gln Ala Ile Phe Lys
            115                 120                 125

Gln Lys Leu Pro Val Ala Gly Asp Gly Gly Leu Val Cys Pro Tyr Met
130                 135                 140

Glu Phe Phe Lys Asn Glu Asn Asn Glu Leu Pro Lys Leu Gln Trp Tyr
145                 150                 155                 160

Lys Asp Cys Lys Pro Leu Leu Leu Asp Asn Ile His Phe Ser Gly Val
                165                 170                 175

Lys Asp Arg Leu Ile Val Met Asn Val Ala Glu Lys His Arg Gly Asn
            180                 185                 190

Tyr Thr Cys His Ala Ser Tyr Thr Tyr Leu Gly Lys Gln Tyr Pro Ile
            195                 200                 205

Thr Arg Val Ile Glu Phe Ile Thr Leu Glu Glu Asn Lys Pro Thr Arg
            210                 215                 220

Pro Val Ile Val Ser Pro Ala Asn Glu Thr Met Glu Val Asp Leu Gly
225                 230                 235                 240

Ser Gln Ile Gln Leu Ile Cys Asn Val Thr Gly Gln Leu Ser Asp Ile
                245                 250                 255

Ala Tyr Trp Lys Trp Asn Gly Ser Val Ile Asp Glu Asp Pro Val
            260                 265                 270

Leu Gly Glu Asp Tyr Tyr Ser Val Glu Asn Pro Ala Asn Lys Arg Arg
            275                 280                 285

Ser Thr Leu Ile Thr Val Leu Asn Ile Ser Glu Ile Glu Ser Arg Phe
290                 295                 300

Tyr Lys His Pro Phe Thr Cys Phe Ala Lys Asn Thr His Gly Ile Asp
305                 310                 315                 320

Ala Ala Tyr Ile Gln Leu Ile Tyr Pro Val Thr Asn Ser Glu Arg Cys
                325                 330                 335

Asp Asp Trp Gly Leu Asp Thr Met Arg Gln Ile Gln Val Phe Glu Asp
            340                 345                 350

Glu Pro Ala Arg Ile Lys Cys Pro Leu Phe Glu His Phe Leu Lys Phe
            355                 360                 365

Asn Tyr Ser Thr Ala His Ser Ala Gly Leu Thr Leu Ile Trp Tyr Trp
            370                 375                 380
```

-continued

```
Thr Arg Gln Asp Arg Asp Leu Glu Glu Pro Ile Asn Phe Arg Leu Pro
385                 390                 395                 400

Glu Asn Arg Ile Ser Lys Glu Lys Asp Val Leu Trp Phe Arg Pro Thr
            405                 410                 415

Leu Leu Asn Asp Thr Gly Asn Tyr Thr Cys Met Leu Arg Asn Thr Thr
        420                 425                 430

Tyr Cys Ser Lys Val Ala Phe Pro Leu Glu Val Val Gln Lys Asp Ser
    435                 440                 445

Cys Phe Asn Ser Pro Met Lys Leu Pro Val His Lys Leu Tyr Ile Glu
    450                 455                 460

Tyr Gly Ile Gln Arg Ile Thr Cys Pro Asn Val Asp Gly Tyr Phe Pro
465                 470                 475                 480

Ser Ser Val Lys Pro Thr Ile Thr Trp Tyr Met Gly Cys Tyr Lys Ile
                485                 490                 495

Gln Asn Phe Asn Asn Val Ile Pro Glu Gly Met Asn Leu Ser Phe Leu
                500                 505                 510

Ile Ala Leu Ile Ser Asn Asn Gly Asn Tyr Thr Cys Val Val Thr Tyr
            515                 520                 525

Pro Glu Asn Gly Arg Thr Phe His Leu Thr Arg Thr Leu Thr Val Lys
    530                 535                 540

Val Val Gly Ser Pro Lys Asn Ala Val Pro Pro Val Ile His Ser Pro
545                 550                 555                 560

Asn Asp His Val Val Tyr Glu Lys Glu Pro Gly Glu Glu Leu Leu Ile
                565                 570                 575

Pro Cys Thr Val Tyr Phe Ser Phe Leu Met Asp Ser Arg Asn Glu Val
                580                 585                 590

Trp Trp Thr Ile Asp Gly Lys Lys Pro Asp Asp Ile Thr Ile Asp Val
            595                 600                 605

Thr Ile Asn Glu Ser Ile Ser His Ser Arg Thr Glu Asp Glu Thr Arg
610                 615                 620

Thr Gln Ile Leu Ser Ile Lys Lys Val Thr Ser Glu Asp Leu Lys Arg
625                 630                 635                 640

Ser Tyr Val Cys His Ala Arg Ser Ala Lys Gly Glu Val Ala Lys Ala
                645                 650                 655

Ala Lys Val Lys Gln Lys Val Pro Ala Pro Arg Tyr Thr Val Glu Ser
            660                 665                 670

Gly Glu Ser Lys Tyr Gly Pro Pro Cys Pro Ser Cys Pro Ala Pro Glu
        675                 680                 685

Phe Leu Gly Gly Pro Ser Val Phe Leu Phe Pro Pro Lys Pro Lys Asp
    690                 695                 700

Thr Leu Met Ile Ser Arg Thr Pro Glu Val Thr Cys Val Val Val Asp
705                 710                 715                 720

Val Ser Gln Glu Asp Pro Glu Val Gln Phe Asn Trp Tyr Val Asp Gly
                725                 730                 735

Val Glu Val His Asn Ala Lys Thr Lys Pro Arg Glu Glu Gln Phe Asn
            740                 745                 750

Ser Thr Tyr Arg Val Val Ser Val Leu Thr Val Leu His Gln Asp Trp
        755                 760                 765

Leu Asn Gly Lys Glu Tyr Lys Cys Lys Val Ser Asn Lys Gly Leu Pro
    770                 775                 780

Ser Ser Ile Glu Lys Thr Ile Ser Lys Ala Lys Gly Gln Pro Arg Glu
785                 790                 795                 800

Pro Gln Val Tyr Thr Leu Pro Pro Ser Gln Glu Glu Met Thr Lys Asn
```

```
                    805                 810                 815
Gln Val Ser Leu Thr Cys Leu Val Lys Gly Phe Tyr Pro Ser Asp Ile
            820                 825                 830

Ala Val Glu Trp Glu Ser Asn Gly Gln Pro Glu Asn Asn Tyr Lys Thr
            835                 840                 845

Thr Pro Pro Val Leu Asp Ser Asp Gly Ser Phe Phe Leu Tyr Ser Arg
        850                 855                 860

Leu Thr Val Asp Lys Ser Arg Trp Gln Glu Gly Asn Val Phe Ser Cys
865                 870                 875                 880

Ser Val Met His Glu Ala Leu His Asn His Tyr Thr Gln Lys Ser Leu
                885                 890                 895

Ser Leu Ser Leu Gly Lys
            900

<210> SEQ ID NO 7
<211> LENGTH: 2709
<212> TYPE: DNA
<213> ORGANISM: Artificial Sequence
<220> FEATURE:
<223> OTHER INFORMATION: Synthetic

<400> SEQUENCE: 7
atggtgttac tcagacttat ttgtttcata gctctactga tttcttctct ggaggctgat      60
aaatgcaagg aacgtgaaga aaaataatt ttagtgtcat ctgcaaatga aattgatgtt     120
cgtccctgtc ctcttaaccc aaatgaacac aaaggcacta aacttggta taaggatgac     180 agcaagacac ctgtatctac agaacaagcc tccaggattc atcaacacaa agagaaactt     240
tggtttgttc ctgctaaggt ggaggattca ggacattact attgcgtggt aagaaattca     300
tcttactgcc tcagaattaa aataagtgca aaatttgtgg agaatgagcc taacttatgt     360
tataatgcac aagccatatt taagcagaaa ctacccgttg caggagacgg aggacttgtg     420
tgcccttata tggagttttt taaaaatgaa ataatgagt tacctaaatt acagtggtat     480
aaggattgca aacctctact tcttgacaat atacacttta gtggagtcaa agataggctc     540
atcgtgatga atgtggctga aaagcataga gggaactata cttgtcatgc atcctacaca     600
tacttgggca agcaatatcc tattacccgg gtaatagaat ttattactct agaggaaaac     660
aaacccacaa ggcctgtgat tgtgagccca gctaatgaga caatggaagt agacttggga     720
tcccagatac aattgatctg taatgtcacc ggccagttga gtgacattgc ttactggaag     780
tggaatgggt cagtaattga tgaagatgac ccagtgctag gggaagacta ttacagtgtg     840
gaaaatcctg caaacaaaag aaggagtacc ctcatcacag tgcttaatat atcggaaatt     900
gagagtagat tttataaaca tccatttacc tgttttgcca agaatacaca tggtatagat     960
gcagcatata tccagttaat atatccagtc actaattcag aacgctgcga tgactgggga    1020
ctagacacca tgaggcaaat ccaagtgttt gaagatgagc agctcgcat caagtgccca    1080 ctctttgaac acttcttgaa attcaactac agcacagccc attcagctgg ccttactctg    1140
atctggtatt ggactaggca ggaccgggac cttgaggagc caattaactt ccgcctcccc    1200
gagaaccgca ttagtaagga aaagatgtg ctgtggttcc ggcccactct cctcaatgac    1260
actggcaact atacctgcat gttaaggaac actacatatt gcagcaaagt tgcatttccc    1320
ttggaagttg ttcaaaaaga cagctgtttc aattccccca tgaaactccc agtgcataaa    1380
ctgtatatag aatatggcat tcagaggatc acttgtccaa atgtagatgg atattttcct    1440
tccagtgtca aaccgactat cacttggtat atgggctgtt ataaaataca gaattttaat    1500
```

-continued

```
aatgtaatac ccgaaggtat gaacttgagt ttcctcattg ccttaatttc aaataatgga    1560
aattacacat gtgttgttac atatccagaa aatggacgta cgtttcatct caccaggact    1620
ctgactgtaa aggtagtagg ctctccaaaa aatgcagtgc ccctgtgat ccattcacct    1680 aatgatcatg tggtctatga gaaagaacca ggagaggagc tactcattcc ctgtacggtc    1740
tattttagtt ttctgatgga ttctcgcaat gaggtttggt ggaccattga tggaaaaaaa    1800
cctgatgaca tcactattga tgtcaccatt aacgaaagta taagtcatag tagaacagaa    1860
gatgaaacaa gaactcagat tttgagcatc aagaaagtta cctctgagga tctcaagcgc    1920
agctatgtct gtcatgctag aagtgccaaa ggcgaagttg ccaaagcagc caaggtgaag    1980
cagaaagtgc cagctccaag atacacagtg gaatccggag agtccaaata cggtccgcca    2040
tgcccaccat gcccagcacc tgagttcctg ggggaccat cagtcttcct gttccccca    2100 aaacccaagg acactctcat gatctcccgg acccctgagg tcacgtgcgt ggtggtggac    2160
gtgagccagg aagaccccga ggtccagttc aactggtacg tggatggcgt ggaggtgcat    2220
aatgccaaga caaagccgcg ggaggagcag ttcaacagca cgtaccgtgt ggtcagcgtc    2280
ctcaccgtcc tgcaccagga ctggctgaac ggcaaggagt acaagtgcaa ggtctccaac    2340
aaaggcctcc cgtcctccat cgagaaaacc atctccaaag ccaagggca gccccgagag    2400 ccacaggtgt acaccctgcc cccatcccag gaggagatga ccaagaacca ggtcagcctg    2460
acctgcctgg tcaaaggctt ctaccccagc gacatcgccg tggagtggga gagcaatggg    2520
cagccggaga acaactacaa gaccacgcct cccgtgctgg actccgacgg ctccttcttc    2580
ctctacagca ggctaaccgt ggacaagagc aggtggcagg aggggaatgt cttctcatgc    2640
tccgtgatgc atgaggctct gcacaaccac tacacacaga gagcctctc cctgtctctg    2700 ggtaaatga    2709
```

<210> SEQ ID NO 8
<211> LENGTH: 902
<212> TYPE: PRT
<213> ORGANISM: Artificial Sequence
<220> FEATURE:
<223> OTHER INFORMATION: Synthetic

<400> SEQUENCE: 8

```
Met Val Leu Leu Arg Leu Ile Cys Phe Ile Ala Leu Leu Ile Ser Ser
  1               5                  10                  15

Leu Glu Ala Asp Lys Cys Lys Glu Arg Glu Lys Ile Ile Leu Val
              20                  25                  30

Ser Ser Ala Asn Glu Ile Asp Val Arg Pro Cys Pro Leu Asn Pro Asn
          35                  40                  45

Glu His Lys Gly Thr Ile Thr Trp Tyr Lys Asp Asp Ser Lys Thr Pro
      50                  55                  60

Val Ser Thr Glu Gln Ala Ser Arg Ile His Gln His Lys Glu Lys Leu
 65                  70                  75                  80

Trp Phe Val Pro Ala Lys Val Glu Asp Ser Gly His Tyr Tyr Cys Val
                  85                  90                  95

Val Arg Asn Ser Ser Tyr Cys Leu Arg Ile Lys Ile Ser Ala Lys Phe
             100                 105                 110

Val Glu Asn Glu Pro Asn Leu Cys Tyr Asn Ala Gln Ala Ile Phe Lys
         115                 120                 125

Gln Lys Leu Pro Val Ala Gly Asp Gly Gly Leu Val Cys Pro Tyr Met
     130                 135                 140
```

-continued

Glu Phe Phe Lys Asn Glu Asn Asn Glu Leu Pro Lys Leu Gln Trp Tyr
145                 150                 155                 160

Lys Asp Cys Lys Pro Leu Leu Leu Asp Asn Ile His Phe Ser Gly Val
            165                 170                 175

Lys Asp Arg Leu Ile Val Met Asn Val Ala Glu Lys His Arg Gly Asn
            180                 185                 190

Tyr Thr Cys His Ala Ser Tyr Thr Tyr Leu Gly Lys Gln Tyr Pro Ile
            195                 200                 205

Thr Arg Val Ile Glu Phe Ile Thr Leu Glu Glu Asn Lys Pro Thr Arg
210                 215                 220

Pro Val Ile Val Ser Pro Ala Asn Glu Thr Met Glu Val Asp Leu Gly
225                 230                 235                 240

Ser Gln Ile Gln Leu Ile Cys Asn Val Thr Gly Gln Leu Ser Asp Ile
            245                 250                 255

Ala Tyr Trp Lys Trp Asn Gly Ser Val Ile Asp Glu Asp Pro Val
            260                 265                 270

Leu Gly Glu Asp Tyr Tyr Ser Val Glu Asn Pro Ala Asn Lys Arg Arg
            275                 280                 285

Ser Thr Leu Ile Thr Val Leu Asn Ile Ser Glu Ile Glu Ser Arg Phe
290                 295                 300

Tyr Lys His Pro Phe Thr Cys Phe Ala Lys Asn Thr His Gly Ile Asp
305                 310                 315                 320

Ala Ala Tyr Ile Gln Leu Ile Tyr Pro Val Thr Asn Ser Glu Arg Cys
            325                 330                 335

Asp Asp Trp Gly Leu Asp Thr Met Arg Gln Ile Gln Val Phe Glu Asp
            340                 345                 350

Glu Pro Ala Arg Ile Lys Cys Pro Leu Phe Glu His Phe Leu Lys Phe
            355                 360                 365

Asn Tyr Ser Thr Ala His Ser Ala Gly Leu Thr Leu Ile Trp Tyr Trp
370                 375                 380

Thr Arg Gln Asp Arg Asp Leu Glu Glu Pro Ile Asn Phe Arg Leu Pro
385                 390                 395                 400

Glu Asn Arg Ile Ser Lys Glu Lys Asp Val Leu Trp Phe Arg Pro Thr
            405                 410                 415

Leu Leu Asn Asp Thr Gly Asn Tyr Thr Cys Met Leu Arg Asn Thr Thr
            420                 425                 430

Tyr Cys Ser Lys Val Ala Phe Pro Leu Glu Val Val Gln Lys Asp Ser
            435                 440                 445

Cys Phe Asn Ser Pro Met Lys Leu Pro Val His Lys Leu Tyr Ile Glu
            450                 455                 460

Tyr Gly Ile Gln Arg Ile Thr Cys Pro Asn Val Asp Gly Tyr Phe Pro
465                 470                 475                 480

Ser Ser Val Lys Pro Thr Ile Thr Trp Tyr Met Gly Cys Tyr Lys Ile
            485                 490                 495

Gln Asn Phe Asn Asn Val Ile Pro Glu Gly Met Asn Leu Ser Phe Leu
            500                 505                 510

Ile Ala Leu Ile Ser Asn Asn Gly Asn Tyr Thr Cys Val Val Thr Tyr
            515                 520                 525

Pro Glu Asn Gly Arg Thr Phe His Leu Thr Arg Thr Leu Thr Val Lys
            530                 535                 540

Val Val Gly Ser Pro Lys Asn Ala Val Pro Pro Val Ile His Ser Pro
545                 550                 555                 560

```
Asn Asp His Val Val Tyr Glu Lys Glu Pro Gly Glu Leu Leu Ile
            565                 570                 575

Pro Cys Thr Val Tyr Phe Ser Phe Leu Met Asp Ser Arg Asn Glu Val
            580                 585                 590

Trp Trp Thr Ile Asp Gly Lys Lys Pro Asp Ile Thr Ile Asp Val
            595                 600                 605

Thr Ile Asn Glu Ser Ile Ser His Ser Arg Thr Glu Asp Glu Thr Arg
            610                 615                 620

Thr Gln Ile Leu Ser Ile Lys Lys Val Thr Ser Glu Asp Leu Lys Arg
625                 630                 635                 640

Ser Tyr Val Cys His Ala Arg Ser Ala Lys Gly Glu Val Ala Lys Ala
                    645                 650                 655

Ala Lys Val Lys Gln Lys Val Pro Ala Pro Arg Tyr Thr Val Glu Ser
                660                 665                 670

Gly Glu Ser Lys Tyr Gly Pro Pro Cys Pro Pro Cys Pro Ala Pro Glu
                675                 680                 685

Phe Leu Gly Gly Pro Ser Val Phe Leu Phe Pro Pro Lys Pro Lys Asp
            690                 695                 700

Thr Leu Met Ile Ser Arg Thr Pro Glu Val Thr Cys Val Val Val Asp
705                 710                 715                 720

Val Ser Gln Glu Asp Pro Glu Val Gln Phe Asn Trp Tyr Val Asp Gly
                    725                 730                 735

Val Glu Val His Asn Ala Lys Thr Lys Pro Arg Glu Glu Gln Phe Asn
                740                 745                 750

Ser Thr Tyr Arg Val Val Ser Val Leu Thr Val Leu His Gln Asp Trp
            755                 760                 765

Leu Asn Gly Lys Glu Tyr Lys Cys Lys Val Ser Asn Lys Gly Leu Pro
770                 775                 780

Ser Ser Ile Glu Lys Thr Ile Ser Lys Ala Lys Gly Gln Pro Arg Glu
785                 790                 795                 800

Pro Gln Val Tyr Thr Leu Pro Pro Ser Gln Glu Met Thr Lys Asn
                    805                 810                 815

Gln Val Ser Leu Thr Cys Leu Val Lys Gly Phe Tyr Pro Ser Asp Ile
                820                 825                 830

Ala Val Glu Trp Glu Ser Asn Gly Gln Pro Glu Asn Asn Tyr Lys Thr
            835                 840                 845

Thr Pro Pro Val Leu Asp Ser Asp Gly Ser Phe Phe Leu Tyr Ser Arg
850                 855                 860

Leu Thr Val Asp Lys Ser Arg Trp Gln Glu Gly Asn Val Phe Ser Cys
865                 870                 875                 880

Ser Val Met His Glu Ala Leu His Asn His Tyr Thr Gln Lys Ser Leu
                    885                 890                 895

Ser Leu Ser Leu Gly Lys
            900

<210> SEQ ID NO 9
<211> LENGTH: 2703
<212> TYPE: DNA
<213> ORGANISM: Artificial Sequence
<220> FEATURE:
<223> OTHER INFORMATION: Synthetic

<400> SEQUENCE: 9
atggtgcttc tgtggtgtgt agtgagtctc tacttttatg gaatcctgca aagtgatgcc      60
tcagaacgct gcgatgactg gggactagac accatgaggc aaatccaagt gtttgaagat     120
```

```
gagccagctc gcatcaagtg cccactcttt gaacacttct tgaaattcaa ctacagcaca    180
gcccattcag ctggccttac tctgatctgg tattggacta ggcaggaccg ggaccttgag    240
gagccaatta acttccgcct ccccgagaac cgcattagta aggagaaaga tgtgctgtgg    300
ttccggccca ctctcctcaa tgacactggc aactatacct gcatgttaag gaacactaca    360
tattgcagca aagttgcatt tcccttggaa gttgttcaaa aagacagctg tttcaattcc    420
cccatgaaac tcccagtgca taaactgtat atagaatatg gcattcagag gatcacttgt    480
ccaaatgtag atggatattt tccttccagt gtcaaaccga ctatcacttg gtatatgggc    540
tgttataaaa tacagaattt taataatgta atacccgaag gtatgaactt gagtttcctc    600
attgccttaa tttcaaataa tggaaattac acatgtgttg ttacatatcc agaaaatgga    660
cgtacgtttc atctcaccag gactctgact gtaaaggtag taggctctcc aaaaaatgca    720 gtgcccctg tgatccattc acctaatgat catgtggtct atgagaaaga accaggagag    780
gagctactca ttccctgtac ggtctatttt agttttctga tggattctcg caatgaggtt    840
tggtggacca ttgatggaaa aaaacctgat gacatcacta ttgatgtcac cattaacgaa    900
agtataagtc atagtagaac agaagatgaa acaagaactc agattttgag catcaagaaa    960
gttacctctg aggatctcaa gcgcagctat gtctgtcatg ctagaagtgc aaaggcgaa   1020 gttgccaaag cagccaaggt gaagcagaaa gtgccagctc aagatacac agtggaaaaa    1080 tgcaaggaac gtgaagaaaa aataatttta gtgagctcag caaatgaaat cgatgttcgt    1140
ccctgtcctc ttaacccaaa tgaacacaaa ggcactataa cttggtataa ggatgacagc    1200
aagacacctg tatctacaga acaagcctcc aggattcatc aacacaaaga gaaactttgg    1260
tttgttcctg ctaaggtgga ggattcagga cattactatt gcgtggtaag aaattcatct    1320
tactgcctca gaattaaaat aagtgcaaaa tttgtggaga atgagcctaa cttatgttat    1380
aatgcacaag ccatatttaa gcagaaacta cccgttgcag gagacggagg acttgtgtgc    1440
ccttatatgg agttttttaa aaatgaaaat aatgagttac ctaaattaca gtggtataag    1500
gattgcaaac ctctacttct tgacaatata cactttagtg gagtcaaaga taggctcatc    1560
gtgatgaatg tggctgaaaa gcatagaggg aactatactt gtcatgcatc ctacacatac    1620
ttgggcaagc aatatcctat tacccgggta atagaattta ttactctaga ggaaaacaaa    1680
cccacaaggc ctgtgattgt gagcccagct aatgagacaa tggaagtaga cttgggatcc    1740
cagatacaat tgatctgtaa tgtcaccggc cagttgagtg acattgctta ctggaagtgg    1800
aatgggtcag taattgatga agatgaccca gtgctagggg aagactatta cagtgtggaa    1860
aatcctgcaa acaaaagaag gagtaccctc atcacagtgc ttaatatatc ggaaattgag    1920
agtagatttt ataaacatcc atttacctgt tttgccaaga atacacatgg tatagatgca    1980
gcatatatcc agttaatata tccagtcact aattccggag acaaaactca cacatgccca    2040
ccgtgcccag cacctgaact cctgggggga ccgtcagtct tcctcttccc cccaaaaccc    2100
aaggacaccc tcatgatctc ccggacccct gaggtcacat gcgtggtggt ggacgtgagc    2160
cacgaagacc ctgaggtcaa gttcaactgg tacgtggacg gcgtggaggt gcataatgcc    2220
aagacaaagc cgcgggagga gcagtacaac agcacgtacc gtgtggtcag cgtcctcacc    2280
gtcctgcacc aggactggct gaatggcaag gagtacaagt gcaaggtctc caacaaagcc    2340
ctcccagccc ccatcgagaa aaccatctcc aaagccaaag gcagccccg agaaccacag    2400 gtgtacaccc tgcccccatc ccgggatgag ctgaccaaga accaggtcag cctgacctgc    2460
```

-continued

```
ctggtcaaag gcttctatcc cagcgacatc gccgtggagt gggagagcaa tgggcagccg    2520
gagaacaact acaagaccac gcctcccgtg ctggactccg acggctcctt cttcctctac    2580
agcaagctca ccgtggacaa gagcaggtgg cagcagggga acgtcttctc atgctccgtg    2640
atgcatgagg ctctgcacaa ccactacacg cagaagagcc tctccctgtc tccgggtaaa    2700
tga                                                                 2703
```

<210> SEQ ID NO 10
<211> LENGTH: 900
<212> TYPE: PRT
<213> ORGANISM: Artificial Sequence
<220> FEATURE:
<223> OTHER INFORMATION: Synthetic

<400> SEQUENCE: 10

```
Met Val Leu Leu Trp Cys Val Val Ser Leu Tyr Phe Tyr Gly Ile Leu
 1               5                  10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320
```

-continued

```
Val Thr Ser Glu Asp Leu Lys Arg Ser Tyr Val Cys His Ala Arg Ser
            325                 330                 335

Ala Lys Gly Glu Val Ala Lys Ala Ala Lys Val Lys Gln Lys Val Pro
        340                 345                 350

Ala Pro Arg Tyr Thr Val Glu Lys Cys Lys Arg Glu Glu Lys Ile
    355                 360                 365

Ile Leu Val Ser Ser Ala Asn Glu Ile Asp Val Arg Pro Cys Pro Leu
370                 375                 380

Asn Pro Asn Glu His Lys Gly Thr Ile Thr Trp Tyr Lys Asp Asp Ser
385                 390                 395                 400

Lys Thr Pro Val Ser Thr Glu Gln Ala Ser Arg Ile His Gln His Lys
                405                 410                 415

Glu Lys Leu Trp Phe Val Pro Ala Lys Val Glu Asp Ser Gly His Tyr
            420                 425                 430

Tyr Cys Val Val Arg Asn Ser Ser Tyr Cys Leu Arg Ile Lys Ile Ser
        435                 440                 445

Ala Lys Phe Val Glu Asn Glu Pro Asn Leu Cys Tyr Asn Ala Gln Ala
    450                 455                 460

Ile Phe Lys Gln Lys Leu Pro Val Ala Gly Asp Gly Gly Leu Val Cys
465                 470                 475                 480

Pro Tyr Met Glu Phe Phe Lys Asn Glu Asn Asn Glu Leu Pro Lys Leu
                485                 490                 495

Gln Trp Tyr Lys Asp Cys Lys Pro Leu Leu Leu Asp Asn Ile His Phe
            500                 505                 510

Ser Gly Val Lys Asp Arg Leu Ile Val Met Asn Val Ala Glu Lys His
        515                 520                 525

Arg Gly Asn Tyr Thr Cys His Ala Ser Tyr Thr Tyr Leu Gly Lys Gln
    530                 535                 540

Tyr Pro Ile Thr Arg Val Ile Glu Phe Ile Thr Leu Glu Glu Asn Lys
545                 550                 555                 560

Pro Thr Arg Pro Val Ile Val Ser Pro Ala Asn Glu Thr Met Glu Val
                565                 570                 575

Asp Leu Gly Ser Gln Ile Gln Leu Ile Cys Asn Val Thr Gly Gln Leu
            580                 585                 590

Ser Asp Ile Ala Tyr Trp Lys Trp Asn Gly Ser Val Ile Asp Glu Asp
        595                 600                 605

Asp Pro Val Leu Gly Glu Asp Tyr Tyr Ser Val Glu Asn Pro Ala Asn
    610                 615                 620

Lys Arg Arg Ser Thr Leu Ile Thr Val Leu Asn Ile Ser Glu Ile Glu
625                 630                 635                 640

Ser Arg Phe Tyr Lys His Pro Phe Thr Cys Phe Ala Lys Asn Thr His
                645                 650                 655

Gly Ile Asp Ala Ala Tyr Ile Gln Leu Ile Tyr Pro Val Thr Asn Ser
            660                 665                 670

Gly Asp Lys Thr His Thr Cys Pro Pro Cys Pro Ala Pro Glu Leu Leu
        675                 680                 685

Gly Gly Pro Ser Val Phe Leu Phe Pro Pro Lys Pro Lys Asp Thr Leu
    690                 695                 700

Met Ile Ser Arg Thr Pro Glu Val Thr Cys Val Val Val Asp Val Ser
705                 710                 715                 720

His Glu Asp Pro Glu Val Lys Phe Asn Trp Tyr Val Asp Gly Val Glu
                725                 730                 735
```

-continued

```
Val His Asn Ala Lys Thr Lys Pro Arg Glu Glu Gln Tyr Asn Ser Thr
            740                 745                 750
Tyr Arg Val Val Ser Val Leu Thr Val Leu His Gln Asp Trp Leu Asn
        755                 760                 765
Gly Lys Glu Tyr Lys Cys Lys Val Ser Asn Lys Ala Leu Pro Ala Pro
    770                 775                 780
Ile Glu Lys Thr Ile Ser Lys Ala Lys Gly Gln Pro Arg Glu Pro Gln
785                 790                 795                 800
Val Tyr Thr Leu Pro Pro Ser Arg Asp Glu Leu Thr Lys Asn Gln Val
                805                 810                 815
Ser Leu Thr Cys Leu Val Lys Gly Phe Tyr Pro Ser Asp Ile Ala Val
            820                 825                 830
Glu Trp Glu Ser Asn Gly Gln Pro Glu Asn Asn Tyr Lys Thr Thr Pro
        835                 840                 845
Pro Val Leu Asp Ser Asp Gly Ser Phe Phe Leu Tyr Ser Lys Leu Thr
    850                 855                 860
Val Asp Lys Ser Arg Trp Gln Gln Gly Asn Val Phe Ser Cys Ser Val
865                 870                 875                 880
Met His Glu Ala Leu His Asn His Tyr Thr Gln Lys Ser Leu Ser Leu
                885                 890                 895
Ser Pro Gly Lys
            900

<210> SEQ ID NO 11
<211> LENGTH: 2709
<212> TYPE: DNA
<213> ORGANISM: Artificial Sequence
<220> FEATURE:
<223> OTHER INFORMATION: Synthetic

<400> SEQUENCE: 11
atggtgcttc tgtggtgtgt agtgagtctc tacttttatg gaatcctgca aagtgatgcc      60
tcagaacgct gcgatgactg gggactagac accatgaggc aaatccaagt gtttgaagat     120
gagccagctc gcatcaagtg cccactcttt gaacacttct tgaaattcaa ctacagcaca     180
gcccattcag ctggccttac tctgatctgg tattggacta ggcaggaccg ggaccttgag     240
gagccaatta cttccgcctc cccgagaacc gcattagta aggagaaaga tgtgctgtgg     300
ttccggccca ctctcctcaa tgacactggc aactatacct gcatgttaag gaacactaca     360
tattgcagca agttgcatt tcccttggaa gttgttcaaa agacagctg tttcaattcc     420 cccatgaaac tcccagtgca taaactgtat atagaatatg cattcagag gatcacttgt     480 ccaaatgtag atgatatttt ccttccagt gtcaaaccga ctatcacttg gtatatgggc     540
tgttataaaa tacagaattt taataatgta atacccgaag gtatgaactt gagtttcctc     600
attgccttaa tttcaaataa tggaaattac acatgtgttg ttacatatcc agaaaatgga     660
cgtacgtttc atctcaccag gactctgact gtaaaggtag taggctctcc aaaaaatgca     720 gtgcccctg tgatccattc acctaatgat catgtggtct atgagaaaga accaggagag     780
gagctactca ttccctgtac ggtctatttt agttttctga tggattctcg caatgaggtt     840
tggtggacca ttgatggaaa aaacctgat gacatcacta ttgatgtcac cattaacgaa     900
agtataagtc atagtagaac agaagatgaa acaagaactc agattttgag catcaagaaa     960
gttacctctg aggatctcaa gcgcagctat gtctgtcatg ctagaagtgc caaaggcgaa    1020
gttgccaaag cagccaaggt gaagcagaaa gtgccagctc caagatacac agtggaaaaa    1080
```

-continued

```
tgcaaggaac gtgaagaaaa aataatttta gtgagctcag caaatgaaat cgatgttcgt    1140
ccctgtcctc ttaacccaaa tgaacacaaa ggcactataa cttggtataa ggatgacagc    1200
aagacacctg tatctacaga acaagcctcc aggattcatc aacacaaaga gaaactttgg    1260
tttgttcctg ctaaggtgga ggattcagga cattactatt gcgtggtaag aaattcatct    1320
tactgcctca gaattaaaat aagtgcaaaa tttgtggaga atgagcctaa cttatgttat    1380
aatgcacaag ccatatttaa gcagaaacta cccgttgcag gagacggagg acttgtgtgc    1440
ccttatatgg agttttttaa aaatgaaaat aatgagttac ctaaattaca gtggtataag    1500
gattgcaaac ctctacttct tgacaatata cactttagtg gagtcaaaga taggctcatc    1560
gtgatgaatg tggctgaaaa gcatagaggg aactatactt gtcatgcatc ctacacatac    1620
ttgggcaagc aatatcctat tacccgggta atagaattta ttactctaga ggaaaacaaa    1680
cccacaaggc ctgtgattgt gagcccagct aatgagacaa tggaagtaga cttgggatcc    1740
cagatacaat tgatctgtaa tgtcaccggc cagttgagtg acattgctta ctggaagtgg    1800
aatgggtcag taattgatga agatgaccca gtgctagggg aagactatta cagtgtggaa    1860
aatcctgcaa acaaaagaag gagtaccctc atcacagtgc ttaatatatc ggaaattgag    1920
agtagatttt ataaacatcc atttacctgt tttgccaaga atacacatgg tatagatgca    1980
gcatatatcc agttaatata tccagtcact aattccggag agtccaaata cggtccgcca    2040
tgcccatcat gcccagcacc tgagttcctg gggggaccat cagtcttcct gttccccccca    2100 aaacccaagg acactctcat gatctcccgg acccctgagg tcacgtgcgt ggtggtggac    2160
gtgagccagg aagaccccga ggtccagttc aactggtacg tggatggcgt ggaggtgcat    2220
aatgccaaga caaagccgcg ggaggagcag ttcaacagca cgtaccgtgt ggtcagcgtc    2280
ctcaccgtcc tgcaccagga ctggctgaac ggcaaggagt acaagtgcaa ggtctccaac    2340
aaaggcctcc cgtcctccat cgagaaaacc atctccaaag ccaaagggca gccccgagag    2400
ccacaggtgt acaccctgcc cccatcccag gaggagatga ccaagaacca ggtcagcctg    2460
acctgcctgg tcaaaggctt ctaccccagc gacatcgccg tggagtggga gagcaatggg    2520
cagccggaga acaactacaa gaccacgcct cccgtgctgg actccgacgg ctccttcttc    2580
ctctacagca ggctaaccgt ggacaagagc aggtggcagg aggggaatgt cttctcatgc    2640
tccgtgatgc atgaggctct gcacaaccac tacacacaga agagcctctc cctgtctctg    2700
ggtaaatga                                                           2709
```

<210> SEQ ID NO 12
<211> LENGTH: 902
<212> TYPE: PRT
<213> ORGANISM: Artificial Sequence
<220> FEATURE:
<223> OTHER INFORMATION: Synthetic

<400> SEQUENCE: 12

```
Met Val Leu Leu Trp Cys Val Val Ser Leu Tyr Phe Tyr Gly Ile Leu
 1               5                  10                  15

Gln Ser Asp Ala Ser Glu Arg Cys Asp Asp Trp Gly Leu Asp Thr Met
             20                  25                  30

Arg Gln Ile Gln Val Phe Glu Asp Glu Pro Ala Arg Ile Lys Cys Pro
         35                  40                  45

Leu Phe Glu His Phe Leu Lys Phe Asn Tyr Ser Thr Ala His Ser Ala
     50                  55                  60

Gly Leu Thr Leu Ile Trp Tyr Trp Thr Arg Gln Asp Arg Asp Leu Glu
```

-continued

```
                65                  70                  75                  80
Glu Pro Ile Asn Phe Arg Leu Pro Glu Asn Arg Ile Ser Lys Glu Lys
                    85                  90                  95

Asp Val Leu Trp Phe Arg Pro Thr Leu Leu Asn Asp Thr Gly Asn Tyr
                100                 105                 110

Thr Cys Met Leu Arg Asn Thr Thr Tyr Cys Ser Lys Val Ala Phe Pro
                115                 120                 125

Leu Glu Val Val Gln Lys Asp Ser Cys Phe Asn Ser Pro Met Lys Leu
                130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
                180                 185                 190

Glu Gly Met Asn Leu Ser Phe Leu Ile Ala Leu Ile Ser Asn Asn Gly
                195                 200                 205

Asn Tyr Thr Cys Val Val Thr Tyr Pro Glu Asn Gly Arg Thr Phe His
                210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
                260                 265                 270

Leu Met Asp Ser Arg Asn Glu Val Trp Trp Thr Ile Asp Gly Lys Lys
                275                 280                 285

Pro Asp Asp Ile Thr Ile Asp Val Thr Ile Asn Glu Ser Ile Ser His
                290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
                340                 345                 350

Ala Pro Arg Tyr Thr Val Glu Lys Cys Lys Glu Arg Glu Glu Lys Ile
                355                 360                 365

Ile Leu Val Ser Ser Ala Asn Glu Ile Asp Val Arg Pro Cys Pro Leu
                370                 375                 380

Asn Pro Asn Glu His Lys Gly Thr Ile Thr Trp Tyr Lys Asp Asp Ser
385                 390                 395                 400

Lys Thr Pro Val Ser Thr Glu Gln Ala Ser Arg Ile His Gln His Lys
                405                 410                 415

Glu Lys Leu Trp Phe Val Pro Ala Lys Val Glu Asp Ser Gly His Tyr
                420                 425                 430

Tyr Cys Val Val Arg Asn Ser Ser Tyr Cys Leu Arg Ile Lys Ile Ser
                435                 440                 445

Ala Lys Phe Val Glu Asn Glu Pro Asn Leu Cys Tyr Asn Ala Gln Ala
                450                 455                 460

Ile Phe Lys Gln Lys Leu Pro Val Ala Gly Asp Gly Gly Leu Val Cys
465                 470                 475                 480

Pro Tyr Met Glu Phe Phe Lys Asn Glu Asn Asn Glu Leu Pro Lys Leu
                485                 490                 495
```

```
Gln Trp Tyr Lys Asp Cys Lys Pro Leu Leu Leu Asp Asn Ile His Phe
            500                 505                 510
Ser Gly Val Lys Asp Arg Leu Ile Val Met Asn Val Ala Glu Lys His
        515                 520                 525
Arg Gly Asn Tyr Thr Cys His Ala Ser Tyr Thr Tyr Leu Gly Lys Gln
        530                 535                 540
Tyr Pro Ile Thr Arg Val Ile Glu Phe Ile Thr Leu Glu Glu Asn Lys
545                 550                 555                 560
Pro Thr Arg Pro Val Ile Val Ser Pro Ala Asn Glu Thr Met Glu Val
                565                 570                 575
Asp Leu Gly Ser Gln Ile Gln Leu Ile Cys Asn Val Thr Gly Gln Leu
            580                 585                 590
Ser Asp Ile Ala Tyr Trp Lys Trp Asn Gly Ser Val Ile Asp Glu Asp
        595                 600                 605
Asp Pro Val Leu Gly Glu Asp Tyr Tyr Ser Val Glu Asn Pro Ala Asn
        610                 615                 620
Lys Arg Arg Ser Thr Leu Ile Thr Val Leu Asn Ile Ser Glu Ile Glu
625                 630                 635                 640
Ser Arg Phe Tyr Lys His Pro Phe Thr Cys Phe Ala Lys Asn Thr His
                645                 650                 655
Gly Ile Asp Ala Ala Tyr Ile Gln Leu Ile Tyr Pro Val Thr Asn Ser
            660                 665                 670
Gly Glu Ser Lys Tyr Gly Pro Cys Pro Ser Cys Pro Ala Pro Glu
        675                 680                 685
Phe Leu Gly Gly Pro Ser Val Phe Leu Phe Pro Pro Lys Pro Lys Asp
        690                 695                 700
Thr Leu Met Ile Ser Arg Thr Pro Glu Val Thr Cys Val Val Val Asp
705                 710                 715                 720
Val Ser Gln Glu Asp Pro Glu Val Gln Phe Asn Trp Tyr Val Asp Gly
                725                 730                 735
Val Glu Val His Asn Ala Lys Thr Lys Pro Arg Glu Glu Gln Phe Asn
            740                 745                 750
Ser Thr Tyr Arg Val Val Ser Val Leu Thr Val Leu His Gln Asp Trp
        755                 760                 765
Leu Asn Gly Lys Glu Tyr Lys Cys Lys Val Ser Asn Lys Gly Leu Pro
        770                 775                 780
Ser Ser Ile Glu Lys Thr Ile Ser Lys Ala Lys Gly Gln Pro Arg Glu
785                 790                 795                 800
Pro Gln Val Tyr Thr Leu Pro Pro Ser Gln Glu Glu Met Thr Lys Asn
                805                 810                 815
Gln Val Ser Leu Thr Cys Leu Val Lys Gly Phe Tyr Pro Ser Asp Ile
            820                 825                 830
Ala Val Glu Trp Glu Ser Asn Gly Gln Pro Glu Asn Asn Tyr Lys Thr
        835                 840                 845
Thr Pro Pro Val Leu Asp Ser Asp Gly Ser Phe Phe Leu Tyr Ser Arg
        850                 855                 860
Leu Thr Val Asp Lys Ser Arg Trp Gln Glu Gly Asn Val Phe Ser Cys
865                 870                 875                 880
Ser Val Met His Glu Ala Leu His Asn His Tyr Thr Gln Lys Ser Leu
                885                 890                 895
Ser Leu Ser Leu Gly Lys
            900
```

<210> SEQ ID NO 13
<211> LENGTH: 2709
<212> TYPE: DNA
<213> ORGANISM: Artificial Sequence
<220> FEATURE:
<223> OTHER INFORMATION: Synthetic

<400> SEQUENCE: 13

| | | | | | |
|---|---|---|---|---|---|
| atggtgcttc | tgtggtgtgt | agtgagtctc | tactttatg | gaatcctgca | aagtgatgcc | 60 |
| tcagaacgct | gcgatgactg | gggactagac | accatgaggc | aaatccaagt | gtttgaagat | 120 |
| gagccagctc | gcatcaagtg | cccactcttt | gaacacttct | tgaaattcaa | ctacagcaca | 180 |
| gcccattcag | ctggccttac | tctgatctgg | tattggacta | ggcaggaccg | gaccttgag | 240 |
| gagccaatta | acttccgcct | ccccgagaac | cgcattagta | aggagaaaga | tgtgctgtgg | 300 |
| ttccggccca | ctctcctcaa | tgacactggc | aactatacct | gcatgttaag | gaacactaca | 360 |
| tattgcagca | aagttgcatt | tcccttggaa | gttgttcaaa | aagacagctg | tttcaattcc | 420 |
| cccatgaaac | tcccagtgca | taaactgtat | atagaatatg | gcattcagag | gatcacttgt | 480 |
| ccaaatgtag | atggatattt | tccttccagt | gtcaaaccga | ctatcacttg | gtatatgggc | 540 |
| tgttataaaa | tacagaattt | taataatgta | atacccgaag | gtatgaactt | gagtttcctc | 600 |
| attgccttaa | tttcaaataa | tggaaattac | acatgtgttg | ttacatatcc | agaaaatgga | 660 |
| cgtacgtttc | atctcaccag | gactctgact | gtaaaggtag | taggctctcc | aaaaaatgca | 720 |
| gtgccccctg | tgatccattc | acctaatgat | catgtggtct | atgagaaaga | accaggagag | 780 |
| gagctactca | ttccctgtac | ggtctatttt | agttttctga | tggattctcg | caatgaggtt | 840 |
| tggtggacca | ttgatggaaa | aaacctgat | gacatcacta | ttgatgtcac | cattaacgaa | 900 |
| agtataagtc | atagtagaac | agaagatgaa | acaagaactc | agattttgag | catcaagaaa | 960 |
| gttacctctg | aggatctcaa | gcgcagctat | gtctgtcatg | ctagaagtgc | aaaggcgaa | 1020 |
| gttgccaaag | cagccaaggt | gaagcagaaa | gtgccagctc | caagatacac | agtggaaaaa | 1080 |
| tgcaaggaac | gtgaagaaaa | aataattta | gtgagctcag | caaatgaaat | cgatgttcgt | 1140 |
| ccctgtcctc | ttaacccaaa | tgaacacaaa | ggcactataa | cttggtataa | ggatgacagc | 1200 |
| aagacacctg | tatctacaga | acaagcctcc | aggattcatc | aacacaaaga | gaaactttgg | 1260 |
| tttgttcctg | ctaaggtgga | ggattcagga | cattactatt | gcgtggtaag | aaattcatct | 1320 |
| tactgcctca | gaattaaaat | aagtgcaaaa | tttgtggaga | atgagcctaa | cttatgttat | 1380 |
| aatgcacaag | ccatatttaa | gcagaaacta | cccgttgcag | agacggagg | acttgtgtgc | 1440 |
| ccttatatgg | agttttttaa | aaatgaaaat | aatgagttac | ctaaattaca | gtggtataag | 1500 |
| gattgcaaac | ctctacttct | tgacaatata | cactttagtg | gagtcaaaga | taggctcatc | 1560 |
| gtgatgaatg | tggctgaaaa | gcatagaggg | aactatactt | gtcatgcatc | ctacacatac | 1620 |
| ttgggcaagc | aatatcctat | tacccgggta | atagaattta | ttactctaga | ggaaaacaaa | 1680 |
| cccacaaggc | ctgtgattgt | gagcccagct | aatgagacaa | tggaagtaga | cttgggatcc | 1740 |
| cagatacaat | tgatctgtaa | tgtcaccggc | cagttgagtg | acattgctta | ctggaagtgg | 1800 |
| aatgggtcag | taattgatga | agatgaccca | gtgctagggg | aagactatta | cagtgtggaa | 1860 |
| aatcctgcaa | acaaaagaag | gagtaccctc | atcacagtgc | ttaatatatc | ggaaattgag | 1920 |
| agtagatttt | ataaacatcc | atttacctgt | tttgccaaga | atacacatgg | tatagatgca | 1980 |
| gcatatatcc | agttaatata | tccagtcact | aattccggag | agtccaaata | cggtccgcca | 2040 |
| tgcccaccat | gcccagcacc | tgagttcctg | ggggaccat | cagtcttcct | gttcccccca | 2100 |

-continued

```
aaacccaagg acactctcat gatctcccgg accccctgagg tcacgtgcgt ggtggtggac   2160
gtgagccagg aagaccccga ggtccagttc aactggtacg tggatggcgt ggaggtgcat   2220
aatgccaaga caaagccgcg ggaggagcag ttcaacagca cgtaccgtgt ggtcagcgtc   2280
ctcaccgtcc tgcaccagga ctggctgaac ggcaaggagt acaagtgcaa ggtctccaac   2340
aaaggcctcc cgtcctccat cgagaaaacc atctccaaag ccaagggcag ccccgagag    2400 ccacaggtgt acaccctgcc cccatcccag gaggagatga ccaagaacca ggtcagcctg   2460
acctgcctgg tcaaaggctt ctaccccagc gacatcgccg tggagtggga gagcaatggg   2520
cagccggaga acaactacaa gaccacgcct cccgtgctgg actccgacgg ctccttcttc   2580
ctctacagca agctaaccgt ggacaagagc aggtggcagg aggggaatgt cttctcatgc   2640
tccgtgatgc atgaggctct gcacaaccac tacacacaga agagcctctc cctgtctctg   2700
ggtaaatga                                                           2709
```

<210> SEQ ID NO 14
<211> LENGTH: 902
<212> TYPE: PRT
<213> ORGANISM: Artificial Sequence
<220> FEATURE:
<223> OTHER INFORMATION: Synthetic

<400> SEQUENCE: 14

```
Met Val Leu Leu Trp Cys Val Val Ser Leu Tyr Phe Tyr Gly Ile Leu
 1               5                  10                  15

Gln Ser Asp Ala Ser Glu Arg Cys Asp Asp Trp Gly Leu Asp Thr Met
                20                  25                  30

Arg Gln Ile Gln Val Phe Glu Asp Glu Pro Ala Arg Ile Lys Cys Pro
            35                  40                  45

Leu Phe Glu His Phe Leu Lys Phe Asn Tyr Ser Thr Ala His Ser Ala
        50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Gly Ser Pro Lys Asn Ala
225                 230                 235                 240

Val Pro Pro Val Ile His Ser Pro Asn Asp His Val Val Tyr Glu Lys
```

-continued

```
                245                 250                 255
Glu Pro Gly Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
        290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Lys Val Lys Gln Lys Val Pro
            340                 345                 350

Ala Pro Arg Tyr Thr Val Glu Lys Cys Lys Glu Arg Glu Lys Ile
        355                 360                 365

Ile Leu Val Ser Ser Ala Asn Glu Ile Asp Val Arg Pro Cys Pro Leu
        370                 375                 380

Asn Pro Asn Glu His Lys Gly Thr Ile Thr Trp Tyr Lys Asp Asp Ser
385                 390                 395                 400

Lys Thr Pro Val Ser Thr Glu Gln Ala Ser Arg Ile His Gln His Lys
                405                 410                 415

Glu Lys Leu Trp Phe Val Pro Ala Lys Val Glu Asp Ser Gly His Tyr
                420                 425                 430

Tyr Cys Val Val Arg Asn Ser Ser Tyr Cys Leu Arg Ile Lys Ile Ser
            435                 440                 445

Ala Lys Phe Val Glu Asn Glu Pro Asn Leu Cys Tyr Asn Ala Gln Ala
        450                 455                 460

Ile Phe Lys Gln Lys Leu Pro Val Ala Gly Asp Gly Leu Val Cys
465                 470                 475                 480

Pro Tyr Met Glu Phe Phe Lys Asn Glu Asn Asn Glu Leu Pro Lys Leu
                485                 490                 495

Gln Trp Tyr Lys Asp Cys Lys Pro Leu Leu Leu Asp Asn Ile His Phe
            500                 505                 510

Ser Gly Val Lys Asp Arg Leu Ile Val Met Asn Val Ala Glu Lys His
        515                 520                 525

Arg Gly Asn Tyr Thr Cys His Ala Ser Tyr Thr Tyr Leu Gly Lys Gln
        530                 535                 540

Tyr Pro Ile Thr Arg Val Ile Glu Phe Ile Thr Leu Glu Glu Asn Lys
545                 550                 555                 560

Pro Thr Arg Pro Val Ile Val Ser Pro Ala Asn Glu Thr Met Glu Val
                565                 570                 575

Asp Leu Gly Ser Gln Ile Gln Leu Ile Cys Asn Val Thr Gly Gln Leu
            580                 585                 590

Ser Asp Ile Ala Tyr Trp Lys Trp Asn Gly Ser Val Ile Asp Glu Asp
        595                 600                 605

Asp Pro Val Leu Gly Glu Asp Tyr Tyr Ser Val Glu Asn Pro Ala Asn
        610                 615                 620

Lys Arg Arg Ser Thr Leu Ile Thr Val Leu Asn Ile Ser Glu Ile Glu
625                 630                 635                 640

Ser Arg Phe Tyr Lys His Pro Phe Thr Cys Phe Ala Lys Asn Thr His
                645                 650                 655

Gly Ile Asp Ala Ala Tyr Ile Gln Leu Ile Tyr Pro Val Thr Asn Ser
            660                 665                 670
```

Gly Glu Ser Lys Tyr Gly Pro Pro Cys Pro Cys Pro Ala Pro Glu
            675                 680                 685

Phe Leu Gly Gly Pro Ser Val Phe Leu Phe Pro Pro Lys Pro Lys Asp
        690                 695                 700

Thr Leu Met Ile Ser Arg Thr Pro Glu Val Thr Cys Val Val Val Asp
705                 710                 715                 720

Val Ser Gln Glu Asp Pro Glu Val Gln Phe Asn Trp Tyr Val Asp Gly
                725                 730                 735

Val Glu Val His Asn Ala Lys Thr Lys Pro Arg Glu Glu Gln Phe Asn
            740                 745                 750

Ser Thr Tyr Arg Val Val Ser Val Leu Thr Val Leu His Gln Asp Trp
        755                 760                 765

Leu Asn Gly Lys Glu Tyr Lys Cys Lys Val Ser Asn Lys Gly Leu Pro
    770                 775                 780

Ser Ser Ile Glu Lys Thr Ile Ser Lys Ala Lys Gly Gln Pro Arg Glu
785                 790                 795                 800

Pro Gln Val Tyr Thr Leu Pro Pro Ser Gln Glu Glu Met Thr Lys Asn
                805                 810                 815

Gln Val Ser Leu Thr Cys Leu Val Lys Gly Phe Tyr Pro Ser Asp Ile
            820                 825                 830

Ala Val Glu Trp Glu Ser Asn Gly Gln Pro Glu Asn Asn Tyr Lys Thr
        835                 840                 845

Thr Pro Pro Val Leu Asp Ser Asp Gly Ser Phe Phe Leu Tyr Ser Arg
    850                 855                 860

Leu Thr Val Asp Lys Ser Arg Trp Gln Glu Gly Asn Val Phe Ser Cys
865                 870                 875                 880

Ser Val Met His Glu Ala Leu His Asn His Tyr Thr Gln Lys Ser Leu
                885                 890                 895

Ser Leu Ser Leu Gly Lys
            900

<210> SEQ ID NO 15
<211> LENGTH: 2748
<212> TYPE: DNA
<213> ORGANISM: Artificial Sequence
<220> FEATURE:
<223> OTHER INFORMATION: Synthetic

<400> SEQUENCE: 15
atggtgcgct tgtacgtgtt ggtaatggga gtttctgcct tcacccttca gcctgcggca      60
cacacagggg ctgccagaag ctgccggttt cgtgggaggc attacaagcg ggagttcagg     120
ctggaagggg agcctgtagc cctgaggtgc ccccaggtgc cctactggtt gtgggcctct     180
gtcagccccc gcatcaacct gacatggcat aaaaatgact ctgctaggac ggtcccagga     240
gaagaagaga cacggatgtg ggcccaggac ggtgctctgt ggcttctgcc agccttgcag     300
gaggactctg gcacctacgt ctgcactact agaaatgctt cttactgtga caaatgtcc      360 attgagctca gagtttttga gaatacagat gctttcctgc cgttcatctc ataccccgcaa    420 attttaacct tgtcaaccct tggggtatta gtatgccctg acctgagtga attcacccgt     480
gacaaaactg acgtgaagat tcaatggtac aaggattctc ttcttttgga taagacaat      540 gagaaatttc taagtgtgag ggggaccact cacttactcg tacacgatgt ggccctggaa     600
gatgctggct attaccgctg tgtcctgaca tttgcccatg aaggccagca atacaacatc     660
actaggagta ttgagctacg catcaagaaa aaaaagaag agaccattcc tgtgatcatt      720

-continued

```
tcccccctca agaccatatc agcttctctg gggtcaagac tgacaatccc atgtaaggtg    780
tttctgggaa ccggcacacc cttaaccacc atgctgtggt ggacggccaa tgacacccac    840
atagagagcg cctacccggg aggccgcgtg accgagggc cacgccagga atattcagaa     900
aataatgaga actacattga agtgccattg atttttgatc ctgtcacaag agaggatttg    960
cacatggatt taaatgtgt tgtccataat accctgagtt ttcagacact acgcaccaca    1020
gtcaaggaag cctcctccac gttctcagaa cgctgcgatg actggggact agacaccatg   1080
aggcaaatcc aagtgtttga agatgagcca gctcgcatca agtgcccact ctttgaacac   1140
ttcttgaaat tcaactacag cacagcccat tcagctggcc ttactctgat ctggtattgg   1200
actaggcagg accgggacct tgaggagcca attaacttcc gcctcccga gaaccgcatt    1260 agtaaggaga aagatgtgct gtggttccgg cccactctcc tcaatgacac tggcaactat   1320
acctgcatgt taaggaacac tacatattgc agcaaagttg catttccctt ggaagttgtt   1380 caaaagaca gctgtttcaa ttcccccatg aaactcccag tgcataaact gtatatagaa    1440
tatggcattc agaggatcac ttgtccaaat gtagatggat attttccttc cagtgtcaaa   1500
ccgactatca cttggtatat gggctgttat aaaatacaga attttaataa tgtaataccc   1560
gaaggtatga acttgagttt cctcattgcc ttaatttcaa ataatggaaa ttacacatgt   1620
gttgttacat atccagaaaa tggacgtacg tttcatctca ccaggactct gactgtaaag   1680
gtagtaggct ctccaaaaaa tgcagtgccc cctgtgatcc attcacctaa tgatcatgtg   1740
gtctatgaga agaaccagg agaggagcta ctcattccct gtacggtcta ttttagtttt    1800
ctgatggatt ctcgcaatga ggtttggtgg accattgatg gaaaaaaacc tgatgacatc   1860
actattgatg tcaccattaa cgaaagtata agtcatagta aacagaaga tgaaacaaga    1920 actcagattt tgagcatcaa gaaagttacc tctgaggatc tcaagcgcag ctatgtctgt   1980
catgctagaa gtgccaaagg cgaagttgcc aaagcagcca aggtgaagca gaaagtgcca   2040
gctccaagat acacagtgtc cggagacaaa actcacacat gcccaccgtg cccagcacct   2100
gaactcctgg gggaccgtc agtcttcctc ttccccccaa acccaagga caccctcatg    2160 atctcccgga ccctgaggt cacatgcgtg gtggtggacg tgagccacga agaccctgag   2220
gtcaagttca actggtacgt ggacggcgtg gaggtgcata atgccaagac aaagccgcgg   2280
gaggagcagt acaacagcac gtaccgtgtg gtcagcgtcc tcaccgtcct gcaccaggac   2340
tggctgaatg gcaaggagta caagtgcaag gtctccaaca aagccctccc agcccccatc   2400
gagaaaacca tctccaaagc caaagggcag ccccgagaac acaggtgta caccctgccc    2460 ccatcccggg atgagctgac caagaaccag gtcagcctga cctgcctggt caaaggcttc   2520
tatcccagcg acatcgccgt ggagtgggag agcaatgggc agccggagaa caactacaag   2580
accacgcctc ccgtgctgga ctccgacggc tccttcttcc tctatagcaa gctcaccgtg   2640
gacaagagca ggtggcagca ggggaacgtc ttctcatgct ccgtgatgca tgaggctctg   2700
cacaaccact acacgcagaa gagcctctcc ctgtctccgg gtaaatga                2748
```

<210> SEQ ID NO 16
<211> LENGTH: 915
<212> TYPE: PRT
<213> ORGANISM: Artificial Sequence
<220> FEATURE:
<223> OTHER INFORMATION: Synthetic

<400> SEQUENCE: 16

-continued

```
Met Val Arg Leu Tyr Val Leu Val Met Gly Val Ser Ala Phe Thr Leu
 1               5                  10                  15

Gln Pro Ala Ala His Thr Gly Ala Ala Arg Ser Cys Arg Phe Arg Gly
             20                  25                  30

Arg His Tyr Lys Arg Glu Phe Arg Leu Glu Gly Glu Pro Val Ala Leu
                 35                  40                  45

Arg Cys Pro Gln Val Pro Tyr Trp Leu Trp Ala Ser Val Ser Pro Arg
 50                  55                  60

Ile Asn Leu Thr Trp His Lys Asn Asp Ser Ala Arg Thr Val Pro Gly
 65                  70                  75                  80

Glu Glu Thr Arg Met Trp Ala Gln Asp Gly Ala Leu Trp Leu Leu
                 85                  90                  95

Pro Ala Leu Gln Glu Asp Ser Gly Thr Tyr Val Cys Thr Thr Arg Asn
             100                 105                 110

Ala Ser Tyr Cys Asp Lys Met Ser Ile Glu Leu Arg Val Phe Glu Asn
             115                 120                 125

Thr Asp Ala Phe Leu Pro Phe Ile Ser Tyr Pro Gln Ile Leu Thr Leu
 130                 135                 140

Ser Thr Ser Gly Val Leu Val Cys Pro Asp Leu Ser Glu Phe Thr Arg
145                  150                 155                 160

Asp Lys Thr Asp Val Lys Ile Gln Trp Tyr Lys Asp Ser Leu Leu Leu
                 165                 170                 175

Asp Lys Asp Asn Glu Lys Phe Leu Ser Val Arg Gly Thr Thr His Leu
             180                 185                 190

Leu Val His Asp Val Ala Leu Glu Asp Ala Gly Tyr Tyr Arg Cys Val
             195                 200                 205

Leu Thr Phe Ala His Glu Gly Gln Gln Tyr Asn Ile Thr Arg Ser Ile
 210                 215                 220

Glu Leu Arg Ile Lys Lys Lys Glu Thr Ile Pro Val Ile
225                  230                 235                 240

Ser Pro Leu Lys Thr Ile Ser Ala Ser Leu Gly Ser Arg Leu Thr Ile
                 245                 250                 255

Pro Cys Lys Val Phe Leu Gly Thr Gly Thr Pro Leu Thr Thr Met Leu
             260                 265                 270

Trp Trp Thr Ala Asn Asp Thr His Ile Glu Ser Ala Tyr Pro Gly Gly
             275                 280                 285

Arg Val Thr Glu Gly Pro Arg Gln Glu Tyr Ser Glu Asn Asn Glu Asn
 290                 295                 300

Tyr Ile Glu Val Pro Leu Ile Phe Asp Pro Val Thr Arg Glu Asp Leu
305                  310                 315                 320

His Met Asp Phe Lys Cys Val Val His Asn Thr Leu Ser Phe Gln Thr
                 325                 330                 335

Leu Arg Thr Thr Val Lys Glu Ala Ser Ser Thr Phe Ser Glu Arg Cys
             340                 345                 350

Asp Asp Trp Gly Leu Asp Thr Met Arg Gln Ile Gln Val Phe Glu Asp
             355                 360                 365

Glu Pro Ala Arg Ile Lys Cys Pro Leu Phe Glu His Phe Leu Lys Phe
 370                 375                 380

Asn Tyr Ser Thr Ala His Ser Ala Gly Leu Thr Leu Ile Trp Tyr Trp
385                  390                 395                 400

Thr Arg Gln Asp Arg Asp Leu Glu Glu Pro Ile Asn Phe Arg Leu Pro
                 405                 410                 415

Glu Asn Arg Ile Ser Lys Glu Lys Asp Val Leu Trp Phe Arg Pro Thr
```

```
                420             425             430
Leu Leu Asn Asp Thr Gly Asn Tyr Thr Cys Met Leu Arg Asn Thr Thr
        435                 440             445

Tyr Cys Ser Lys Val Ala Phe Pro Leu Glu Val Val Gln Lys Asp Ser
    450                 455             460

Cys Phe Asn Ser Pro Met Lys Leu Pro Val His Lys Leu Tyr Ile Glu
465                 470             475             480

Tyr Gly Ile Gln Arg Ile Thr Cys Pro Asn Val Asp Gly Tyr Phe Pro
                485             490             495

Ser Ser Val Lys Pro Thr Ile Thr Trp Tyr Met Gly Cys Tyr Lys Ile
            500             505             510

Gln Asn Phe Asn Asn Val Ile Pro Glu Gly Met Asn Leu Ser Phe Leu
        515             520             525

Ile Ala Leu Ile Ser Asn Asn Gly Asn Tyr Thr Cys Val Val Thr Tyr
    530             535             540

Pro Glu Asn Gly Arg Thr Phe His Leu Thr Arg Thr Leu Thr Val Lys
545             550             555             560

Val Val Gly Ser Pro Lys Asn Ala Val Pro Pro Val Ile His Ser Pro
                565             570             575

Asn Asp His Val Val Tyr Glu Lys Glu Pro Gly Glu Glu Leu Leu Ile
            580             585             590

Pro Cys Thr Val Tyr Phe Ser Phe Leu Met Asp Ser Arg Asn Glu Val
        595             600             605

Trp Trp Thr Ile Asp Gly Lys Lys Pro Asp Asp Ile Thr Ile Asp Val
    610             615             620

Thr Ile Asn Glu Ser Ile Ser His Ser Arg Thr Glu Asp Glu Thr Arg
625             630             635             640

Thr Gln Ile Leu Ser Ile Lys Lys Val Thr Ser Glu Asp Leu Lys Arg
                645             650             655

Ser Tyr Val Cys His Ala Arg Ser Ala Lys Gly Glu Val Ala Lys Ala
            660             665             670

Ala Lys Val Lys Gln Lys Val Pro Ala Pro Arg Tyr Thr Val Ser Gly
        675             680             685

Asp Lys Thr His Thr Cys Pro Pro Cys Pro Ala Pro Glu Leu Leu Gly
    690             695             700

Gly Pro Ser Val Phe Leu Phe Pro Pro Lys Pro Lys Asp Thr Leu Met
705             710             715             720

Ile Ser Arg Thr Pro Glu Val Thr Cys Val Val Val Asp Val Ser His
                725             730             735

Glu Asp Pro Glu Val Lys Phe Asn Trp Tyr Val Asp Gly Val Glu Val
            740             745             750

His Asn Ala Lys Thr Lys Pro Arg Glu Glu Gln Tyr Asn Ser Thr Tyr
        755             760             765

Arg Val Val Ser Val Leu Thr Val Leu His Gln Asp Trp Leu Asn Gly
    770             775             780

Lys Glu Tyr Lys Cys Lys Val Ser Asn Lys Ala Leu Pro Ala Pro Ile
785             790             795             800

Glu Lys Thr Ile Ser Lys Ala Lys Gly Gln Pro Arg Glu Pro Gln Val
                805             810             815

Tyr Thr Leu Pro Pro Ser Arg Asp Glu Leu Thr Lys Asn Gln Val Ser
            820             825             830

Leu Thr Cys Leu Val Lys Gly Phe Tyr Pro Ser Asp Ile Ala Val Glu
        835             840             845
```

```
Trp Glu Ser Asn Gly Gln Pro Glu Asn Asn Tyr Lys Thr Thr Pro Pro
    850                 855                 860

Val Leu Asp Ser Asp Gly Ser Phe Phe Leu Tyr Ser Lys Leu Thr Val
865                 870                 875                 880

Asp Lys Ser Arg Trp Gln Gln Gly Asn Val Phe Ser Cys Ser Val Met
                885                 890                 895

His Glu Ala Leu His Asn His Tyr Thr Gln Lys Ser Leu Ser Leu Ser
            900                 905                 910

Pro Gly Lys
        915

<210> SEQ ID NO 17
<211> LENGTH: 2754
<212> TYPE: DNA
<213> ORGANISM: Artificial Sequence
<220> FEATURE:
<223> OTHER INFORMATION: Synthetic

<400> SEQUENCE: 17
```

| | | | | | |
|---|---|---|---|---|---|
| atggtgcgct | tgtacgtgtt | ggtaatggga | gtttctgcct | tcacccttca | gcctgcggca | 60 |
| cacacagggg | ctgccagaag | ctgccggttt | cgtgggaggc | attacaagcg | ggagttcagg | 120 |
| ctggaagggg | agcctgtagc | cctgaggtgc | cccaggtgc | cctactggtt | gtgggcctct | 180 |
| gtcagccccc | gcatcaacct | gacatggcat | aaaaatgact | ctgctaggac | ggtcccagga | 240 |
| gaagaagaga | cacggatgtg | ggcccaggac | ggtgctctgt | ggcttctgcc | agccttgcag | 300 |
| gaggactctg | gcacctacgt | ctgcactact | agaaatgctt | cttactgtga | caaaatgtcc | 360 |
| attgagctca | gagtttttga | gaatacagat | gctttcctgc | cgttcatctc | ataccccgcaa | 420 |
| attttaacct | tgtcaacctc | tggggtatta | gtatgccctg | acctgagtga | attcacccgt | 480 |
| gacaaaactg | acgtgaagat | tcaatggtac | aaggattctc | ttcttttgga | taaagacaat | 540 |
| gagaaatttc | taagtgtgag | ggggaccact | cacttactcg | tacacgatgt | ggccctggaa | 600 |
| gatgctggct | attaccgctg | tgtcctgaca | tttgcccatg | aaggccagca | atacaacatc | 660 |
| actaggagta | ttgagctacg | catcaagaaa | aaaaagaag | agaccattcc | tgtgatcatt | 720 |
| tccccctca | agaccatatc | agcttctctg | gggtcaagac | tgacaatccc | atgtaaggtg | 780 |
| tttctgggaa | ccggcacacc | cttaaccacc | atgctgtggt | ggacggccaa | tgacacccac | 840 |
| atagagagcg | cctacccggg | aggccgcgtg | accgagggc | cacgccagga | atattcagaa | 900 |
| aataatgaga | actacattga | agtgccattg | attttgatc | ctgtcacaag | agaggatttg | 960 |
| cacatggatt | ttaaatgtgt | tgtccataat | accctgagtt | ttcagacact | acgcaccaca | 1020 |
| gtcaaggaag | cctcctccac | gttctcagaa | cgctgcgatg | actggggact | agacaccatg | 1080 |
| aggcaaatcc | aagtgtttga | agatgagcca | gctcgcatca | gtgcccact | ctttgaacac | 1140 |
| ttcttgaaat | tcaactacag | cacagcccat | tcagctggcc | ttactctgat | ctggtattgg | 1200 |
| actaggcagg | accgggacct | tgaggagcca | attaacttcc | gcctccccga | gaaccgcatt | 1260 |
| agtaaggaga | aagatgtgct | gtggttccgg | cccactctcc | tcaatgacac | tggcaactat | 1320 |
| acctgcatgt | taaggaacac | tacatattgc | agcaaagttg | catttccctt | ggaagttgtt | 1380 |
| caaaaagaca | gctgtttcaa | ttcccccatg | aaactcccag | tgcataaact | gtatatagaa | 1440 |
| tatggcattc | agaggatcac | ttgtccaaat | gtagatggat | attttccttc | cagtgtcaaa | 1500 |
| ccgactatca | cttggtatat | gggctgttat | aaaaatacaga | attttaataa | tgtaataccc | 1560 |
| gaaggtatga | acttgagttt | cctccattgcc | ttaatttcaa | ataatggaaa | ttacacatgt | 1620 |

```
gttgttacat atccagaaaa tggacgtacg tttcatctca ccaggactct gactgtaaag    1680
gtagtaggct ctccaaaaaa tgcagtgccc cctgtgatcc attcacctaa tgatcatgtg    1740
gtctatgaga aagaaccagg agaggagcta ctcattccct gtacggtcta ttttagtttt    1800
ctgatggatt ctcgcaatga ggtttggtgg accattgatg gaaaaaaacc tgatgacatc    1860
actattgatg tcaccattaa cgaaagtata agtcatagta gaacagaaga tgaaacaaga    1920
actcagattt tgagcatcaa gaaagttacc tctgaggatc tcaagcgcag ctatgtctgt    1980
catgctagaa gtgccaaagg cgaagttgcc aaagcagcca aggtgaagca gaaagtgcca    2040
gctccaagat acacagtgtc cggagagtcc aaatacggtc cgccatgccc atcatgccca    2100
gcacctgagt tcctgggggg accatcagtc ttcctgttcc ccccaaaacc caaggacact    2160
ctcatgatct cccggacccc tgaggtcacg tgcgtggtgg tggacgtgag ccaggaagac    2220
cccgaggtcc agttcaactg gtacgtggat ggcgtggagg tgcataatgc caagacaaag    2280
ccgcgggagg agcagttcaa cagcacgtac cgtgtggtca gcgtcctcac cgtcctgcac    2340
caggactggc tgaacggcaa ggagtacaag tgcaaggtct ccaacaaagg cctcccgtcc    2400
tccatcgaga aaaccatctc caaagccaaa gggcagcccc gagagccaca ggtgtacacc    2460
ctgcccccat cccaggagga tgaccaag aaccaggtca gcctgacctg cctggtcaaa     2520
ggcttctacc ccagcgacat cgccgtggag tgggagagca atgggcagcc ggagaacaac    2580
tacaagacca cgcctcccgt gctggactcc gacggctcct tcttcctcta cagcaggcta    2640
accgtggaca agagcaggtg gcaggagggg aatgtcttct catgctccgt gatgcatgag    2700
gctctgcaca accactacac acagaagagc ctctccctgt ctctgggtaa atga         2754
```

<210> SEQ ID NO 18
<211> LENGTH: 917
<212> TYPE: PRT
<213> ORGANISM: Artificial Sequence
<220> FEATURE:
<223> OTHER INFORMATION: Synthetic

<400> SEQUENCE: 18

```
Met Val Arg Leu Tyr Val Leu Val Met Gly Val Ser Ala Phe Thr Leu
 1               5                  10                  15

Gln Pro Ala Ala His Thr Gly Ala Ala Arg Ser Cys Arg Phe Arg Gly
            20                  25                  30

Arg His Tyr Lys Arg Glu Phe Arg Leu Glu Gly Glu Pro Val Ala Leu
        35                  40                  45

Arg Cys Pro Gln Val Pro Tyr Trp Leu Trp Ala Ser Val Ser Pro Arg
    50                  55                  60

Ile Asn Leu Thr Trp His Lys Asn Asp Ser Ala Arg Thr Val Pro Gly
65                  70                  75                  80

Glu Glu Glu Thr Arg Met Trp Ala Gln Asp Gly Ala Leu Trp Leu Leu
                85                  90                  95

Pro Ala Leu Gln Glu Asp Ser Gly Thr Tyr Val Cys Thr Thr Arg Asn
            100                 105                 110

Ala Ser Tyr Cys Asp Lys Met Ser Ile Glu Leu Arg Val Phe Glu Asn
        115                 120                 125

Thr Asp Ala Phe Leu Pro Phe Ile Ser Tyr Pro Gln Ile Leu Thr Leu
    130                 135                 140

Ser Thr Ser Gly Val Leu Val Cys Pro Asp Leu Ser Glu Phe Thr Arg
145                 150                 155                 160
```

-continued

```
Asp Lys Thr Asp Val Lys Ile Gln Trp Tyr Lys Asp Ser Leu Leu Leu
            165                 170                 175

Asp Lys Asp Asn Glu Lys Phe Leu Ser Val Arg Gly Thr Thr His Leu
            180                 185                 190

Leu Val His Asp Val Ala Leu Glu Asp Ala Gly Tyr Tyr Arg Cys Val
            195                 200                 205

Leu Thr Phe Ala His Glu Gly Gln Gln Tyr Asn Ile Thr Arg Ser Ile
            210                 215                 220

Glu Leu Arg Ile Lys Lys Lys Glu Glu Thr Ile Pro Val Ile Ile
225                 230                 235                 240

Ser Pro Leu Lys Thr Ile Ser Ala Ser Leu Gly Ser Arg Leu Thr Ile
            245                 250                 255

Pro Cys Lys Val Phe Leu Gly Thr Gly Thr Pro Leu Thr Thr Met Leu
            260                 265                 270

Trp Trp Thr Ala Asn Asp Thr His Ile Glu Ser Ala Tyr Pro Gly Gly
            275                 280                 285

Arg Val Thr Glu Gly Pro Arg Gln Glu Tyr Ser Glu Asn Asn Glu Asn
            290                 295                 300

Tyr Ile Glu Val Pro Leu Ile Phe Asp Pro Val Thr Arg Glu Asp Leu
305                 310                 315                 320

His Met Asp Phe Lys Cys Val Val His Asn Thr Leu Ser Phe Gln Thr
            325                 330                 335

Leu Arg Thr Thr Val Lys Glu Ala Ser Ser Thr Phe Ser Glu Arg Cys
            340                 345                 350

Asp Asp Trp Gly Leu Asp Thr Met Arg Gln Ile Gln Val Phe Glu Asp
            355                 360                 365

Glu Pro Ala Arg Ile Lys Cys Pro Leu Phe Glu His Phe Leu Lys Phe
            370                 375                 380

Asn Tyr Ser Thr Ala His Ser Ala Gly Leu Thr Leu Ile Trp Tyr Trp
385                 390                 395                 400

Thr Arg Gln Asp Arg Asp Leu Glu Glu Pro Ile Asn Phe Arg Leu Pro
            405                 410                 415

Glu Asn Arg Ile Ser Lys Glu Lys Asp Val Leu Trp Phe Arg Pro Thr
            420                 425                 430

Leu Leu Asn Asp Thr Gly Asn Tyr Thr Cys Met Leu Arg Asn Thr Thr
            435                 440                 445

Tyr Cys Ser Lys Val Ala Phe Pro Leu Glu Val Val Gln Lys Asp Ser
            450                 455                 460

Cys Phe Asn Ser Pro Met Lys Leu Pro Val His Lys Leu Tyr Ile Glu
465                 470                 475                 480

Tyr Gly Ile Gln Arg Ile Thr Cys Pro Asn Val Asp Gly Tyr Phe Pro
            485                 490                 495

Ser Ser Val Lys Pro Thr Ile Thr Trp Tyr Met Gly Cys Tyr Lys Ile
            500                 505                 510

Gln Asn Phe Asn Asn Val Ile Pro Glu Gly Met Asn Leu Ser Phe Leu
            515                 520                 525

Ile Ala Leu Ile Ser Asn Asn Gly Asn Tyr Thr Cys Val Val Thr Tyr
            530                 535                 540

Pro Glu Asn Gly Arg Thr Phe His Leu Thr Arg Thr Leu Thr Val Lys
545                 550                 555                 560

Val Val Gly Ser Pro Lys Asn Ala Val Pro Pro Val Ile His Ser Pro
            565                 570                 575

Asn Asp His Val Val Tyr Glu Lys Glu Pro Gly Glu Glu Leu Leu Ile
```

-continued

```
                580             585             590
Pro Cys Thr Val Tyr Phe Ser Phe Leu Met Asp Ser Arg Asn Glu Val
            595                 600                 605
Trp Trp Thr Ile Asp Gly Lys Lys Pro Asp Asp Ile Thr Ile Asp Val
            610                 615                 620
Thr Ile Asn Glu Ser Ile Ser His Ser Arg Thr Glu Asp Glu Thr Arg
625                 630                 635                 640
Thr Gln Ile Leu Ser Ile Lys Lys Val Thr Ser Glu Asp Leu Lys Arg
                645                 650                 655
Ser Tyr Val Cys His Ala Arg Ser Ala Lys Gly Glu Val Ala Lys Ala
            660                 665                 670
Ala Lys Val Lys Gln Lys Val Pro Ala Pro Arg Tyr Thr Val Ser Gly
            675                 680                 685
Glu Ser Lys Tyr Gly Pro Pro Cys Pro Ser Cys Pro Ala Pro Glu Phe
            690                 695                 700
Leu Gly Gly Pro Ser Val Phe Leu Phe Pro Pro Lys Pro Lys Asp Thr
705                 710                 715                 720
Leu Met Ile Ser Arg Thr Pro Glu Val Thr Cys Val Val Val Asp Val
                725                 730                 735
Ser Gln Glu Asp Pro Glu Val Gln Phe Asn Trp Tyr Val Asp Gly Val
            740                 745                 750
Glu Val His Asn Ala Lys Thr Lys Pro Arg Glu Glu Gln Phe Asn Ser
            755                 760                 765
Thr Tyr Arg Val Val Ser Val Leu Thr Val Leu His Gln Asp Trp Leu
            770                 775                 780
Asn Gly Lys Glu Tyr Lys Cys Lys Val Ser Asn Lys Gly Leu Pro Ser
785                 790                 795                 800
Ser Ile Glu Lys Thr Ile Ser Lys Ala Lys Gly Gln Pro Arg Glu Pro
                805                 810                 815
Gln Val Tyr Thr Leu Pro Pro Ser Gln Glu Met Thr Lys Asn Gln
            820                 825                 830
Val Ser Leu Thr Cys Leu Val Lys Gly Phe Tyr Pro Ser Asp Ile Ala
            835                 840                 845
Val Glu Trp Glu Ser Asn Gly Gln Pro Glu Asn Asn Tyr Lys Thr Thr
            850                 855                 860
Pro Pro Val Leu Asp Ser Asp Gly Ser Phe Phe Leu Tyr Ser Arg Leu
865                 870                 875                 880
Thr Val Asp Lys Ser Arg Trp Gln Glu Gly Asn Val Phe Ser Cys Ser
                885                 890                 895
Val Met His Glu Ala Leu His Asn His Tyr Thr Gln Lys Ser Leu Ser
            900                 905                 910
Leu Ser Leu Gly Lys
        915

<210> SEQ ID NO 19
<211> LENGTH: 2754
<212> TYPE: DNA
<213> ORGANISM: Artificial Sequence
<220> FEATURE:
<223> OTHER INFORMATION: Synthetic

<400> SEQUENCE: 19
atggtgcgct tgtacgtgtt ggtaatggga gtttctgcct tcacccttca gcctgcggca      60
cacacagggg ctgccagaag ctgccggttt cgtgggaggc attacaagcg ggagttcagg     120
```

```
ctggaagggg agcctgtagc cctgaggtgc ccccaggtgc cctactggtt gtgggcctct      180
gtcagccccc gcatcaacct gacatggcat aaaaatgact ctgctaggac ggtcccagga      240
gaagaagaga cacggatgtg ggcccaggac ggtgctctgt ggcttctgcc agccttgcag      300
gaggactctg gcacctacgt ctgcactact agaaatgctt cttactgtga caaaatgtcc      360
attgagctca gagttttga gaatacagat gctttcctgc cgttcatctc atacccgcaa       420
attttaacct tgtcaacctc tggggtatta gtatgccctg acctgagtga attcacccgt      480
gacaaaactg acgtgaagat tcaatggtac aaggattctc ttcttttgga taaagacaat      540
gagaaatttc taagtgtgag ggggaccact cacttactcg tacacgatgt ggccctggaa      600
gatgctggct attaccgctg tgtcctgaca tttgcccatg aaggccagca atacaacatc      660
actaggagta ttgagctacg catcaagaaa aaaaagaag agaccattcc tgtgatcatt       720 tccccctca agaccatatc agcttctctg gggtcaagac tgacaatccc atgtaaggtg      780
tttctgggaa ccgcacacc cttaaccacc atgctgtggt ggacggccaa tgacacccac      840
atagagagcg cctacccggg aggccgcgtg accgaggggc cacgccagga atattcagaa      900
aataatgaga actacattga agtgccattg attttgatc ctgtcacaag agaggatttg       960
cacatggatt ttaaatgtgt tgtccataat accctgagtt ttcagacact acgcaccaca     1020
gtcaaggaag cctcctccac gttctcagaa cgctgcgatg actggggact agacaccatg     1080
aggcaaatcc aagtgtttga agatgagcca gctcgcatca agtgcccact ctttgaacac     1140
ttcttgaaat tcaactacag cacagcccat tcagctggcc ttactctgat ctggtattgg     1200
actaggcagg accgggacct tgaggagcca attaacttcc gcctccccga gaaccgcatt     1260
agtaaggaga aagatgtgct gtggttccgg cccactctcc tcaatgacac tggcaactat     1320
acctgcatgt taggaacac tacatattgc agcaaagttg catttccctt ggaagttgtt      1380
caaaaagaca gctgtttcaa ttcccccatg aaactcccag tgcataaact gtatatagaa     1440
tatggcattc agaggatcac ttgtccaaat gtagatggat attttccttc cagtgtcaaa     1500
ccgactatca cttggtatat gggctgttat aaaatacaga atttaataa tgtaataccc      1560 gaaggtatga acttgagttt cctcattgcc ttaatttcaa ataatggaaa ttacacatgt     1620
gttgttacat atccagaaaa tggacgtacg tttcatctca ccaggactct gactgtaaag     1680
gtagtaggct ctccaaaaaa tgcagtgccc cctgtgatcc attcacctaa tgatcatgtg     1740
gtctatgaga aagaaccagg agaggagcta ctcattccct gtacggtcta ttttagtttt     1800
ctgatggatt ctcgcaatga ggtttggtgg accattgatg gaaaaaaacc tgatgacatc     1860
actattgatg tcaccattaa cgaaagtata agtcatagta acagaaga tgaaacaaga       1920 actcagattt tgagcatcaa gaaagttacc tctgaggatc tcaagcgcag ctatgtctgt     1980
catgctagaa gtgccaaagg cgaagttgcc aaagcagcca aggtgaagca gaaagtgcca     2040
gctccaagat acacagtgtc cggagagtcc aaatacggtc cgccatgccc accatgccca     2100
gcacctgagt tcctgggggg accatcagtc ttcctgttcc ccccaaaacc caaggacact     2160
ctcatgatct cccggacccc tgaggtcacg tgcgtggtgg tggacgtgag ccaggaagac     2220
cccgaggtcc agttcaactg gtacgtggat ggcgtggagg tgcataatgc caagacaaag     2280
ccgcgggagg agcagttcaa cagcacgtac cgtgtggtca gcgtcctcac cgtcctgcac     2340
caggactggc tgaacggcaa ggagtacaag tgcaaggtct ccaacaaagg cctcccgtcc     2400
tccatcgaga aaaccatctc caaagccaaa gggcagcccc gagagccaca ggtgtacacc     2460
ctgcccccat cccaggagga gatgaccaag aaccaggtca gcctgacctg cctggtcaaa     2520
```

-continued

```
ggcttctacc ccagcgacat cgccgtggag tgggagagca atgggcagcc ggagaacaac    2580
tacaagacca cgcctcccgt gctggactcc gacggctcct tcttcctcta cagcaggcta    2640
accgtggaca agagcaggtg gcaggagggg aatgtcttct catgctccgt gatgcatgag    2700
gctctgcaca accactacac acagaagagc ctctccctgt ctctgggtaa atga          2754
```

<210> SEQ ID NO 20
<211> LENGTH: 917
<212> TYPE: PRT
<213> ORGANISM: Artificial Sequence
<220> FEATURE:
<223> OTHER INFORMATION: Synthetic

<400> SEQUENCE: 20

```
Met Val Arg Leu Tyr Val Leu Val Met Gly Val Ala Phe Thr Leu
 1               5                  10                  15

Gln Pro Ala Ala His Thr Gly Ala Ala Arg Ser Cys Arg Phe Arg Gly
            20                  25                  30

Arg His Tyr Lys Arg Glu Phe Arg Leu Glu Gly Glu Pro Val Ala Leu
        35                  40                  45

Arg Cys Pro Gln Val Pro Tyr Trp Leu Trp Ala Ser Val Ser Pro Arg
    50                  55                  60

Ile Asn Leu Thr Trp His Lys Asn Asp Ser Ala Arg Thr Val Pro Gly
65                  70                  75                  80

Glu Glu Glu Thr Arg Met Trp Ala Gln Asp Gly Ala Leu Trp Leu Leu
                85                  90                  95

Pro Ala Leu Gln Glu Asp Ser Gly Thr Tyr Val Cys Thr Thr Arg Asn
            100                 105                 110

Ala Ser Tyr Cys Asp Lys Met Ser Ile Glu Leu Arg Val Phe Glu Asn
        115                 120                 125

Thr Asp Ala Phe Leu Pro Phe Ile Ser Tyr Pro Gln Ile Leu Thr Leu
    130                 135                 140

Ser Thr Ser Gly Val Leu Val Cys Pro Asp Leu Ser Glu Phe Thr Arg
145                 150                 155                 160

Asp Lys Thr Asp Val Lys Ile Gln Trp Tyr Lys Asp Ser Leu Leu Leu
                165                 170                 175

Asp Lys Asp Asn Glu Lys Phe Leu Ser Val Arg Gly Thr Thr His Leu
            180                 185                 190

Leu Val His Asp Val Ala Leu Glu Asp Ala Gly Tyr Tyr Arg Cys Val
        195                 200                 205

Leu Thr Phe Ala His Glu Gly Gln Gln Tyr Asn Ile Thr Arg Ser Ile
    210                 215                 220

Glu Leu Arg Ile Lys Lys Lys Glu Glu Thr Ile Pro Val Ile Ile
225                 230                 235                 240

Ser Pro Leu Lys Thr Ile Ser Ala Ser Leu Gly Ser Arg Leu Thr Ile
                245                 250                 255

Pro Cys Lys Val Phe Leu Gly Thr Gly Thr Pro Leu Thr Thr Met Leu
            260                 265                 270

Trp Trp Thr Ala Asn Asp Thr His Ile Glu Ser Ala Tyr Pro Gly Gly
        275                 280                 285

Arg Val Thr Glu Gly Pro Arg Gln Glu Tyr Ser Glu Asn Asn Glu Asn
    290                 295                 300

Tyr Ile Glu Val Pro Leu Ile Phe Asp Pro Val Thr Arg Glu Asp Leu
305                 310                 315                 320
```

-continued

```
His Met Asp Phe Lys Cys Val Val His Asn Thr Leu Ser Phe Gln Thr
            325                 330                 335

Leu Arg Thr Thr Val Lys Glu Ala Ser Ser Thr Phe Ser Glu Arg Cys
            340                 345                 350

Asp Asp Trp Gly Leu Asp Thr Met Arg Gln Ile Gln Val Phe Glu Asp
            355                 360                 365

Glu Pro Ala Arg Ile Lys Cys Pro Leu Phe Glu His Phe Leu Lys Phe
370                 375                 380

Asn Tyr Ser Thr Ala His Ser Ala Gly Leu Thr Leu Ile Trp Tyr Trp
385                 390                 395                 400

Thr Arg Gln Asp Arg Asp Leu Glu Glu Pro Ile Asn Phe Arg Leu Pro
                405                 410                 415

Glu Asn Arg Ile Ser Lys Glu Lys Asp Val Leu Trp Phe Arg Pro Thr
            420                 425                 430

Leu Leu Asn Asp Thr Gly Asn Tyr Thr Cys Met Leu Arg Asn Thr Thr
            435                 440                 445

Tyr Cys Ser Lys Val Ala Phe Pro Leu Glu Val Val Gln Lys Asp Ser
    450                 455                 460

Cys Phe Asn Ser Pro Met Lys Leu Pro Val His Lys Leu Tyr Ile Glu
465                 470                 475                 480

Tyr Gly Ile Gln Arg Ile Thr Cys Pro Asn Val Asp Gly Tyr Phe Pro
                485                 490                 495

Ser Ser Val Lys Pro Thr Ile Thr Trp Tyr Met Gly Cys Tyr Lys Ile
            500                 505                 510

Gln Asn Phe Asn Asn Val Ile Pro Glu Gly Met Asn Leu Ser Phe Leu
            515                 520                 525

Ile Ala Leu Ile Ser Asn Asn Gly Asn Tyr Thr Cys Val Val Thr Tyr
            530                 535                 540

Pro Glu Asn Gly Arg Thr Phe His Leu Thr Arg Thr Leu Thr Val Lys
545                 550                 555                 560

Val Val Gly Ser Pro Lys Asn Ala Val Pro Pro Val Ile His Ser Pro
                565                 570                 575

Asn Asp His Val Val Tyr Glu Lys Glu Pro Gly Glu Glu Leu Leu Ile
            580                 585                 590

Pro Cys Thr Val Tyr Phe Ser Phe Leu Met Asp Ser Arg Asn Glu Val
            595                 600                 605

Trp Trp Thr Ile Asp Gly Lys Lys Pro Asp Asp Ile Thr Ile Asp Val
            610                 615                 620

Thr Ile Asn Glu Ser Ile Ser His Ser Arg Thr Glu Asp Glu Thr Arg
625                 630                 635                 640

Thr Gln Ile Leu Ser Ile Lys Lys Val Thr Ser Glu Asp Leu Lys Arg
                645                 650                 655

Ser Tyr Val Cys His Ala Arg Ser Ala Lys Gly Glu Val Ala Lys Ala
            660                 665                 670

Ala Lys Val Lys Gln Lys Val Pro Ala Pro Arg Tyr Thr Val Ser Gly
            675                 680                 685

Glu Ser Lys Tyr Gly Pro Pro Cys Pro Pro Cys Pro Ala Pro Glu Phe
            690                 695                 700

Leu Gly Gly Pro Ser Val Phe Leu Phe Pro Pro Lys Pro Lys Asp Thr
705                 710                 715                 720

Leu Met Ile Ser Arg Thr Pro Glu Val Thr Cys Val Val Val Asp Val
                725                 730                 735

Ser Gln Glu Asp Pro Glu Val Gln Phe Asn Trp Tyr Val Asp Gly Val
```

```
                740                   745                    750
Glu Val His Asn Ala Lys Thr Lys Pro Arg Glu Gln Phe Asn Ser
            755                  760                765

Thr Tyr Arg Val Val Ser Val Leu Thr Val Leu His Gln Asp Trp Leu
        770                  775                  780

Asn Gly Lys Glu Tyr Lys Cys Lys Val Ser Asn Lys Gly Leu Pro Ser
785                 790                  795                 800

Ser Ile Glu Lys Thr Ile Ser Lys Ala Lys Gly Gln Pro Arg Glu Pro
                805                  810                 815

Gln Val Tyr Thr Leu Pro Pro Ser Gln Glu Glu Met Thr Lys Asn Gln
            820                  825                 830

Val Ser Leu Thr Cys Leu Val Lys Gly Phe Tyr Pro Ser Asp Ile Ala
            835                  840                 845

Val Glu Trp Glu Ser Asn Gly Gln Pro Glu Asn Asn Tyr Lys Thr Thr
        850                  855                  860

Pro Pro Val Leu Asp Ser Asp Gly Ser Phe Phe Leu Tyr Ser Arg Leu
865                 870                  875                 880

Thr Val Asp Lys Ser Arg Trp Gln Glu Gly Asn Val Phe Ser Cys Ser
                885                  890                 895

Val Met His Glu Ala Leu His Asn His Tyr Thr Gln Lys Ser Leu Ser
            900                  905                 910

Leu Ser Leu Gly Lys
        915

<210> SEQ ID NO 21
<211> LENGTH: 2748
<212> TYPE: DNA
<213> ORGANISM: Artificial Sequence
<220> FEATURE:
<223> OTHER INFORMATION: Synthetic

<400> SEQUENCE: 21
atggtgcttc tgtggtgtgt agtgagtctc tacttttatg gaatcctgca aagtgatgcc      60
tcagaacgct gcgatgactg gggactagac accatgaggc aaatccaagt gtttgaagat     120
gagccagctc gcatcaagtg cccactcttt gaacacttct tgaaattcaa ctacagcaca     180
gcccattcag ctggcttac tctgatctgg tattggacta gcaggaccg ggaccttgag       240 gagccaatta acttccgcct ccccgagaac cgcattagta aggagaaaga tgtgctgtgg     300
ttccggccca ctctcctcaa tgacactggc aactataccct gcatgttaag gaacactaca     360
tattgcagca agttgcatt tccccttggaa gttgttcaaa agacagctg tttcaattcc      420 cccatgaaac tcccagtgca taaactgtat atagaatatg gcattcagag gatcacttgt     480
ccaaatgtag atggatattt tccttccagt gtcaaaccga ctatcacttg gtatatgggc     540
tgttataaaa tacagaattt taataatgta atacccgaag gtatgaactt gagtttcctc     600
attgccttaa tttcaaataa tggaaattac acatgtgttg ttacatatcc agaaaatgga     660
cgtacgtttc atctcaccag gactctgact gtaaaggtag taggctctcc aaaaaatgca     720
gtgccccctg tgatccattc acctaatgat catgtggtct atgagaaaga accaggagag     780
gagctactca ttccctgtac ggtctatttt agttttctga tggattctcg caatgaggtt     840
tggtggacca ttgatggaaa aaacctgat gacatcacta ttgatgtcac cattaacgaa      900
agtataagtc atagtagaac agaagatgaa acaagaactc agattttgag catcaagaaa     960
gttacctctg aggatctcaa gcgcagctat gtctgtcatg ctagaagtgc caaaggcgaa    1020
```

-continued

```
gttgccaaag cagccaaggt gaagcagaaa gtgccagctc caagatacac agtgcacaca    1080
ggggctgcca gaagctgccg gtttcgtggg aggcattaca agcgggagtt caggctggaa    1140
ggggagcctg tagccctgag gtgcccccag gtgccctact ggttgtgggc ctctgtcagc    1200
ccccgcatca acctgacatg gcataaaaat gactctgcta ggacggtccc aggagaagaa    1260
gagacacgga tgtgggccca ggacggtgct ctgtggcttc tgccagcctt gcaggaggac    1320
tctggcacct acgtctgcac tactagaaat gcttcttact gtgacaaaat gtccattgag    1380
ctcagagttt ttgagaatac agatgctttc ctgccgttca tctcataccc gcaaattta    1440 accttgtcaa cctctggggt attagtatgc cctgacctga gtgaattcac ccgtgacaaa    1500
actgacgtga agattcaatg gtacaaggat tctcttcttt tggataaaga caatgagaaa    1560
tttctaagtg tgaggggac cactcactta ctcgtacacg atgtggccct ggaagatgct    1620
ggctattacc gctgtgtcct gacatttgcc catgaaggcc agcaatacaa catcactagg    1680
agtattgagc tacgcatcaa gaaaaaaaa gaagagacca ttcctgtgat catttccccc    1740
ctcaagacca tatcagcttc tctggggtca agactgacaa tcccatgtaa ggtgtttctg    1800
ggaaccggca cacccttaac caccatgctg tggtggacgg ccaatgacac ccacatagag    1860
agcgcctacc cgggaggccg cgtgaccgag gggccacgcc aggaatattc agaaaataat    1920
gagaactaca ttgaagtgcc attgattttt gatcctgtca agagagga tttgcacatg    1980 gattttaaat gtgttgtcca taatccctg agttttcaga cactacgcac cacagtcaag    2040
gaagcctcct ccacgttctc cggagacaaa actcacacat gcccaccgtg cccagcacct    2100
gaactcctgg ggggaccgtc agtcttcctc ttccccccaa aacccaagga caccctcatg    2160
atctcccgga cccctgaggt cacatgcgtg gtggtggacg tgagccacga agaccctgag    2220
gtcaagttca actggtacgt ggacggcgtg gaggtgcata atgccaagac aaagccgcgg    2280
gaggagcagt acaacagcac gtaccgtgtg gtcagcgtcc tcaccgtcct gcaccaggac    2340
tggctgaatg gcaaggagta caagtgcaag gtctccaaca aagccctccc agcccccatc    2400
gagaaaacca tctccaaagc caaagggcag ccccgagaac cacaggtgta caccctgccc    2460
ccatcccggg atgagctgac caagaaccag gtcagcctga cctgcctggt caaaggcttc    2520
tatcccagcg acatcgccgt ggagtgggag agcaatgggc agccggagaa caactacaag    2580
accacgcctc ccgtgctgga ctccgacggc tccttcttcc tctatagcaa gctcaccgtg    2640
gacaagagca ggtggcagca ggggaacgtc ttctcatgct ccgtgatgca tgaggctctg    2700
cacaaccact acacgcagaa gagcctctcc ctgtctccgg gtaaatga                2748
```

<210> SEQ ID NO 22
<211> LENGTH: 915
<212> TYPE: PRT
<213> ORGANISM: Artificial Sequence
<220> FEATURE:
<223> OTHER INFORMATION: Synthetic

<400> SEQUENCE: 22

```
Met Val Leu Leu Trp Cys Val Val Ser Leu Tyr Phe Tyr Gly Ile Leu
  1               5                  10                  15

Gln Ser Asp Ala Ser Glu Arg Cys Asp Asp Trp Gly Leu Asp Thr Met
                 20                  25                  30

Arg Gln Ile Gln Val Phe Glu Asp Glu Pro Ala Arg Ile Lys Cys Pro
             35                  40                  45

Leu Phe Glu His Phe Leu Lys Phe Asn Tyr Ser Thr Ala His Ser Ala
         50                  55                  60
```

-continued

```
Gly Leu Thr Leu Ile Trp Tyr Trp Thr Arg Gln Asp Arg Asp Leu Glu
 65                  70                  75                  80

Glu Pro Ile Asn Phe Arg Leu Pro Glu Asn Arg Ile Ser Lys Glu Lys
             85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
            165                 170                 175

Trp Tyr Met Gly Cys Tyr Lys Ile Gln Asn Phe Asn Asn Val Ile Pro
        180                 185                 190

Glu Gly Met Asn Leu Ser Phe Leu Ile Ala Leu Ile Ser Asn Asn Gly
    195                 200                 205

Asn Tyr Thr Cys Val Val Thr Tyr Pro Glu Asn Gly Arg Thr Phe His
210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
            245                 250                 255

Glu Pro Gly Glu Glu Leu Leu Ile Pro Cys Thr Val Tyr Phe Ser Phe
        260                 265                 270

Leu Met Asp Ser Arg Asn Glu Val Trp Trp Thr Ile Asp Gly Lys Lys
    275                 280                 285

Pro Asp Asp Ile Thr Ile Asp Val Thr Ile Asn Glu Ser Ile Ser His
290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
            325                 330                 335

Ala Lys Gly Glu Val Ala Lys Ala Lys Val Lys Gln Lys Val Pro
        340                 345                 350

Ala Pro Arg Tyr Thr Val His Thr Gly Ala Ala Arg Ser Cys Arg Phe
    355                 360                 365

Arg Gly Arg His Tyr Lys Arg Glu Phe Arg Leu Glu Gly Glu Pro Val
370                 375                 380

Ala Leu Arg Cys Pro Gln Val Pro Tyr Trp Leu Trp Ala Ser Val Ser
385                 390                 395                 400

Pro Arg Ile Asn Leu Thr Trp His Lys Asn Asp Ser Ala Arg Thr Val
            405                 410                 415

Pro Gly Glu Glu Glu Thr Arg Met Trp Ala Gln Asp Gly Ala Leu Trp
        420                 425                 430

Leu Leu Pro Ala Leu Gln Glu Asp Ser Gly Thr Tyr Val Cys Thr Thr
    435                 440                 445

Arg Asn Ala Ser Tyr Cys Asp Lys Met Ser Ile Glu Leu Arg Val Phe
450                 455                 460

Glu Asn Thr Asp Ala Phe Leu Pro Phe Ile Ser Tyr Pro Gln Ile Leu
465                 470                 475                 480
```

-continued

```
Thr Leu Ser Thr Ser Gly Val Leu Val Cys Pro Asp Leu Ser Glu Phe
            485                 490                 495
Thr Arg Asp Lys Thr Asp Val Lys Ile Gln Trp Tyr Lys Asp Ser Leu
            500                 505                 510
Leu Leu Asp Lys Asp Asn Glu Lys Phe Leu Ser Val Arg Gly Thr Thr
            515                 520                 525
His Leu Leu Val His Asp Val Ala Leu Glu Asp Ala Gly Tyr Tyr Arg
            530                 535                 540
Cys Val Leu Thr Phe Ala His Glu Gly Gln Gln Tyr Asn Ile Thr Arg
545                 550                 555                 560
Ser Ile Glu Leu Arg Ile Lys Lys Lys Glu Thr Ile Pro Val
                    565                 570                 575
Ile Ile Ser Pro Leu Lys Thr Ile Ser Ala Ser Leu Gly Ser Arg Leu
            580                 585                 590
Thr Ile Pro Cys Lys Val Phe Leu Gly Thr Gly Thr Pro Leu Thr Thr
            595                 600                 605
Met Leu Trp Trp Thr Ala Asn Asp Thr His Ile Glu Ser Ala Tyr Pro
            610                 615                 620
Gly Gly Arg Val Thr Glu Gly Pro Arg Gln Glu Tyr Ser Glu Asn Asn
625                 630                 635                 640
Glu Asn Tyr Ile Glu Val Pro Leu Ile Phe Asp Pro Val Thr Arg Glu
                    645                 650                 655
Asp Leu His Met Asp Phe Lys Cys Val Val His Asn Thr Leu Ser Phe
            660                 665                 670
Gln Thr Leu Arg Thr Thr Val Lys Glu Ala Ser Ser Thr Phe Ser Gly
            675                 680                 685
Asp Lys Thr His Thr Cys Pro Pro Cys Pro Ala Pro Glu Leu Leu Gly
            690                 695                 700
Gly Pro Ser Val Phe Leu Phe Pro Pro Lys Pro Lys Asp Thr Leu Met
705                 710                 715                 720
Ile Ser Arg Thr Pro Glu Val Thr Cys Val Val Val Asp Val Ser His
                    725                 730                 735
Glu Asp Pro Glu Val Lys Phe Asn Trp Tyr Val Asp Gly Val Glu Val
            740                 745                 750
His Asn Ala Lys Thr Lys Pro Arg Glu Glu Gln Tyr Asn Ser Thr Tyr
            755                 760                 765
Arg Val Val Ser Val Leu Thr Val Leu His Gln Asp Trp Leu Asn Gly
            770                 775                 780
Lys Glu Tyr Lys Cys Lys Val Ser Asn Lys Ala Leu Pro Ala Pro Ile
785                 790                 795                 800
Glu Lys Thr Ile Ser Lys Ala Lys Gly Gln Pro Arg Glu Pro Gln Val
                    805                 810                 815
Tyr Thr Leu Pro Pro Ser Arg Asp Glu Leu Thr Lys Asn Gln Val Ser
            820                 825                 830
Leu Thr Cys Leu Val Lys Gly Phe Tyr Pro Ser Asp Ile Ala Val Glu
            835                 840                 845
Trp Glu Ser Asn Gly Gln Pro Glu Asn Asn Tyr Lys Thr Thr Pro Pro
            850                 855                 860
Val Leu Asp Ser Asp Gly Ser Phe Phe Leu Tyr Ser Lys Leu Thr Val
865                 870                 875                 880
Asp Lys Ser Arg Trp Gln Gln Gly Asn Val Phe Ser Cys Ser Val Met
                    885                 890                 895
His Glu Ala Leu His Asn His Tyr Thr Gln Lys Ser Leu Ser Leu Ser
```

Pro Gly Lys
   915

<210> SEQ ID NO 23
<211> LENGTH: 2754
<212> TYPE: DNA
<213> ORGANISM: Artificial Sequence
<220> FEATURE:
<223> OTHER INFORMATION: Synthetic

<400> SEQUENCE: 23

| | | | | | |
|---|---|---|---|---|---|
| atggtgcttc | tgtggtgtgt | agtgagtctc | tacttttatg | gaatcctgca | aagtgatgcc | 60 |
| tcagaacgct | gcgatgactg | gggactagac | accatgaggc | aaatccaagt | gtttgaagat | 120 |
| gagccagctc | gcatcaagtg | cccactcttt | gaacacttct | tgaaattcaa | ctacagcaca | 180 |
| gcccattcag | ctggcttac | tctgatctgg | tattggacta | gcaggaccg | ggaccttgag | 240 |
| gagccaatta | acttccgcct | ccccgagaac | cgcattagta | aggagaaaga | tgtgctgtgg | 300 |
| ttccggccca | ctctcctcaa | tgacactggc | aactatacct | gcatgttaag | gaacactaca | 360 |
| tattgcagca | aagttgcatt | tcccttggaa | gttgttcaaa | aagacagctg | tttcaattcc | 420 |
| cccatgaaac | tcccagtgca | taaactgtat | atagaatatg | gcattcagag | gatcacttgt | 480 |
| ccaaatgtag | atggatattt | tccttccagt | gtcaaaccga | ctatcacttg | gtatatgggc | 540 |
| tgttataaaa | tacagaattt | taataatgta | atacccgaag | gtatgaactt | gagtttcctc | 600 |
| attgccttaa | tttcaaataa | tggaaattac | acatgtgttg | ttacatatcc | agaaaatgga | 660 |
| cgtacgtttc | atctcaccag | gactctgact | gtaaaggtag | taggctctcc | aaaaaatgca | 720 |
| gtgccccctg | tgatccattc | acctaatgat | catgtggtct | atgagaaaga | accaggagag | 780 |
| gagctactca | ttccctgtac | ggtctatttt | agttttctga | tggattctcg | caatgaggtt | 840 |
| tggtggacca | ttgatggaaa | aaacctgat | gacatcacta | ttgatgtcac | cattaacgaa | 900 |
| agtataagtc | atagtagaac | agaagatgaa | acaagaactc | agattttgag | catcaagaaa | 960 |
| gttacctctg | aggatctcaa | gcgcagctat | gtctgtcatg | ctagaagtgc | caaggcgaa | 1020 |
| gttgccaaag | cagccaaggt | gaagcagaaa | gtgccagctc | caagatacac | agtgcacaca | 1080 |
| ggggctgcca | gaagctgccg | gtttcgtggg | aggcattaca | agcgggagtt | caggctggaa | 1140 |
| ggggagcctg | tagccctgag | gtgcccccag | gtgccctact | ggttgtgggc | ctctgtcagc | 1200 |
| ccccgcatca | acctgacatg | gcataaaaat | gactctgcta | ggacggtccc | aggagaagaa | 1260 |
| gagacacgga | tgtgggccca | ggacggtgct | ctgtggcttc | tgccagcctt | gcaggaggac | 1320 |
| tctggcacct | acgtctgcac | tactagaaat | gcttcttact | gtgacaaaat | gtccattgag | 1380 |
| ctcagagttt | ttgagaatac | agatgctttc | ctgccgttca | tctcataccc | gcaaattta | 1440 |
| accttgtcaa | cctctggggt | attagtatgc | cctgacctga | gtgaattcac | ccgtgacaaa | 1500 |
| actgacgtga | agattcaatg | gtacaaggat | tctcttcttt | tggataaaga | caatgagaaa | 1560 |
| tttctaagtg | tgaggggac | cactcactta | ctcgtacacg | atgtggccct | ggaagatgct | 1620 |
| ggctattacc | gctgtgtcct | gacatttgcc | catgaaggcc | agcaatacaa | catcactagg | 1680 |
| agtattgagc | tacgcatcaa | gaaaaaaaaa | gaagagacca | ttcctgtgat | catttccccc | 1740 |
| ctcaagacca | tatcagcttc | tctggggtca | agactgacaa | tcccatgtaa | ggtgtttctg | 1800 |
| ggaaccggca | caccccttaac | caccatgctg | tggtggacgg | ccaatgacac | ccacatagag | 1860 |
| agcgcctacc | cgggaggccg | cgtgaccgag | gggccacgcc | aggaatattc | agaaaataat | 1920 |

```
gagaactaca ttgaagtgcc attgattttt gatcctgtca caagagagga tttgcacatg    1980
gattttaaat gtgttgtcca taatccctg agttttcaga cactacgcac cacagtcaag    2040
gaagcctcct ccacgttctc cggagagtcc aaatacggtc cgccatgccc atcatgccca    2100
gcacctgagt tcctgggggg accatcagtc ttcctgttcc ccccaaaacc caaggacact    2160
ctcatgatct cccggacccc tgaggtcacg tgcgtggtgg tggacgtgag ccaggaagac    2220
cccgaggtcc agttcaactg gtacgtggat ggcgtggagg tgcataatgc caagacaaag    2280
ccgcgggagg agcagttcaa cagcacgtac cgtgtggtca gcgtcctcac cgtcctgcac    2340
caggactggc tgaacggcaa ggagtacaag tgcaaggtct ccaacaaagg cctcccgtcc    2400
tccatcgaga aaaccatctc caaagccaaa gggcagcccc gagagccaca ggtgtacacc    2460
ctgcccccat cccaggagga tgaccaag aaccaggtca gcctgacctg cctggtcaaa    2520
ggcttctacc ccagcgacat cgccgtggag tgggagagca atgggcagcc ggagaacaac    2580
tacaagacca cgcctcccgt gctggactcc gacggctcct tcttcctcta cagcaggcta    2640
accgtggaca gagcaggtg gcaggagggg aatgtcttct catgctccgt gatgcatgag    2700
gctctgcaca accactacac acagaagagc ctctccctgt ctctgggtaa atga          2754
```

<210> SEQ ID NO 24
<211> LENGTH: 917
<212> TYPE: PRT
<213> ORGANISM: Artificial Sequence
<220> FEATURE:
<223> OTHER INFORMATION: Synthetic

<400> SEQUENCE: 24

```
Met Val Leu Leu Trp Cys Val Val Ser Leu Tyr Phe Tyr Gly Ile Leu
 1               5                  10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220
```

```
Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
            245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
        290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val His Thr Gly Ala Ala Arg Ser Cys Arg Phe
        355                 360                 365

Arg Gly Arg His Tyr Lys Arg Glu Phe Arg Leu Glu Gly Glu Pro Val
        370                 375                 380

Ala Leu Arg Cys Pro Gln Val Pro Tyr Trp Leu Trp Ala Ser Val Ser
385                 390                 395                 400

Pro Arg Ile Asn Leu Thr Trp His Lys Asn Asp Ser Ala Arg Thr Val
                405                 410                 415

Pro Gly Glu Glu Glu Thr Arg Met Trp Ala Gln Asp Gly Ala Leu Trp
            420                 425                 430

Leu Leu Pro Ala Leu Gln Glu Asp Ser Gly Thr Tyr Val Cys Thr Thr
        435                 440                 445

Arg Asn Ala Ser Tyr Cys Asp Lys Met Ser Ile Glu Leu Arg Val Phe
450                 455                 460

Glu Asn Thr Asp Ala Phe Leu Pro Phe Ile Ser Tyr Pro Gln Ile Leu
465                 470                 475                 480

Thr Leu Ser Thr Ser Gly Val Leu Val Cys Pro Asp Leu Ser Glu Phe
            485                 490                 495

Thr Arg Asp Lys Thr Asp Val Lys Ile Gln Trp Tyr Lys Asp Ser Leu
        500                 505                 510

Leu Leu Asp Lys Asp Asn Glu Lys Phe Leu Ser Val Arg Gly Thr Thr
        515                 520                 525

His Leu Leu Val His Asp Val Ala Leu Glu Asp Ala Gly Tyr Tyr Arg
        530                 535                 540

Cys Val Leu Thr Phe Ala His Glu Gly Gln Gln Tyr Asn Ile Thr Arg
545                 550                 555                 560

Ser Ile Glu Leu Arg Ile Lys Lys Lys Glu Glu Thr Ile Pro Val
                565                 570                 575

Ile Ile Ser Pro Leu Lys Thr Ile Ser Ala Ser Leu Gly Ser Arg Leu
            580                 585                 590

Thr Ile Pro Cys Lys Val Phe Leu Gly Thr Gly Thr Pro Leu Thr Thr
        595                 600                 605

Met Leu Trp Trp Thr Ala Asn Asp Thr His Ile Glu Ser Ala Tyr Pro
        610                 615                 620

Gly Gly Arg Val Thr Glu Gly Pro Arg Gln Glu Tyr Ser Glu Asn Asn
625                 630                 635                 640
```

```
Glu Asn Tyr Ile Glu Val Pro Leu Ile Phe Asp Pro Val Thr Arg Glu
                645                 650                 655
Asp Leu His Met Asp Phe Lys Cys Val Val His Asn Thr Leu Ser Phe
            660                 665                 670
Gln Thr Leu Arg Thr Thr Val Lys Glu Ala Ser Ser Thr Phe Ser Gly
        675                 680                 685
Glu Ser Lys Tyr Gly Pro Pro Cys Pro Ser Cys Pro Ala Pro Glu Phe
    690                 695                 700
Leu Gly Gly Pro Ser Val Phe Leu Phe Pro Pro Lys Pro Lys Asp Thr
705                 710                 715                 720
Leu Met Ile Ser Arg Thr Pro Glu Val Thr Cys Val Val Val Asp Val
                725                 730                 735
Ser Gln Glu Asp Pro Glu Val Gln Phe Asn Trp Tyr Val Asp Gly Val
            740                 745                 750
Glu Val His Asn Ala Lys Thr Lys Pro Arg Glu Glu Gln Phe Asn Ser
        755                 760                 765
Thr Tyr Arg Val Val Ser Val Leu Thr Val Leu His Gln Asp Trp Leu
    770                 775                 780
Asn Gly Lys Glu Tyr Lys Cys Lys Val Ser Asn Lys Gly Leu Pro Ser
785                 790                 795                 800
Ser Ile Glu Lys Thr Ile Ser Lys Ala Lys Gly Gln Pro Arg Glu Pro
                805                 810                 815
Gln Val Tyr Thr Leu Pro Pro Ser Gln Glu Glu Met Thr Lys Asn Gln
            820                 825                 830
Val Ser Leu Thr Cys Leu Val Lys Gly Phe Tyr Pro Ser Asp Ile Ala
        835                 840                 845
Val Glu Trp Glu Ser Asn Gly Gln Pro Glu Asn Asn Tyr Lys Thr Thr
    850                 855                 860
Pro Pro Val Leu Asp Ser Asp Gly Ser Phe Phe Leu Tyr Ser Arg Leu
865                 870                 875                 880
Thr Val Asp Lys Ser Arg Trp Gln Glu Gly Asn Val Phe Ser Cys Ser
                885                 890                 895
Val Met His Glu Ala Leu His Asn His Tyr Thr Gln Lys Ser Leu Ser
            900                 905                 910
Leu Ser Leu Gly Lys
        915

<210> SEQ ID NO 25
<211> LENGTH: 2754
<212> TYPE: DNA
<213> ORGANISM: Artificial Sequence
<220> FEATURE:
<223> OTHER INFORMATION: Synthetic

<400> SEQUENCE: 25
atggtgcttc tgtggtgtgt agtgagtctc tacttttatg gaatcctgca aagtgatgcc    60
tcagaacgct gcgatgactg gggactagac accatgaggc aaatccaagt gtttgaagat   120
gagccagctc gcatcaagtg cccactcttt gaacacttct tgaaattcaa ctacagcaca   180
gcccattcag ctggccttac tctgatctgg tattggacta ggcaggaccg ggaccttgag   240
gagccaatta acttccgcct ccccgagaac cgcattagta aggagaaaga tgtgctgtgg   300
ttccggccca ctctcctcaa tgacactggc aactataccc tgcatgttaa gaacactaca   360
tattgcagca agttgcatt tcccttggaa gttgttcaaa aagacagctg tttcaattcc   420
cccatgaaac tcccagtgca taaactgtat atagaatatg gcattcagag gatcacttgt   480
```

```
ccaaatgtag atggatattt tccttccagt gtcaaaccga ctatcacttg gtatatgggc    540
tgttataaaa tacagaattt taataatgta atacccgaag gtatgaactt gagtttcctc    600
attgccttaa tttcaaataa tggaaattac acatgtgttg ttacatatcc agaaaatgga    660
cgtacgtttc atctcaccag gactctgact gtaaaggtag taggctctcc aaaaaatgca    720 gtgcccctg tgatccattc acctaatgat catgtggtct atgagaaaga accaggagag    780
gagctactca ttccctgtac ggtctatttt agttttctga tggattctcg caatgaggtt    840
tggtggacca ttgatggaaa aaaacctgat gacatcacta ttgatgtcac cattaacgaa    900
agtataagtc atagtagaac agaagatgaa acaagaactc agattttgag catcaagaaa    960
gttacctctg aggatctcaa gcgcagctat gtctgtcatg ctagaagtgc caaaggcgaa    1020
gttgccaaag cagccaaggt gaagcagaaa gtgccagctc aagatacac agtgcacaca    1080 ggggctgcca gaagctgccg gtttcgtggg aggcattaca agcgggagtt caggctggaa    1140
ggggagcctg tagccctgag gtgcccccag gtgccctact ggttgtgggc ctctgtcagc    1200
ccccgcatca acctgacatg gcataaaaat gactctgcta ggacggtccc aggagaagaa    1260
gagacacgga tgtgggccca ggacggtgct ctgtggcttc tgccagcctt gcaggaggac    1320
tctggcacct acgtctgcac tactagaaat gcttcttact gtgacaaaat gtccattgag    1380
ctcagagttt ttgagaatac agatgctttc ctgccgttca tctcatatccc gcaaattta    1440 accttgtcaa cctctgggt attagtatgc cctgacctga gtgaattcac ccgtgacaaa    1500
actgacgtga agattcaatg gtacaaggat tctcttcttt tggataaaga caatgagaaa    1560
tttctaagtg tgaggggac cactcactta ctcgtacacg atgtggccct ggaagatgct    1620
ggctattacc gctgtgtcct gacatttgcc catgaaggcc agcaatacaa catcactagg    1680
agtattgagc tacgcatcaa gaaaaaaaa gaagagacca ttcctgtgat catttccccc    1740
ctcaagacca tatcagcttc tctggggtca agactgacaa tcccatgtaa ggtgtttctg    1800
ggaaccggca caccccttaac caccatgctg tggtggacgg ccaatgacac ccacatagag    1860
agcgcctacc cggaggccg cgtgaccgag gggccacgcc aggaatattc agaaaataat    1920
gagaactaca ttgaagtgcc attgattttt gatcctgtca caagagagga tttgcacatg    1980
gattttaaat gtgttgtcca taatacccctg agttttcaga cactacgcac acagtcaag    2040 gaagcctcct ccacgttctc cggagagtcc aaatacggtc cgccatgccc accatgccca    2100
gcacctgagt tcctgggggg accatcagtc ttcctgttcc ccccaaaacc caaggacact    2160
ctcatgatct cccggacccc tgaggtcacg tgcgtggtgg tggacgtgag ccaggaagac    2220
cccgaggtcc agttcaactg gtacgtggat ggcgtggagg tgcataatgc caagacaaag    2280
ccgcgggagg agcagttcaa cagcacgtac cgtgtggtca gcgtcctcac cgtcctgcac    2340
caggactggc tgaacggcaa ggagtacaag tgcaaggtct ccaacaaagg cctcccgtcc    2400
tccatcgaga aaaccatctc caaagccaaa gggcagcccc gagagccaca ggtgtacacc    2460
ctgcccccat cccaggagga gatgaccaag aaccaggtca gcctgacctg cctggtcaaa    2520
ggcttctacc ccagcgacat cgccgtggag tgggagagca atgggcagcc ggagaacaac    2580
tacaagacca cgcctcccgt gctggactcc gacggctcct tcttcctcta cagcaggcta    2640
accgtggaca agagcaggtg gcaggagggg aatgtcttct catgctccgt gatgcatgag    2700
gctctgcaca accactacac acagaagagc ctctccctgt ctctgggtaa atga    2754
```

<210> SEQ ID NO 26

<211> LENGTH: 917
<212> TYPE: PRT
<213> ORGANISM: Artificial Sequence
<220> FEATURE:
<223> OTHER INFORMATION: Synthetic

<400> SEQUENCE: 26

```
Met Val Leu Leu Trp Cys Val Val Ser Leu Tyr Phe Tyr Gly Ile Leu
 1               5                  10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
           100                 105                 110

Thr Cys Met Leu Arg Asn Thr Thr Tyr Cys Ser Lys Val Ala Phe Pro
       115                 120                 125

Leu Glu Val Val Gln Lys Asp Ser Cys Phe Asn Ser Pro Met Lys Leu
   130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
               165                 170                 175

Trp Tyr Met Gly Cys Tyr Lys Ile Gln Asn Phe Asn Asn Val Ile Pro
           180                 185                 190

Glu Gly Met Asn Leu Ser Phe Leu Ile Ala Leu Ile Ser Asn Asn Gly
       195                 200                 205

Asn Tyr Thr Cys Val Val Thr Tyr Pro Glu Asn Gly Arg Thr Phe His
   210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
               245                 250                 255

Glu Pro Gly Glu Glu Leu Leu Ile Pro Cys Thr Val Tyr Phe Ser Phe
           260                 265                 270

Leu Met Asp Ser Arg Asn Glu Val Trp Trp Thr Ile Asp Gly Lys Lys
       275                 280                 285

Pro Asp Asp Ile Thr Ile Asp Val Thr Ile Asn Glu Ser Ile Ser His
   290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
               325                 330                 335

Ala Lys Gly Glu Val Ala Lys Ala Ala Lys Val Lys Gln Lys Val Pro
           340                 345                 350

Ala Pro Arg Tyr Thr Val His Thr Gly Ala Ala Arg Ser Cys Arg Phe
       355                 360                 365

Arg Gly Arg His Tyr Lys Arg Glu Phe Arg Leu Glu Gly Glu Pro Val
   370                 375                 380
```

-continued

```
Ala Leu Arg Cys Pro Gln Val Pro Tyr Trp Leu Trp Ala Ser Val Ser
385                 390                 395                 400

Pro Arg Ile Asn Leu Thr Trp His Lys Asn Asp Ser Ala Arg Thr Val
            405                 410                 415

Pro Gly Glu Glu Thr Arg Met Trp Ala Gln Asp Gly Ala Leu Trp
        420                 425                 430

Leu Leu Pro Ala Leu Gln Glu Asp Ser Gly Thr Tyr Val Cys Thr Thr
            435                 440                 445

Arg Asn Ala Ser Tyr Cys Asp Lys Met Ser Ile Glu Leu Arg Val Phe
    450                 455                 460

Glu Asn Thr Asp Ala Phe Leu Pro Phe Ile Ser Tyr Pro Gln Ile Leu
465                 470                 475                 480

Thr Leu Ser Thr Ser Gly Val Leu Val Cys Pro Asp Leu Ser Glu Phe
                485                 490                 495

Thr Arg Asp Lys Thr Asp Val Lys Ile Gln Trp Tyr Lys Asp Ser Leu
            500                 505                 510

Leu Leu Asp Lys Asp Asn Glu Lys Phe Leu Ser Val Arg Gly Thr Thr
        515                 520                 525

His Leu Leu Val His Asp Val Ala Leu Glu Asp Ala Gly Tyr Tyr Arg
    530                 535                 540

Cys Val Leu Thr Phe Ala His Glu Gly Gln Gln Tyr Asn Ile Thr Arg
545                 550                 555                 560

Ser Ile Glu Leu Arg Ile Lys Lys Lys Glu Glu Thr Ile Pro Val
                565                 570                 575

Ile Ile Ser Pro Leu Lys Thr Ile Ser Ala Ser Leu Gly Ser Arg Leu
            580                 585                 590

Thr Ile Pro Cys Lys Val Phe Leu Gly Thr Gly Thr Pro Leu Thr Thr
        595                 600                 605

Met Leu Trp Trp Thr Ala Asn Asp Thr His Ile Glu Ser Ala Tyr Pro
    610                 615                 620

Gly Gly Arg Val Thr Glu Gly Pro Arg Gln Glu Tyr Ser Glu Asn Asn
625                 630                 635                 640

Glu Asn Tyr Ile Glu Val Pro Leu Ile Phe Asp Pro Val Thr Arg Glu
                645                 650                 655

Asp Leu His Met Asp Phe Lys Cys Val Val His Asn Thr Leu Ser Phe
            660                 665                 670

Gln Thr Leu Arg Thr Thr Val Lys Glu Ala Ser Ser Thr Phe Ser Gly
        675                 680                 685

Glu Ser Lys Tyr Gly Pro Pro Cys Pro Pro Cys Pro Ala Pro Glu Phe
    690                 695                 700

Leu Gly Gly Pro Ser Val Phe Leu Phe Pro Pro Lys Pro Lys Asp Thr
705                 710                 715                 720

Leu Met Ile Ser Arg Thr Pro Glu Val Thr Cys Val Val Val Asp Val
                725                 730                 735

Ser Gln Glu Asp Pro Glu Val Gln Phe Asn Trp Tyr Val Asp Gly Val
            740                 745                 750

Glu Val His Asn Ala Lys Thr Lys Pro Arg Glu Glu Gln Phe Asn Ser
        755                 760                 765

Thr Tyr Arg Val Val Ser Val Leu Thr Val Leu His Gln Asp Trp Leu
    770                 775                 780

Asn Gly Lys Glu Tyr Lys Cys Lys Val Ser Asn Lys Gly Leu Pro Ser
785                 790                 795                 800
```

```
Ser Ile Glu Lys Thr Ile Ser Lys Ala Lys Gly Gln Pro Arg Glu Pro
                805             810                 815

Gln Val Tyr Thr Leu Pro Pro Ser Gln Glu Glu Met Thr Lys Asn Gln
            820             825                 830

Val Ser Leu Thr Cys Leu Val Lys Gly Phe Tyr Pro Ser Asp Ile Ala
        835             840                 845

Val Glu Trp Glu Ser Asn Gly Gln Pro Glu Asn Asn Tyr Lys Thr Thr
    850             855                 860

Pro Pro Val Leu Asp Ser Asp Gly Ser Phe Phe Leu Tyr Ser Arg Leu
865             870             875                     880

Thr Val Asp Lys Ser Arg Trp Gln Glu Gly Asn Val Phe Ser Cys Ser
            885             890                 895

Val Met His Glu Ala Leu His Asn His Tyr Thr Gln Lys Ser Leu Ser
            900             905                 910

Leu Ser Leu Gly Lys
            915
```